(12) United States Patent
Mayer et al.

(10) Patent No.: US 6,589,915 B1
(45) Date of Patent: Jul. 8, 2003

(54) BENZOHETERO CYCLYLCYCLO HEXENONES AND THEIR USE AS HERBICIDES

(75) Inventors: Guido Mayer, Neustadt (DE); Ernst Baumann, Dudenhofen (DE); Wolfgang von Deyn, Neustadt (DE); Steffen Kudis, Mannheim (DE); Klaus Langemann, Worms (DE); Ulf Misslitz, Neustadt (DE); Ulf Neidlein, Mannheim (DE); Matthias Witschel, Ludwigshafen (DE); Michael Rack, Heidelberg (DE); Thorsten Volk, Mannheim (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/959,801

(22) PCT Filed: May 5, 2000

(86) PCT No.: PCT/EP00/04042

§ 371 (c)(1),
(2), (4) Date: Nov. 7, 2001

(87) PCT Pub. No.: WO00/68210

PCT Pub. Date: Nov. 16, 2000

(30) Foreign Application Priority Data

May 7, 1999 (DE) .......................... 199 21 201

(51) Int. Cl.$^7$ .......................... A01N 43/78; C07D 277/62
(52) U.S. Cl. ........................................ 504/267; 548/179
(58) Field of Search .......................... 548/179; 504/267

(56) References Cited

FOREIGN PATENT DOCUMENTS

| EP | 0 283 261 | 9/1988 |
|----|-----------|--------|
| WO | WO 96/05182 | 2/1996 |
| WO | WO 97/09324 | 3/1997 |
| WO | WO 99/03845 | 1/1999 |

*Primary Examiner*—Ceila Chang
*Assistant Examiner*—Golam M. M. Shameem
(74) *Attorney, Agent, or Firm*—Keil & Weinkauf

(57) ABSTRACT

The invention relates to cyclohexenone derivatives of benzo-condensed, unsaturated 5-ring nitrogen heterocycles of general formula (I) wherein X represents N or a group C—R$^3$, Y represents O, S, SO, SO$_2$ or NR$^4$ or X—Y represent S=N and X represents sulfur, and the variables R$^1$, R$^2$ and Hex have the meanings given in claim 1. The invention also relates to a method for producing these compounds, to agents containing these compounds, and to their use as herbicides.

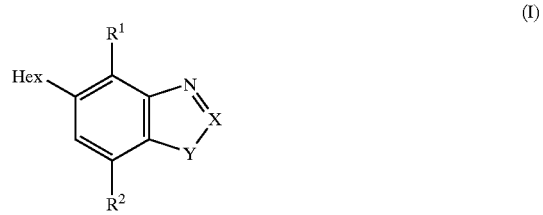

(I)

5 Claims, No Drawings

BENZOHETERO CYCLYLCYCLO HEXENONES AND THEIR USE AS HERBICIDES

This application is a 371 of PCT/EP00/04042 May 5, 2000.

The present invention relates to cyclohexenone derivatives of benzo-fused unsaturated 5-membered nitrogen heterocycles, to processes for preparing such cylohexenone derivatives, to compositions comprising such compounds, and to the use of the cyclohexenone derivatives or of the compositions comprising them for controlling harmful plants.

WO 96/05182 discloses saccharin derivatives having herbicidal action which are substituted on the benzene ring of the saccharin skeleton by a (2-cyclohexane-1,3-dione) carbonyl radical.

WO 99/03845 discloses cyclohexane-1,3-diones which have a benzoyl radical in the 2-position. The benzoyl radical for its part can be substituted by heteroaromatic compounds. The compounds have herbicidal action.

WO 97/09324 discloses cyclohexane-1,3-diones having herbicidal action which have a benzo-fused sulfur heterocycle, for example a thiochromane or a benzodihydrothiophene radical, which is attached via a carbonyl group, in the 2-position.

EP-A 283 261 discloses similar compounds in which the cyclohexenone ring is substituted in the 2-position by a heteroaromatic radical. The heteroaromatic radicals mentioned are sulfur-, nitrogen- and/or oxygen-containing 5-membered or 6-membered heterocycles.

However, the herbicidal properties of the compounds known from the publications mentioned and their compatibility with crop plants do not meet all of the criteria required from herbicides.

It is an object of the present invention to provide novel compounds having herbicidal action which preferably have greater activity than the herbicidal substances of the prior art and/or better selectivity with respect to harmful plants.

We have found that this object is achieved by cyclohexenone derivatives of benzo-fused unsaturated 5-membered nitrogen heterocycles of the formula I defined below.

Consequently, the present invention relates to cyclohexenone derivatives of benzo-fused unsaturated 5-membered nitrogen heterocycles of the formula I,

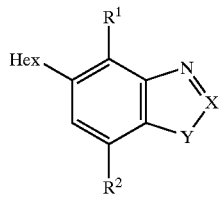

I in which
X is N or a group C—$R^3$;
Y is O, S, SO, $SO_2$ or $NR^4$
or
X–Y is S=N, and X is sulfur;
$R^1$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, or di-($C_1$–$C_6$-alkyl)amino-$C_1$–$C_6$-alkyl;

$R^2$ is hydrogen, halogen or $C_1$–$C_6$-alkyl;

$R^3$ is hydrogen, halogen, nitro, cyano, hydroxyl, amino, mercapto, thiocyanato, hydrazide, $C_1$–$C_6$-alkyl, $C_1$–$C_6$-haloalkyl, $C_1$–$C_6$-hydroxyalkyl, $C_1$–$C_6$-aminoalkyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_1$–$C_6$-hydroxyalkoxy, $C_1$–$C_6$-alkoxy-$C_1$–$C_6$-alkoxy, $C_3$–$C_6$-cycloalkyl, is $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy or hydroxyl, is $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, is phenyl, naphthyl, heterocyclyl, phenoxy, phenylamino, diphenylamino, where the phenyl and heterocyclyl groups of the six last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, is $C(O)OR^5$, or $C(O)N(R^6)R^7$; and $R^4$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy; where $R^5$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl or heterocyclyl, where the three last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

$R^6$, $R^7$ independently of one another are hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, are phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy; and Hex is substituted (3-oxo-1-cyclohexen-2-yl)carbonyl of the formula IIa or is substituted (1,3-dioxo-2-cyclohexyl)methylidene of the formula IIb

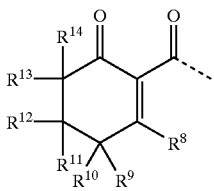

IIa

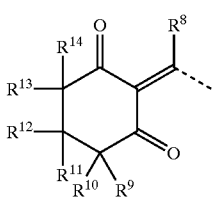

IIb where the variables $R^8$ to $R^{14}$ are as defined below:

$R^8$ is hydroxyl, mercapto, halogen, $OR^{15}$, $SR^{15}$, $SOR^{16}$, $SO_2R^{16}$, $OSO_2R^{16}$, $P(O)R^{17}R^{18}$, $OP(O)R^{17}R^{18}$, $P(S)R^{17}R^{18}$, $OP(S)R^{17}R^{18}$, $NR^{19}R^{20}$, $ONR^{19}R^{20}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$, $R^{13}$ independently of one another are hydrogen, $C_1$–$C_4$-alkyl or $C_1$–$C_4$-alkoxycarbonyl;

$R^{10}$, $R^{12}$, $R^{14}$ independently of one another are hydrogen or $C_1$–$C_4$-alkyl;

$R^{11}$ is hydrogen, halogen, hydroxyl, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-haloalkoxycarbonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one to three $C_1$–$C_4$-alkyl radicals;

or $R^{10}$ and $R^{12}$ or $R^{12}$ and $R^{14}$ together form a π bond or a $C_1$–$C_5$-alkyl chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{14}$ together form a $C_1$–$C_4$-alkyl chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^{11}$ and $R^{12}$ together form a —O—$(CH_2)_p$—O—, —O—$(CH_2)_p$—S—, —S—$(CH_2)_p$—S—, —O—$(CH2)_q$— or —S—$(CH2)_q$— chain in which p is 2, 3, 4 or 5 and q is 2, 3, 4, 5 or 6, which may be substituted by one, two or three radicals from the following group: halogen, cyano, $C_1$–$C_4$-alkyl, $C_1$–$C_4$-haloalkyl or $C_1$–C4-alkoxycarbonyl;

or $R^{11}$ and $R^{12}$ together with the carbon to which they are attached form a carbonyl group;

where $R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one, two or three of the following groups: cyano, $C_1$–$C_4$-alkoxy, $C_1$–$C_4$-alkylthio, di($C_1$–$C_4$-alkyl)amino., $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenylaminocarbonyl, N-($C_1$–$C_6$-alkyl)-N-phenylaminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N-($C_1$–$C_6$-alkyl)-N-heterocyclylaminocarbonyl or heterocyclyl-$C_1$–$C_6$-alkenylcarbonyl, where the phenyl or the heterocyclyl radical of the 18 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{16}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl, is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$- alkoxy, $C_1$–$C_4$-haloalkoxy or $C_1$–$C_4$-alkoxycarbonyl;

$R^{17}$, $R^{18}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl or alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)aminocarbonyl or $C_3$–$C_6$-cycloalkyl, is phenyl, phenyl-$C_1$–$C_4$ -alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is hydrogen, $C_1$–$C_6$-alkyl, $C_3$–$C_6$-alkenyl or $C_3$–$C_6$-alkynyl;

and their agriculturally useful salts.

Furthermore, we have found herbicidal compositions which comprise the cyclohexenone derivatives of the formula I and have very good herbicidal action. Moreover, we have found processes for preparing these compositions and methods for controlling undesirable vegetation using the cyclohexenone derivatives of the formula I.

Depending on the substitution pattern, the compounds of the formula I may contain one or more chiral centers, in which case they are present enantiomers or diastereomer mixtures. The invention provides both the pure enantiomers or diastereomers and their mixtures.

The compounds of the formula I may also be present in the form of their agriculturally useful salts, the type of salt generally being immaterial. In general, the salts of those cations or the acid addition salts of those acids are suitable whose cations and anions, respectively, do not negatively affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, 1 to 4 hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

For $R^8$=hydroxyl or mercapto {Z=O,S}, IIa also represents the tautomeric forms IIa', IIa" and IIa''',

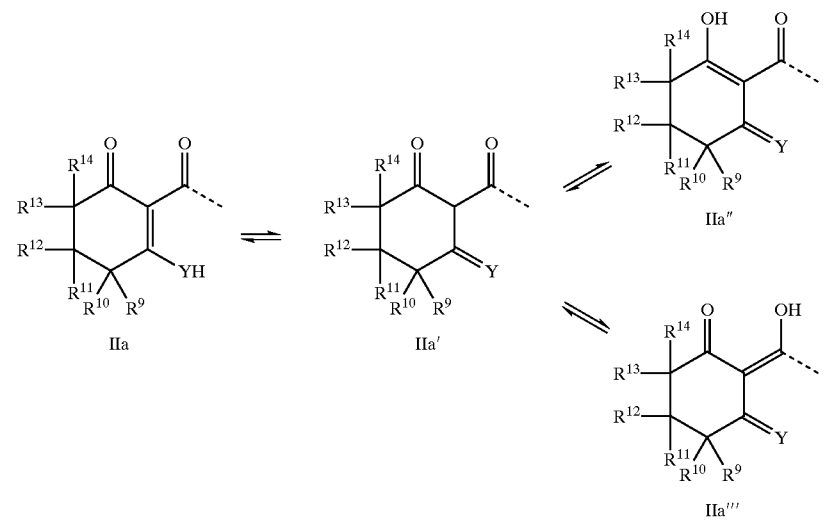

and IIb also represents the tautomeric forms IIb', IIb" and IIb'''.

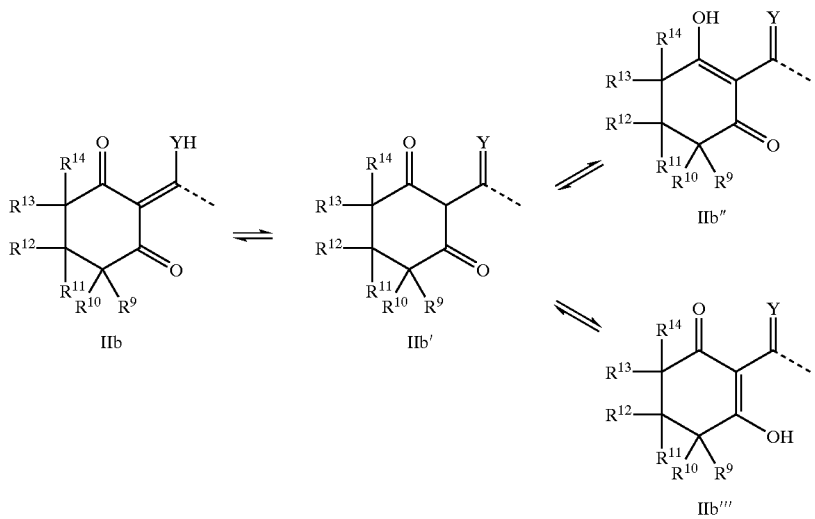

The organic molecular moieties mentioned for the substituents $R^1$ to $R^{20}$ or as radicals on phenyl and heterocyclyl radicals are collective terms for individual enumerations of the particular group members. All hydrocarbon chains, i.e. all alkyl, haloalkyl, alkoxy, haloalkoxy, alkylthio, haloalkylthio, alkylsulfinyl, haloalkylsulfinyl, alkylsulfonyl, haloalkylsulfonyl, N-alkylamino, N,N-dialkylamino, N-haloalkylamino, N-alkoxyamino, N-alkoxy-N-alkylamino, N-alkylcarbonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, alkoxyiminoalkyl, phenylalkylcarbonyl, heterocyclylalkylcarbonyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy, alkanediyl, alkenediyl, alkadienediyl or alkynediyl moieties can be straight-chain or branched. Unless indicated otherwise, halogenated substituents preferably carry one to five identical or different halogen atoms. The expression halogen represents in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkylamino, di($C_1$–$C_6$-alkyl)amino, N-($C_1$–$C_6$-alkoxy)-N-($C_1$–$C_6$-alkyl)amino, N-($C_1$–$C_6$-alkoxy)-N-($C_1$–$C_6$-alkyl)aminocarbonyl, N-($C_3$–$C_6$-alkenyl)-N-($C_1$–$C_6$-alkyl)aminocarbonyl, ($C_3$–$C_6$-alkynyl)-N-($C_1$–$C_6$-alkyl)aminocarbonyl, N-($C_1$–$C_6$-alkyl)-N-phenylaminocarbonyl, N-($C_1$–$C_6$-alkyl)-N-heterocyclylaminocarbonyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N-$C_1$–$C_6$-haloalkylamino: $C_1$–$C_4$-haloalkyl, as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N-$C_1$–$C_6$-alkoxyamino, N-($C_1$–$C_6$-alkoxy)-N-($C_1$–$C_6$-alkyl)amino, $C_1$–$C_6$-alkoxyimino-$C_1$–$C_6$-alkyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl and N-($C_3$–$C_6$-alkynyl)-N-($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropelntoxy, 5-bromopentoxy, 5-iodopentoxy, undecafluoropentoxy, 6-fluorohexoxy, 6-chlorohexoxy, 6-bromohexoxy, 6iodohexoxy or dodecafluorohexoxy;

$C_1$–$C_4$-alkylthio ($C_1$–$C_4$-alkylsulfanyl: $C_1$–$C_4$-alkyl-S—): for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of $C_1$–$C_6$-alkylthiocarbonyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio as mentioned above, and also 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_4$-alkylsulfinyl ($C_1$–$C_4$-alkyl-S(=O)—): for example, methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$–$C_6$-alkylsulfinyl: $C_1$–$C_4$-alkylsulfinyl as mentioned above, and also pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_4$-haloalkylsulfinyl: a $C_1$–$C_4$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_6$-haloalkylsulfinyl: $C_1$–$C_4$-haloalkylsulfinyl as mentioned above, and also 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S($=$O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

$C_1$–$C_6$-alkylsulfonyl: $C_1$–$C_4$-alkylsulfonyl, as mentioned above, and also pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-iethylpropylsulfonyl, hexylsulfonyl, 1-methylpentylsulfonyl, 2-methylpentylsulfonyl , 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloto-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_6$-haloalkylsulfonyl: $C_1$–$C_4$-haloalkylsulfonyl as mentioned above, and also 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino: methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonyl-$C_1$–$C_6$-alkyl, $C_1$–$C_6$-alkylcarbonylamino: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethyibutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-haloalkylcarbonyl: a $C_1$–$C_4$-alkylcarbonyl radical as mentioned above which is partially or fully substituted by fluorine, chlorine, bromine and/or iodine, i.e. for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl;

$C_1$–$C_6$-haloalkylcarbonyl: a $C_1$–$C_4$-haloalkylcarbonyl radical as mentioned above, and also 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl: i.e, for example, methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$–$C_6$-alkoxycarbonyl: $C_1$–$C_4$-alkoxycarbonyl as mentioned above, and also, for example, pentoxycarbonyl, 1-methylbutokycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chlorb-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or 4-iodobutoxycarbonyl;

$C_1$–$C_6$-halooxycarbonyl: a $C_1$–$C_4$-halooxycarbonyl radical as mentioned above, and also 5-fluoropentoxycarbonyl, 5-chloropentoxycarbonyl, 5-bromopentoxydarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminodarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyljaminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N- propylaminocarbonyl, N-butyl-N-(1-methylethyl) aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl) aminocarbonyl;

di($C_1$–$C_6$-alkyl)aminocarbonyl: di($C_1$–$C_4$-alkyl) aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl) aminocarbonyl, N-methyl-N-(1,1,2-trimethylpropyl) aminocarbonyl, N-methyl-N-(1,2,2-trimethylpropyl) aminocarbonyl, N-methyl-N-(1-ethyl-1-methylpropyl) aminocarbonyl, N-methyl-N-(1-ethyl-2-methylpropyl) aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl) aminocarbonyl, N-ethyl-N-(1,2-dimethylpropyl) aminocarbonyl, N-ethyl-N-(1-methylpentyl) aminocarbonyl, N-ethyl-N-(2-methylpentyl) aminocarbonyl, N-ethyl-N-(3-methylpentyl) aminocarbonyl, N-ethyl-N-(4-methylpentyl) aminocarbonyl, N-ethyl-N-(1,1-dimethylbutyl) aminocarbonyl, N-ethyl-N-(1,2-dimethylbutyl) aminocarbonyl, N-ethyl-N-(1,3-dimethylbutyl) aminocarbonyl, N-ethyl-N-(2,2-dimethylbutyl) aminocarbonyl, N-ethyl-N-(2,3-dimethylbutyl) aminocarbonyl, N-ethyl-N-(3,3-dimethylbutyl) aminocarbonyl, N-ethyl-N-(1-ethylbutyl) aminocarbonyl, N-ethyl-N-(2-ethylbutyl) aminocarbonyl, N-ethyl-N-(1,1,2-trimethylpropyl) aminocarbonyl, N-ethyl-N-(1,2,2-trimethylpropyl) aminocarbonyl, N-ethyl-N-(1-ethyl-1-methylpropyl) aminocarbonyl, N-ethyl-N-(1-ethyl-2-methylpropyl) aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl) aminothiocarbonyl, N-ethyl-N-(2-methylpropyl) aminothiocarbonyl, N-ethyl-N-(1,1-dimethylethyl) aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl) aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl) aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethyl propyl)aminothiocarbonyl, N-methyl-N-(1-ethyl-1-methylpropyl) aminothiocarbonyl, N-methyl-N-(1-ethyl-2-methylpropyl)aminothiocarbonyl, N-ethyl-N-pentylaminothiocarbonyl, N-ethyl-N-(1-methylbutyl) aminothiocarbonyl, N-ethyl-N-(2-methylbutyl) aminothiocarbonyl, N-ethyl-N-(3-methylbutyl) aminothiocarbonyl, N-Ethyl-N-(2,2-dimethylpropyl)

aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(12-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_6$-hydroxyalkyl: $C_1$–$C_6$-alkyl which is substituted by one to three OH groups, for example hydroxymethyl, 1-hydroxyethyl, 2-hydroxyethyl, 1,2-bishydroxyethyl, 1-hydroxypropyl, 2-hydroxypropyl, 3-hydroxypropyl, 4-hydroxybutyl, 2,2-dimethyl-3-hydroxypropyl;

phenyl-$C_1$–$C_6$-alkyl: $C_1$–$C_6$-alkyl which is substituted by a phenyl radical, for example benzyl, 1-phenylethyl and 2-phenylethyl, where the phenyl radical may, in the manner mentioned, be partially or fully halogenated or may carry one to three of the substituents mentioned above for phenyl; correspondingly, heterocyclyl-$C_1$–$C_6$-alkyl is a $C_1$–$C_6$-alkyl which is substituted by a heterocyclyl radical;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_6$-alkoxy-$C_1$–$C_6$-alkoxy, and the alkoxyalkoxy moieties of $C_1$–$C_6$-alkoxy-$C_1$–$C_6$-alkoxycarbonyl: $C_1$–$C_6$-alkoxy which is substituted by $C_1$–$C_6$-alkoxy as mentioned above, i.e, for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_1$–$C_6$-alkylcarbonyl-$C_1$–$C_6$-alkyl: $C_1$–$C_6$-alkyl which is substituted by a $C_1$–$C_6$-alkylcarbonyl group, where both of the $C_1$–$C_6$-alkyl groups may carry one or more substituents selected from $C_1$–$C_4$-alkoxy and/or hydroxyl: for example acetylmethyl (=2-oxopropyl), 2-(acetyl)ethyl (=3-oxo-n-butyl), 3-oxo-n-pentyl, 1,1-dimethyl-2-oxopropyl, 3-hydroxy-2-oxopropyl or 3-hydroxy-2-oxobutyl;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl, N-($C_3$–$C_6$-alkenyl)-N-($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methyl-but-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl, N-($C_3$–$C_6$-alkynyl)-N-($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$–$C_6$-alkanediyl: methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentane-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl;

$C_2$–$C_6$-alkenediyl: ethene-1,1-diyl, ethene-1,2-diyl, 1-propene-1,1-diyl, 1-propene-1,2-diyl, 1-propene-1,3-diyl, 2-propene-1,1-diyl, 2-propene-1,2-diyl, 2-propene-1,3-diyl, 1-butene-1,1-diyl, 1-butene-1,2-diyl, 1-butene-1,3-diyl, 1-butene-1,4-diyl, 2-butene-1,1-diyl, 2-butene-1,2-diyl, 2-butene-1,3-diyl, 2-butene-1,4-diyl, 3-butene-1,1-diyl, 3-butene-1,2-diyl, 3-butene-1,3-diyl, 3-butene-1,4-diyl, 1-methyl-1-propene-1,2-diyl, 1-methyl-1-propene-1,3-diyl, 1-methyl-2-propene-1,1-diyl, 1-methyl-2-propene-1,2-diyl, 1-methyl-2-propene-1,3-diyl, 2-methyl-1,1-propene-1,1-diyl, 2-methyl-1-propene-1,3-diyl, 3-butene-1,1-diyl, 3-butene-1,2-diyl, 3-butene-1,3-diyl, 3-butene-1,4-diyl, 1-pentene-1,1-diyl, 1-pentene-1,2-diyl, 1-pentene-1,3-diyl, 1-pentene-1,4-diyl, 1-pentene-1,5-diyl, 1-hexene-1,1-diyl, 1-hexene-1,2-diyl, 1-hexene-1,3-diyl, 1-hexene-1,4-diyl, 1-hexene-1,5-diyl or 1-hexene-1,6-diyl;

$C_2$–$C_6$-alkadienediyl: 1,3-butadiene-1,1-diyl, 1,3-butadiene-1,2-diyl, 1,3-butadiene-1,3-diyl, 1,3-butadiene-1,4-diyl, 1,3-pentadiene-1,1-diyl, 1,3-pentadiene-1,2-diyl, 1,3-pentadiene-1,3-diyl, 1,3-pentadiene-1,4-diyl, 1,3-pentadiene-1,5-diyl, 2,4-pentadiene-1,1-diyl, 2,4-pentadiene-1,2-diyl, 2,4-pentadiene-1,3-diyl, 2,4-pentadiene-1,4-diyl, 2,4-pentadiene-1,5-diyl, 1-methyl-1,3-butadiene-1,4-diyl, 1,3-hexadiene-1,1-diyl, 1,3-hexadiene-1,2-diyl, 1,3-hexadiene-1,3-diyl, 1,3-hexadiene-1,4-diyl, 1,3-hexadiene-1,5-diyl, 1,3-hexadiene-1,6-diyl, 1-methyl-1,3-pentadiene-1,2-diyl, 1-methyl-1,3-pentadiene-1,3-diyl, 1-methyl-1,3-pentadiene-1,4-diyl or 1-methyl-1,3-pentadiene-1,5-diyl;

$C_2$–$C_6$-alkynediyl: ethyne-1,2-diyl, 1-propyne-1,3-diyl, 2-propyne-1,1-diyl, 2-propyne-1,3-diyl, 1-butyne-1,3-diyl, 1-butyne-1,4-diyl, 2-butyne-1,1-diyl, 2-butyne-1,4-diyl, 1-methyl-2-propyne-1,1-diyl, 1-methyl-2-propyne-1,3-diyl, 1-pentyne-1,3-diyl, 1-pentyne-1,4-diyl, 1-pentyne-1,5-diyl, 2-pentyne-1,1-diyl, 2-pentyne-1,4-diyl, 2-pentyne-1,5-diyl, 3-pentyne-1,1-diyl, 3-pentyne-1,2-diyl, 3-pentyne-1,5-diyl, 4-pentyne-1,1-diyl, 4-pentyne-1,2-diyl, 4-pentyne-1,3-diyl, 4-pentyne-1,5-diyl, 1-hexyne-1,3-diyl, 1-hexyne-1,4-diyl, 1-hexyne-1,5-diyl, 1-hexyne-1,6-diyl, 2-hexyne-1,1-diyl, 2-hexyne-1,4-diyl, 2-hexyne-1,5-diyl, 2-hexyne-1,6-diyl, 3-hexyne-1,1-diyl, 3-hexyne-1,2-diyl, 3-hexyne-1,5-diyl, 3-hexyne-1,6-diyl, 4-hexyne-1,1-diyl, 4-hexyne-1,2-diyl, 4-hexyne-1,3-diyl, 4-hexyne-1,6-diyl, 5-hexyne-1,1-diyl, 5-hexyne-1,2-diyl, 5-hexyne-1,3-diyl, 5-hexyne-1,4-diyl or 5-hexyne-1,6-diyl;

$C_3$–$C_6$-cyclbalkyl, and the cycloalkyl moieties of $C_3$–$C_6$-cycloalkylamino and $C_3$–$C_6$-cycloalkylcarbonyl: for example cyclopropyl, cyclobutyl, cyclopentyl or cyclohexyl; heterocyclyl, and the heterocyclyl moieties of heterocyclyloxy, heterocyclylcarbonyl, heterocyclyl-$C_1$–$C_4$-alkyl, heterocyclyl-$C_1$–$C_6$-alkyl, heterocyclylsulfonyl or heterocyclyloxysulfonyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N-($C_1$–$C_6$-alkyl)-N-(heterocyclyl)aminocarbonyl, heterocyclylaminocarbonyl: a saturated, partially saturated or unsaturated 5- or 6-membered heterocyclic ring which contains one, two, three or four identical or different heteroatoms selected from the following group: oxygen, sulfur or nitrogen, i.e., for example, C-bonded 5-membered rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl, pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrookazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-3-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-triazol-4-yl, 1,2,4-triazol-3-yl, tetrazol-5-yl;

C-bonded 6-membered rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl, pyridin-4-yl, I,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yI, 1,2-dithian-3-yl, 1,2-dithian-4-yl, hexahydropyrimidin-2-yl hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yli tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl or 1,2,4,5-tetrazin-3-yl;

N-bonded 5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

N-bonded 6-membered rings such as:
piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholinyl), tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:
phthalimide, tetrahydrophthalimide, succinimide, maleimide, glutarimide, 5-oxotriazolin-1-yl, 5-oxo-1,3,4-oxadiazolin-4-yl or 2,4-dioxo(1H,3H)pyrimidin-3-yl;
where, if appropriate, the sulfur of the heterocycles mentioned may be oxidized to S=O or S(=O)$_2$
and where a bicyclic ring system may be formed with a fused-on phenyl ring or with a C$_3$–C$_6$-carbocycle or with a further 5- to 6-membered heterocycle.

All phenyl rings or heterocyclyl radicals and all phenyl components in phenoxy, phenylalkyl, phenylcarbonylalkyl, phenylcarbonyl, phenylalkenylcarbonyl, phenoxycarbonyl, phenyloxythiocarbonyl, phenylaminocarbonyl and N-alkyl-N-phenylaminocarbonyl, phenylsulfonyl or phenoxysulfonyl or heterocyclyl components in heterocyclyloxy, heterocyclylalkyl, heterocyclylcarbonylalkyl, heterocyclylcarbonyl, heterocyclyloxythiocarbonyl, heterocyclylalkenylcarbonyl, heterocyclyloxycarbonyl, heterocyclylaminocarbonyl, N-alkyl-N-heterocyclylaminocarbonyl, heterocyclylsulfonyl or heterocyclyloxysulfonyl are, unless stated otherwise, preferably unsubstituted, or they carry one, two or three halogen atoms and/or a nitro group, a cyano radical and/or one or two methyl, trifluoromethyl, methoxy or trifluoromethoxy substituents.

With regard to the use of the compounds of the formula I according to the invention as herbicides, the variables X, Y, R$^1$ to R$^{20}$ preferably have the following meanings, in each case on their own or in combination:

R$^1$ is hydrogen, halogen, C$_1$–C$_6$-alkyl, C$_1$–C$_6$-alkyloxy, C$_1$–C$_6$-alkylthio, C$_1$–C$_6$-alkylsulfinyl, C$_1$–C$_6$-alkylsulfonyl, C$_1$–C$_6$-haloalkyl, C$_1$–C$_6$-alkoxyalkyl, C$_1$–C$_6$-alkylsulfonyl-C$_1$–C$_6$-alkyl, particularly preferably methyl, chlorine, methoxy, methylthio, methylsulfinyl, methylsulfonyl, bromomethyl, methoxymethyl, methylsulfonylmethyl;

R$^2$ is hydrogen, halogen, for examplechlorine or bromine, C$_1$–C$_6$-alkyl, for example methyl;

X is C—R$^3$ where R$^3$ is as defined above, or is N;

Y is S, SO$_2$ or N—R$^4$ where R$^4$ is as defined above;

Hex is a radical of the formula IIa, where R$^8$, R$^9$, R$^{10}$, R$^{11}$ R$^{12}$, R$^{13}$ and R$^{14}$ are as defined above.

Preference is given, in particular, to compounds of the formula I where Y is O, S, SO$_2$ or N—R$^4$ and X is C—R$^3$. Preference is also given to compounds of the formula I where X is N and Y is S or N—R$^4$.

R$^8$, R$^9$, R$^{10}$, R$^{11}$, R$^{12}$, R$^{13}$ and R$^{14}$ are preferably as defined below:

R$^8$ is hydroxyl, halogen, mercapto, OR$^{15}$, SR$^{15}$, SO$_2$R$^{16}$, OSO$_2$R$^{16}$, NR$^{19}$R$^{20}$, ONR$^{19}$R$^{20}$ or N-bonded heterocyclyl which may be partially or fully halogenated and/or may carry one, two or three of the following radicals: nitro, cyano, C$_1$–C$_4$-alkyl, C$_1$–C$_4$-haloalkyl, C$_1$–C$_4$-alkoxy or C$_1$–C$_4$-haloalkoxy; in particular hydroxyl, OR$^{15}$, SR$^{15}$, N(OR$^{19}$)R$^{20}$; particularly preferably hydroxyl, C$_1$–C$_4$-alkyloxy, di-C$_1$–C$_4$-alkylamino, N-C$_1$–C$_4$-alkoxy-C$_1$–C$_4$-alkylamino, C$_1$–C$_4$-alkylthio, phenylthio, O—CH$_2$-phenyl, phenylcarbonyloxy, 2-, 3- or 4-fluorophenylcarbonyloxy, C$_1$–C$_4$-sulfonyloxy, phenylsulfonyloxy and 2-, 3- or 4-methylphenylsulfonyloxy;

R$^9$, R$^{13}$ are hydrogen or C$_1$–C$_4$-alkyl, such as methyl, ethyl or propyl; preferably hydrogen or methyl;

R$^{10}$, R$^{12}$, R$^{14}$ are hydrogen or C$_1$–C$_4$-alkyl, such as methyl, ethyl or propyl; preferably hydrogen or methyl;

R$^{11}$ is hydrogen, hydroxyl, C$_1$–C$_6$-alkyl, di(C$_1$–C$_6$-alkoxy)methyl, (C$_1$–C$_6$-alkoxy)(C$_1$–C$_6$-alkylthio)methyl, di(C$_1$–C$_6$-alkylthio)methyl, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl or C$_1$–C$_6$-haloalkylsulfonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one, two or three C$_1$–C$_4$-alkyl radicals;

preferably hydrogen, hydroxyl or C$_1$–C$_4$-alkyl, such as methyl, ethyl or propyl;

or

R$^{10}$ and R$^{12}$ or R$^{12}$ and R$^{14}$ together form a n bond or a C$_3$–C$_5$-alkyl chain which may carry one to three radicals selected from the following group: halogen, cyano, C$_1$–C$_4$-alkyl, C$_1$–C$_4$-haloalkyl or C$_1$–C$_4$-alkoxycarbonyl;

or

R$^{10}$ and R$^{14}$ or R$^9$ and R$^{13}$ together form a C$_1$–C$_4$-alkyl chain which may carry one to three radicals selected from the following group: halogen, cyano, C$_1$–C$_4$-alkyl, C$_1$–C$_4$-haloalkyl or C$_1$–C$_4$-alkoxycarbonyl;

or R$^{11}$ and R$^{12}$ together form a —O—(CH$_2$)$_p$—O—, —O—(CH$_2$)$_p$—S— or S—(CH$_2$)$_p$—S— chain which may be substituted by one to three radicals selected from the following group: halogen, cyano, C$_1$–C$_4$- alkyl, $C_1$–$C_4$-haloalkyl or $C_1$–$C_4$-alkoxycarbonyl; particularly preferably, $R^{20}$ and $R^{21}$ together form a —O—$(CH_2)_p$—O—, —O—$(CH_2)_p$—S— or —S—$(CH_2)_p$—S— chain which may be substituted by one to three radicals selected from the following groups: $C_1$–$C_4$-haloalkyl or $C_1$–$C_4$-alkoxycarbonyl;

or $R^{11}$ and $R^{12}$ together with the carbon to which they are attached form a carbonyl group. The variable p preferably represents 2 or 3 and the variable q preferably represents 2, 3 or 4.

Preferred meanings for $R^{15}$ to $R^{20}$ are:

$R^{15}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one to three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl or heterocyclyl-$C_1$–$C_6$-alkenylcarbonyl, where the phenyl or the heterocyclyl radical of the 14 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

is preferably $C_1$–$C_6$-alkyl, $C_3$–$C_6$-alkenyl, $C_3$–$C_6$-alkynyl, $C_1$–$C_6$-alkylcarbonyl, $C_1$–$C_6$-alkoxycarbonyl, $C_1$–$C_6$-alkylaminocarbonyl or N,N-di($C_1$–$C_6$-alkyl)aminocarbonyl, where the alkyl or alkoxy radicals mentioned may be partially or fully halogenated and/or may carry one to three of the following groups: cyano, $C_1$–$C_4$-alkoxy, $C_1$–$C_4$-alkylthio or $C_1$–$C_4$-alkoxycarbonyl;

is phenyl, phenyl-$C_1$–$C_6$-alkyl, phenylcarbonyl-$C_1$–$C_6$-alkyl, phenylcarbonyl, phenoxycarbonyl, heterocyclyl, heterocyclyl-$C_1$–$C_6$-alkyl, heterocyclylcarbonyl-$C_1$–$C_6$-alkyl, heterocyclylcarbonyl or heterocyclyloxycarbonyl, where the phenyl or the heterocyclyl radical of the 10 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{16}$ is $C_1$–$C_6$-alkyl, $C_3$–$C_6$-alkenyl or $C_3$–$C_6$-cycloalkyl, where the three radicals mentioned may be partially or fully halogenated and/or may carry one to three of the following groups: cyano, $C_1$–$C_4$-alkoxy, $C_1$–$C_4$-alkylthio, $C_1$–$C_4$-alkylcarbonyl or $C_1$–$C_4$-alkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{17}$, $R^{18}$ are hydroxyl, $C_1$–$C_6$-alkyl, $C_1$–$C_6$-alkoxy, phenyl, phenyl-$C_1$–$C_4$-alkyl or phenoxy, where the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di($C_1$–$C_6$-alkyl)amino, where the alkyl, cycloalkyl or alkoxy radicals mentioned may be partially or fully halogenated and/or may carry one to three of the following radicals: cyano, $C_1$–$C_4$-alkoxycarbonyl, $C_1$–$C_4$-alkylaminocarbonyl, di($C_1$–C4-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or-heterocyclyl radical of the six last-mentioned substituents may be, partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is $C_1$–$C_6$-alkyl or $C_3$–$C_6$-alkenyl.

Particular preference is given to compounds of the formula I where X is C—$R^3$ and $R^3$ is hydrogen, halogen, cyano, thiocyanato, $C_1$–$C_6$-alkyl, $C_1$–$C_6$-haloalkyl, $C_3$–$C_6$-cycloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxy-$C_1$–$C_6$-alkyl, is phenyl or pyridyl, where the two last-mentioned radicals may be partially or fully halogenated and/or may carry one, two or three, in particular one, of the following radicals: halogen, $C_1$–$C_4$-alkoxy, $C_1$–$C_4$-haloalkyl, and $C_1$–$C_4$-haloalkoxy;

or is COOR$^5$ where R$^5$ is as defined above. Here, R$^5$ is in particular hydrogen or $C_1$–$C_6$-alkyl and particularly preferably hydrogen, methyl, ethyl, n-propyl, isopropyl, n-butyl, 2-butyl, isobutyl and tert-butyl.

Preference is also given to the compounds of formula I where X is C—$R^3$ where $R^3$ is cyclopropyl or phenoxy which may be substituted as stated for phenyl.

Examples of preferred radicals $R^3$ are hydrogen, fluorine, chlorine, bromine, cyano, thiocyanato, methyl, ethyl, n-propyl, isopropyl, n-butyl, 2-butyl, isobutyl, tert-butyl, chloromethyl, dichloromethyl, trichloromethyl, fluoromethyl, difluoromethyl, trifluoromethyl, 2,2,2-trifluoroethyl, methoxymethyl, ethoxymethyl, methoxy, ethoxy, 1-propoxy, 2-propoxy, 1-butoxy, 2-butoxy, 2-methylprop-1-oxy, tert-butyloxy, difluoromethyloxy, trifluoromethyloxy, 2,2,2-trifluoroethyl-1-oxy, (methoxy)methyloxy, methylsulfanyl, ethylsulfanyl, n-propylsulfanyl, isopropylsulfanyl, 1-butylsulfanyl, 2-butylsulfanyl, 2-methylprop-1-ylsulfanyl, tert-butylsulfanyl, fluoromethylsulfanyl, trifluoromethylsulfanyl, 2,2,2-trifluoroethyl-1-sulfanyl, 2-(methylcarbonyl)ethyl, phenyl, phenoxy, 2-, 3- or 4-fluorophenyl, 2-, 3- or 4-chlorophenyl, 2-, 3- or-4-hydroxyphenyl, 2-, 3- or 4-methoxyphenyl, 2-, 3- or 4-(trifluoromethoxy)phenyl, 2-, 3- or 4-(difluoromethoxy)phenyl, 2-, 3- or 4-(trifluoromethyl)phenyl, 2-, 3- or 4-tolyl, 2-, 3- or 4-fluorophenoxy, 2-, 3- or 4-methoxyphenoxy, 2-, 3- or 4-trifluoromethylphenoxy, 2-, 3- or 4-chlorophenoxy, 2-, 3- or 4-pyridinyl, methoxycarbonyl, ethoxycarbonyl, trifluoromethoxycarbonyl, isopropoxycarbonyl, tert-butoxycarbonyl and phenoxycarbonyl.

Very particularly preferred compounds of the formula I where X=C—$R^3$ are those compounds where $R^3$ is hydrogen, halogen, in particular fluorine or chlorine, $C_1$–$C_4$-alkyl, $C_1$–$C_4$-haloalkyl, in particular fluoromethyl, difluoromethyl, trifluoromethyl and 2,2,2-trifluoroethyl, or phenyl where the phenyl radical may carry one, two or three, in particular one, substituent(s), selected from the group consisting of $C_1$–$C_4$-alkyl, in particular methyl, halogen, in particular fluorine or chlorine, $C_1$–$C_4$-alkoxy, in particular methoxy, or haloalkoxy, in particular trifluoromethoxy.

Among the cyclohexenone derivatives of the formula I mentioned above, particular preference is given to those compounds which are derived from benzothiazole-5-carboxylic acid, i.e. compounds of the formula I where X is a radical C—$R^3$ and Y is selected from the group consisting of S, SO and $SO_2$. In turn, among the cyclohexenone derivatives of benzothiazole preference is given to those where $R^3$ has one of the meanings mentioned above as being preferred. In particular, Y is S or $SO_2$.

Preference according to the invention is also given to those cyclohexenone derivatives which are derived from benzoxazole-5-carboxylic acid, i.e. compounds of the formula I where X is a group C—$R^3$ where $R^3$ is as defined above and Y is an oxygen atom. Among these, in turn, preference is given to those compounds where $R^3$ has the meanings given above as being preferred.

Preference is also given to cyclohexenone derivatives of the formula I which are derived from benzimidazole-5-carboxylic acid, i.e. compounds of the formula I where X is C—$R^3$ where $R^3$ is as defined above and Y is a group N—$R^4$ where $R^4$ is as defined above. Among these, preference is given to those benzimidazole derivatives of the formula I where $R^3$ has the meanings given above as being preferred for $R^3$. Furthermore, preference is given to benzimidazole derivatives of the formula I where $R^4$ is hydrogen, $C_1$–$C_6$-alkyl or $C_1$–$C_6$-haloalkyl, in particular hydrogen, methyl, ethyl, n-propyl or isopropyl.

Preference according to the invention is also given to cyclohexenone derivatives of benzotriazole-5-carboxylic acid, i.e. compounds of the formula I where X is nitrogen and Y is a group N—$R^4$ where $R^4$ is as defined above. Among these, in turn, preference is given to those compounds where $R^4$ has the meanings given above as being preferred.

Preference according to the invention is also given to cyclohexenone derivatives of benzothiadiazole-5-carboxylic acid, i.e. compounds of the formula I where X is N and Y is S. Preference is also given to pyrazole derivatives of benzoisothiadiazolecarboxylic acid, i.e. compounds of the formula I where X–Y is S=N and X is S.

Particular preference is given to the compounds of the formula I where $R^8$ is hydroxyl.

Likewise, particular preference is given to the compounds of the formula I where $R^8$ is halogen, $OR^{15}$, $SR^{15}$, $SO_2R^{16}$, $OSO_2R^{16}$, $NR^{19}R^{20}$, $N(OR^{19})R^{20}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Very particular preference is given to the compounds of the formula I where the variables in formula IIa or IIb are as defined below:

$R^9$, $R^{13}$ are hydrogen or $C_1$–$C_4$-alkyl;

$R^{10}$, $R^{12}$, $R^{14}$ are hydrogen or $C_1$–$C_4$-alkyl;

$R^{11}$ is hydrogen, hydroxyl, $C_1$–$C_6$-alkyl, in particular $C_1$–$C_4$-alkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkylthio, $C_1$–$C_6$-haloalkylthio, $C_1$–$C_6$-alkylsulfonyl or $C_1$–$C_6$-haloalkylsulfonyl; in particular hydrogen, hydroxyl or $C_1$–$C_6$-alkyl;

or $R^9$ and $R^{13}$ or $R^{10}$ and $R^{14}$ together form a $C_1$–$C_4$-alkyl chain which may carry one to three radicals selected from the following group: halogen, $C_1$–$C_4$-alkyl or $C_1$–$C_4$-haloalkyl; in particular, $R^{10}$ and $R^{14}$ together form a methylene or ethylene bridge which may carry one or two radicals selected from the following group: halogen, $C_1$–$C_2$-alkyl or $C_1$–$C_2$-haloalkyl;

or $R^{11}$ and $R^{12}$ together with the carbon to which they are attached form a carbonyl group.

Most preference is given to the compounds of the formula I where $R^9$, $R^{10}$, $R^{11}$, $R^{12}$, $R^{13}$ and $R^{14}$ independently of one another are hydrogen or $C_1$–$C_4$-alkyl, $R^{11}$ can also be hydroxyl, $C_1$–$C_4$-alkoxy, $C_1$–$C_4$-alkylthio, haloalkoxy or haloalkylthio, $R^{11}$ and $R^{12}$ together with the carbon atom to which they are attached may also be a carbonyl group, a 1,3-dioxolane, 1,3-dithiolane, 1,3-oxothiolane, 1,3-oxothiane, 1,3-dithiolane or a 1,3-dithiane ring, where the 2-position of the six rings mentioned is identical to the carbon atom to which $R^{11}$ and $R^{12}$ are attached, $R^9$ and $R^{13}$ or $R^{10}$ and $R^{14}$ may also be a $C_1$–$C_4$-alkylene chain, $R^{10}$ and $R^{12}$ or $R^{12}$ and $R^{13}$ together may form a π a bond.

Most preference is also given to the compounds of the formula I where $R^9$, $R^{13}$ are hydrogen or $C_1$–$C_4$-alkyl;

$R^{10}$, $R^{12}$, $R^{14}$ are hydrogen or $C_1$–$C_4$-alkyl;

$R^{11}$ is hydrogen, hydroxyl, $C_1$–$C_6$-alkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkylthio, $C_1$–$C_6$-haloalkylthio, $C_1$–$C_6$-alkylsulfonyl or $C_1$–$C_6$-haloalkylsulfonyl; in particular hydrogen, hydroxyl or $C_1$–$C_6$-alkyl;

where $R^{11}$ and $R^{12}$ together with the carbon to which they are attached may also form a carbonyl group.

Most preference is also given to the compounds in which hex is a radical of the formula IIa.

TABLE A

Particularly preferred combinations of $R^1$, $R^2$ and $R^3$

| | $R^3$ | $R^1$ | $R^2$ |
|---|---|---|---|
| 1 | H | $CH_3$ | $CH_3$ |
| 2 | F | $CH_3$ | $CH_3$ |
| 3 | Cl | $CH_3$ | $CH_3$ |
| 4 | Br | $CH_3$ | $CH_3$ |
| 5 | OH | $CH_3$ | $CH_3$ |
| 6 | SH | $CH_3$ | $CH_3$ |
| 7 | $NH_2$ | $CH_3$ | $CH_3$ |
| 8 | CN | $CH_3$ | $CH_3$ |
| 9 | $NO_2$ | $CH_3$ | $CH_3$ |
| 10 | SCN | $CH_3$ | $CH_3$ |
| 11 | $NH-NH_2$ | $CH_3$ | $CH_3$ |
| 12 | $CH_3$ | $CH_3$ | $CH_3$ |
| 13 | $C_2H_5$ | $CH_3$ | $CH_3$ |
| 14 | $n-C_3H_7$ | $CH_3$ | $CH_3$ |
| 15 | $i-C_3H_7$ | $CH_3$ | $CH_3$ |
| 16 | $n-C_4H_9$ | $CH_3$ | $CH_3$ |
| 17 | $s-C_4H_9$ | $CH_3$ | $CH_3$ |
| 18 | $i-C_4H_9$ | $CH_3$ | $CH_3$ |
| 19 | $t-C_4H_9$ | $CH_3$ | $CH_3$ |
| 20 | $CH_2Cl$ | $CH_3$ | $CH_3$ |
| 21 | $CHCl_2$ | $CH_3$ | $CH_3$ |
| 22 | $CCl_3$ | $CH_3$ | $CH_3$ |
| 23 | $CH_2F$ | $CH_3$ | $CH_3$ |
| 24 | $CHF_2$ | $CH_3$ | $CH_3$ |
| 25 | $CF_3$ | $CH_3$ | $CH_3$ |
| 62 | $CH_2CF_3$ | $CH_3$ | $CH_3$ |
| 27 | $CH_2OCH_3$ | $CH_3$ | $CH_3$ |
| 28 | $CH_2OCH_2CH_3$ | $CH_3$ | $CH_3$ |
| 29 | $CH_2NH_2$ | $CH_3$ | $CH_3$ |
| 30 | $OCH_3$ | $CH_3$ | $CH_3$ |
| 31 | $OC_2H_5$ | $CH_3$ | $CH_3$ |
| 32 | $O-n-C_3H_7$ | $CH_3$ | $CH_3$ |
| 33 | $O-i-C_3H_7$ | $CH_3$ | $CH_3$ |
| 34 | $O-n-C_4H_9$ | $CH_3$ | $CH_3$ |
| 35 | $O-s-C_4H_9$ | $CH_3$ | $CH_3$ |
| 36 | $O-i-C_4H_9$ | $CH_3$ | $CH_3$ |
| 37 | $O-t-C_4H_9$ | $CH_3$ | $CH_3$ |
| 38 | $OCHF_2$ | $CH_3$ | $CH_3$ |
| 39 | $OCF_3$ | $CH_3$ | $CH_3$ |
| 40 | $OCH_2CF_3$ | $CH_3$ | $CH_3$ |
| 41 | $OCH_2OCH_3$ | $CH_3$ | $CH_3$ |
| 42 | $SCH_3$ | $CH_3$ | $CH_3$ |
| 43 | $SC_2H_5$ | $CH_3$ | $CH_3$ |
| 44 | $S-n-C_3H_7$ | $CH_3$ | $CH_3$ |
| 45 | $S-i-C_3H_7$ | $CH_3$ | $CH_3$ |
| 46 | $S-n-C_4H_9$ | $CH_3$ | $CH_3$ |
| 47 | $S-s-C_4H_9$ | $CH_3$ | $CH_3$ |
| 48 | $S-i-C_4H_9$ | $CH_3$ | $CH_3$ |
| 49 | $S-t-C_4H_9$ | $CH_3$ | $CH_3$ |
| 50 | $SCHF_2$ | $CH_3$ | $CH_3$ |
| 51 | $SCF_3$ | $CH_3$ | $CH_3$ |
| 52 | $SCH_2CF_3$ | $CH_3$ | $CH_3$ |
| 53 | $SCH_2OCH_3$ | $CH_3$ | $CH_3$ |
| 54 | $NHCH_3$ | $CH_3$ | $CH_3$ |
| 55 | $NHC_2H_5$ | $CH_3$ | $CH_3$ |
| 56 | NH-phenyl | $CH_3$ | $CH_3$ |
| 57 | $N(CH_3)_2$ | $CH_3$ | $CH_3$ |
| 58 | $N(CH_2CH_3)_2$ | $CH_3$ | $CH_3$ |
| 59 | $N(phenyl)_2$ | $CH_3$ | $CH_3$ |
| 60 | $(CH_2)_2COCH_3$ | $CH_3$ | $CH_3$ |
| 61 | phenyl | $CH_3$ | $CH_3$ |
| 62 | 2-F-phenyl | $CH_3$ | $CH_3$ |
| 63 | 3-F-phenyl | $CH_3$ | $CH_3$ |
| 64 | 4-F-phenyl | $CH_3$ | $CH_3$ |
| 65 | 2-Cl-phenyl | $CH_3$ | $CH_3$ |
| 66 | 3-Cl-phenyl | $CH_3$ | $CH_3$ |
| 67 | 4-Cl-phenyl | $CH_3$ | $CH_3$ |
| 68 | 2-OH-phenyl | $CH_3$ | $CH_3$ |
| 69 | 3-OH-phenyl | $CH_3$ | $CH_3$ |
| 70 | 4-OH-phenyl | $CH_3$ | $CH_3$ |
| 71 | 2-$OCH_3$-phenyl | $CH_3$ | $CH_3$ |
| 72 | 3-$OCH_3$-phenyl | $CH_3$ | $CH_3$ |
| 73 | 4-$OCH_3$-phenyl | $CH_3$ | $CH_3$ |
| 74 | 2-$OCF_3$-phenyl | $CH_3$ | $CH_3$ |
| 75 | 3-$OCF_3$-phenyl | $CH_3$ | $CH_3$ |
| 76 | 4-$OCF_3$-phenyl | $CH_3$ | $CH_3$ |
| 77 | 2-$OCHF_2$-phenyl | $CH_3$ | $CH_3$ |
| 78 | 3-$OCHF_2$-phenyl | $CH_3$ | $CH_3$ |
| 79 | 4-$OCHF_2$-phenyl | $CH_3$ | $CH_3$ |
| 80 | 2-$CF_3$-phenyl | $CH_3$ | $CH_3$ |
| 81 | 3-$CF_3$-phenyl | $CH_3$ | $CH_3$ |
| 82 | 4-$CF_3$-phenyl | $CH_3$ | $CH_3$ |
| 83 | 2-$CH_3$-phenyl | $CH_3$ | $CH_3$ |
| 84 | 3-$CH_3$-phenyl | $CH_3$ | $CH_3$ |
| 85 | 4-$CH_3$-phenyl | $CH_3$ | $CH_3$ |
| 86 | 2-$NO_2$-phenyl | $CH_3$ | $CH_3$ |
| 87 | 3-$NO_2$-phenyl | $CH_3$ | $CH_3$ |
| 88 | 4-$NO_2$-phenyl | $CH_3$ | $CH_3$ |
| 89 | 2-pyridyl | $CH_3$ | $CH_3$ |
| 90 | 3-pyridyl | $CH_3$ | $CH_3$ |
| 91 | 4-pyridyl | $CH_3$ | $CH_3$ |
| 92 | 3'-$CH_3$-2-pyridyl | $CH_3$ | $CH_3$ |
| 93 | 4'-$CH_3$-2-pyridyl | $CH_3$ | $CH_3$ |
| 94 | 5'-$CH_3$-2-pyridyl | $CH_3$ | $CH_3$ |
| 95 | 6'-$CH_3$-2-pyridyl | $CH_3$ | $CH_3$ |
| 96 | 2'-$CH_3$-3-pyridyl | $CH_3$ | $CH_3$ |
| 97 | 4'-$CH_3$-3-pyridyl | $CH_3$ | $CH_3$ |
| 98 | 5'-$CH_3$-3-pyridyl | $CH_3$ | $CH_3$ |
| 99 | 6'-$CH_3$-3-pyridyl | $CH_3$ | $CH_3$ |
| 100 | 2'-$CH_3$-4-pyridyl | $CH_3$ | $CH_3$ |
| 101 | 3'-$CH_3$-4-pyridyl | $CH_3$ | $CH_3$ |
| 102 | 3'-Cl-2-pyridyl | $CH_3$ | $CH_3$ |
| 103 | 4'-Cl-2-pyridyl | $CH_3$ | $CH_3$ |
| 104 | 5'-Cl-2-pyridyl | $CH_3$ | $CH_3$ |
| 105 | 6'-Cl-2-pyridyl | $CH_3$ | $CH_3$ |
| 106 | 2'-Cl-3-pyridyl | $CH_3$ | $CH_3$ |
| 107 | 4'-Cl-3-pyridyl | $CH_3$ | $CH_3$ |
| 108 | 5'-Cl-3-pyridyl | $CH_3$ | $CH_3$ |
| 109 | 6'-Cl-3-pyridyl | $CH_3$ | $CH_3$ |
| 110 | 2'-Cl-4-pyridyl | $CH_3$ | $CH_3$ |
| 111 | 3'-Cl-4-pyridyl | $CH_3$ | $CH_3$ |
| 112 | cyclohexylamino | $CH_3$ | $CH_3$ |
| 113 | cyclopentylamino | $CH_3$ | $CH_3$ |
| 114 | morpholino | $CH_3$ | $CH_3$ |
| 115 | $CO_2H$ | $CH_3$ | $CH_3$ |
| 116 | $CO_2CH_3$ | $CH_3$ | $CH_3$ |
| 117 | $CO_2C_2H_5$ | $CH_3$ | $CH_3$ |
| 118 | $CO_2-n-C_3H_7$ | $CH_3$ | $CH_3$ |
| 119 | $CO_2-i-C_3H_7$ | $CH_3$ | $CH_3$ |
| 120 | $CO_2-n-C_4H_9$ | $CH_3$ | $CH_3$ |
| 121 | $CO_2-s-C_4H_9$ | $CH_3$ | $CH_3$ |
| 122 | $CO_2-i-C_4H_9$ | $CH_3$ | $CH_3$ |
| 123 | $CO_2-t-C_4H_9$ | $CH_3$ | $CH_3$ |
| 124 | $CO_2$-Ph | $CH_3$ | $CH_3$ |
| 125 | $CO_2$-3-pyridyl | $CH_3$ | $CH_3$ |
| 126 | $CONHCH_3$ | $CH_3$ | $CH_3$ |
| 127 | $CONHC_2H_5$ | $CH_3$ | $CH_3$ |
| 128 | CONHPh | $CH_3$ | $CH_3$ |
| 129 | $CON(CH_3)_2$ | $CH_3$ | $CH_3$ |
| 130 | $CON(CH_2CH_3)_2$ | $CH_3$ | $CH_3$ |
| 131 | $CON(phenyl)_2$ | $CH_3$ | $CH_3$ |
| 132 | H | $OCH_3$ | $CH_3$ |
| 133 | F | $OCH_3$ | $CH_3$ |
| 134 | Cl | $OCH_3$ | $CH_3$ |
| 135 | Br | $OCH_3$ | $CH_3$ |
| 136 | OH | $OCH_3$ | $CH_3$ |
| 137 | SH | $OCH_3$ | $CH_3$ |
| 138 | $NH_2$ | $OCH_3$ | $CH_3$ |
| 139 | CN | $OCH_3$ | $CH_3$ |
| 140 | $NO_2$ | $OCH_3$ | $CH_3$ |
| 141 | SCN | $OCH_3$ | $CH_3$ |
| 142 | $NH-NH_2$ | $OCH_3$ | $CH_3$ |
| 143 | $CH_3$ | $OCH_3$ | $CH_3$ |
| 144 | $C_2H_5$ | $OCH_3$ | $CH_3$ |
| 145 | $n-C_3H_7$ | $OCH_3$ | $CH_3$ |
| 146 | $i-C_3H_7$ | $OCH_3$ | $CH_3$ |
| 147 | $n-C_4H_9$ | $OCH_3$ | $CH_3$ |
| 148 | $s-C_4H_9$ | $OCH_3$ | $CH_3$ |
| 149 | $i-C_4H_9$ | $OCH_3$ | $CH_3$ |
| 150 | $t-C_4H_9$ | $OCH_3$ | $CH_3$ |

TABLE A-continued

Particularly preferred combinations of $R^1$, $R^2$ and $R^3$

| | $R^3$ | $R^1$ | $R^2$ |
|---|---|---|---|
| 151 | $CH_2Cl$ | $OCH_3$ | $CH_3$ |
| 152 | $CHCl_2$ | $OCH_3$ | $CH_3$ |
| 153 | $CCl_3$ | $OCH_3$ | $CH_3$ |
| 154 | $CH_2F$ | $OCH_3$ | $CH_3$ |
| 155 | $CHF_2$ | $OCH_3$ | $CH_3$ |
| 156 | $CF_3$ | $OCH_3$ | $CH_3$ |
| 157 | $CH_2CF_3$ | $OCH_3$ | $CH_3$ |
| 158 | $CH_2OCH_3$ | $OCH_3$ | $CH_3$ |
| 159 | $CH_2OCH_2CH_3$ | $OCH_3$ | $CH_3$ |
| 160 | $CH_2NH_2$ | $OCH_3$ | $CH_3$ |
| 161 | $OCH_3$ | $OCH_3$ | $CH_3$ |
| 162 | $OC_2H_5$ | $OCH_3$ | $CH_3$ |
| 163 | $O-n-C_3H_7$ | $OCH_3$ | $CH_3$ |
| 164 | $O-i-C_3H_7$ | $OCH_3$ | $CH_3$ |
| 165 | $O-n-C_4H_9$ | $OCH_3$ | $CH_3$ |
| 166 | $O-s-C_4H_9$ | $OCH_3$ | $CH_3$ |
| 167 | $O-i-C_4H_9$ | $OCH_3$ | $CH_3$ |
| 168 | $O-t-C_4H_9$ | $OCH_3$ | $CH_3$ |
| 169 | $OCHF_2$ | $OCH_3$ | $CH_3$ |
| 170 | $OCF_3$ | $OCH_3$ | $CH_3$ |
| 171 | $OCH_2CF_3$ | $OCH_3$ | $CH_3$ |
| 172 | $OCH_2OCH_3$ | $OCH_3$ | $CH_3$ |
| 173 | $SCH_3$ | $OCH_3$ | $CH_3$ |
| 174 | $SC_2H_5$ | $OCH_3$ | $CH_3$ |
| 175 | $S-n-C_3H_7$ | $OCH_3$ | $CH_3$ |
| 176 | $S-i-C_3H_7$ | $OCH_3$ | $CH_3$ |
| 177 | $S-n-C_4H_9$ | $OCH_3$ | $CH_3$ |
| 178 | $S-s-C_4H_9$ | $OCH_3$ | $CH_3$ |
| 179 | $S-i-C_4H_9$ | $OCH_3$ | $CH_3$ |
| 180 | $S-t-C_4H_9$ | $OCH_3$ | $CH_3$ |
| 181 | $SCHF_2$ | $OCH_3$ | $CH_3$ |
| 182 | $SCF_3$ | $OCH_3$ | $CH_3$ |
| 183 | $SCH_2CF_3$ | $OCH_3$ | $CH_3$ |
| 184 | $SCH_2OCH_3$ | $OCH_3$ | $CH_3$ |
| 185 | $NHCH_3$ | $OCH_3$ | $CH_3$ |
| 186 | $NHC_2H_5$ | $OCH_3$ | $CH_3$ |
| 187 | NHphenyl | $OCH_3$ | $CH_3$ |
| 188 | $N(CH_3)_2$ | $OCH_3$ | $CH_3$ |
| 189 | $N(CH_2CH_3)_2$ | $OCH_3$ | $CH_3$ |
| 190 | $N(phenyl)_2$ | $OCH_3$ | $CH_3$ |
| 191 | $(CH_2)_2COCH_3$ | $OCH_3$ | $CH_3$ |
| 192 | phenyl | $OCH_3$ | $CH_3$ |
| 193 | 2-F-phenyl | $OCH_3$ | $CH_3$ |
| 194 | 3-F-phenyl | $OCH_3$ | $CH_3$ |
| 195 | 4-F-phenyl | $OCH_3$ | $CH_3$ |
| 196 | 2-Cl-phenyl | $OCH_3$ | $CH_3$ |
| 197 | 3-Cl-phenyl | $OCH_3$ | $CH_3$ |
| 198 | 4-Cl-phenyl | $OCH_3$ | $CH_3$ |
| 199 | 2-OH-phenyl | $OCH_3$ | $CH_3$ |
| 200 | 3-OH-phenyl | $OCH_3$ | $CH_3$ |
| 201 | 4-OH-phenyl | $OCH_3$ | $CH_3$ |
| 202 | 2-$OCH_3$-phenyl | $OCH_3$ | $CH_3$ |
| 203 | 3-$OCH_3$-phenyl | $OCH_3$ | $CH_3$ |
| 204 | 4-$OCH_3$-phenyl | $OCH_3$ | $CH_3$ |
| 205 | 2-$OCF_3$-phenyl | $OCH_3$ | $CH_3$ |
| 206 | 3-$OCF_3$-phenyl | $OCH_3$ | $CH_3$ |
| 207 | 4-$OCF_3$-phenyl | $OCH_3$ | $CH_3$ |
| 208 | 2-$OCHF_2$-phenyl | $OCH_3$ | $CH_3$ |
| 209 | 3-$OCHF_2$-phenyl | $OCH_3$ | $CH_3$ |
| 210 | 4-$OCHF_2$-phenyl | $OCH_3$ | $CH_3$ |
| 211 | 2-$CF_3$-phenyl | $OCH_3$ | $CH_3$ |
| 212 | 3-$CF_3$-phenyl | $OCH_3$ | $CH_3$ |
| 213 | 4-$CF_3$-phenyl | $OCH_3$ | $CH_3$ |
| 214 | 2-$CH_3$-phenyl | $OCH_3$ | $CH_3$ |
| 215 | 3-$CH_3$-phenyl | $OCH_3$ | $CH_3$ |
| 216 | 4-$CH_3$-phenyl | $OCH_3$ | $CH_3$ |
| 217 | 2-$NO_2$-phenyl | $OCH_3$ | $CH_3$ |
| 218 | 3-$NO_2$-phenyl | $OCH_3$ | $CH_3$ |
| 219 | 4-$NO_2$-phenyl | $OCH_3$ | $CH_3$ |
| 220 | 2-pyridyl | $OCH_3$ | $CH_3$ |
| 221 | 3-pyridyl | $OCH_3$ | $CH_3$ |
| 222 | 4-pyridyl | $OCH_3$ | $CH_3$ |
| 223 | 3'-$CH_3$-2-pyridyl | $OCH_3$ | $CH_3$ |
| 224 | 4'-$CH_3$-2-pyridyl | $OCH_3$ | $CH_3$ |
| 225 | 5'-$CH_3$-2-pyridyl | $OCH_3$ | $CH_3$ |
| 226 | 6'-$CH_3$-2-pyridyl | $OCH_3$ | $CH_3$ |
| 227 | 2'-$CH_3$-3-pyridyl | $OCH_3$ | $CH_3$ |
| 228 | 4'-$CH_3$-3-pyridyl | $OCH_3$ | $CH_3$ |
| 229 | 5'-$CH_3$-3-pyridyl | $OCH_3$ | $CH_3$ |
| 230 | 6'-$CH_3$-3-pyridyl | $OCH_3$ | $CH_3$ |
| 231 | 2'-$CH_3$-4-pyridyl | $OCH_3$ | $CH_3$ |
| 232 | 3'-$CH_3$-4-pyridyl | $OCH_3$ | $CH_3$ |
| 233 | 3'-Cl-2-pyridyl | $OCH_3$ | $CH_3$ |
| 234 | 4'-Cl-2-pyridyl | $OCH_3$ | $CH_3$ |
| 235 | 5'-Cl-2-pyridyl | $OCH_3$ | $CH_3$ |
| 236 | 6'-Cl-2-pyridyl | $OCH_3$ | $CH_3$ |
| 237 | 2'-Cl-3-pyridyl | $OCH_3$ | $CH_3$ |
| 238 | 4'-Cl-3-pyridyl | $OCH_3$ | $CH_3$ |
| 239 | 5'-Cl-3-pyridyl | $OCH_3$ | $CH_3$ |
| 240 | 6'-Cl-3-pyridyl | $OCH_3$ | $CH_3$ |
| 241 | 2'-Cl-4-pyridyl | $OCH_3$ | $CH_3$ |
| 242 | 3'-Cl-4-pyridyl | $OCH_3$ | $CH_3$ |
| 243 | cyclohexylamino | $OCH_3$ | $CH_3$ |
| 244 | cyclopentylamino | $OCH_3$ | $CH_3$ |
| 245 | morpholino | $OCH_3$ | $CH_3$ |
| 246 | $CO_2H$ | $OCH_3$ | $CH_3$ |
| 247 | $CO_2CH_3$ | $OCH_3$ | $CH_3$ |
| 248 | $CO_2C_2H_5$ | $OCH_3$ | $CH_3$ |
| 249 | $CO_2$-n-$C_3H_7$ | $OCH_3$ | $CH_3$ |
| 250 | $CO_2$-i-$C_3H_7$ | $OCH_3$ | $CH_3$ |
| 251 | $CO_2$-n-$C_4H_9$ | $OCH_3$ | $CH_3$ |
| 252 | $CO_2$-s-$C_4H_9$ | $OCH_3$ | $CH_3$ |
| 253 | $CO_2$-i-$C_4H_9$ | $OCH_3$ | $CH_3$ |
| 254 | $CO_2$-t-$C_4H_9$ | $OCH_3$ | $CH_3$ |
| 255 | $CO_2$-Ph | $OCH_3$ | $CH_3$ |
| 256 | $CO_2$-3-pyridyl | $OCH_3$ | $CH_3$ |
| 257 | $CONHCH_3$ | $OCH_3$ | $CH_3$ |
| 258 | $CONHC_2H_5$ | $OCH_3$ | $CH_3$ |
| 259 | CONHphenyl | $OCH_3$ | $CH_3$ |
| 260 | $CON(CH_3)_2$ | $OCH_3$ | $CH_3$ |
| 261 | $CON(CH_2CH_3)_2$ | $OCH_3$ | $CH_3$ |
| 262 | $CON(phenyl)_2$ | $OCH_3$ | $CH_3$ |
| 263 | H | Cl | $CH_3$ |
| 264 | F | Cl | $CH_3$ |
| 265 | Cl | Cl | $CH_3$ |
| 266 | Br | Cl | $CH_3$ |
| 267 | OH | Cl | $CH_3$ |
| 268 | SH | Cl | $CH_3$ |
| 269 | $NH_2$ | Cl | $CH_3$ |
| 270 | CN | Cl | $CH_3$ |
| 271 | $NO_2$ | Cl | $CH_3$ |
| 272 | SCN | Cl | $CH_3$ |
| 273 | NH—$NH_2$ | Cl | $CH_3$ |
| 274 | $CH_3$ | Cl | $CH_3$ |
| 275 | $C_2H_5$ | Cl | $CH_3$ |
| 276 | n-$C_3H_7$ | Cl | $CH_3$ |
| 277 | i-$C_3H_7$ | Cl | $CH_3$ |
| 278 | n-$C_4H_9$ | Cl | $CH_3$ |
| 279 | s-$C_4H_9$ | Cl | $CH_3$ |
| 280 | i-$C_4H_9$ | Cl | $CH_3$ |
| 281 | t-$C_4H_9$ | Cl | $CH_3$ |
| 282 | $CH_2Cl$ | Cl | $CH_3$ |
| 283 | $CHCl_2$ | Cl | $CH_3$ |
| 284 | $CCl_3$ | Cl | $CH_3$ |
| 285 | $CH_2F$ | Cl | $CH_3$ |
| 286 | $CHF_2$ | Cl | $CH_3$ |
| 287 | $CF_3$ | Cl | $CH_3$ |
| 288 | $CH_2CF_3$ | Cl | $CH_3$ |
| 289 | $CH_2OCH_3$ | Cl | $CH_3$ |
| 290 | $CH_2OCH_2CH_3$ | Cl | $CH_3$ |
| 291 | $CH_2NH_2$ | Cl | $CH_3$ |
| 292 | $OCH_3$ | Cl | $CH_3$ |
| 293 | $OC_2H_5$ | Cl | $CH_3$ |
| 294 | $O-n-C_3H_7$ | Cl | $CH_3$ |
| 295 | $O-i-C_3H_7$ | Cl | $CH_3$ |
| 296 | $O-n-C_4H_9$ | Cl | $CH_3$ |
| 297 | $O-s-C_4H_9$ | Cl | $CH_3$ |
| 298 | $O-i-C_4H_9$ | Cl | $CH_3$ |
| 299 | $O-t-C_4H_9$ | Cl | $CH_3$ |
| 300 | $OCHF_2$ | Cl | $CH_3$ |

TABLE A-continued

Particularly preferred combinations of $R^1$, $R^2$ and $R^3$

| | $R^3$ | $R^1$ | $R^2$ |
|---|---|---|---|
| 301 | $OCF_3$ | Cl | $CH_3$ |
| 302 | $OCH_2CF_3$ | Cl | $CH_3$ |
| 303 | $OCH_2OCH_3$ | Cl | $CH_3$ |
| 304 | $SCH_3$ | Cl | $CH_3$ |
| 305 | $SC_2H_5$ | Cl | $CH_3$ |
| 306 | $S\text{-}n\text{-}C_3H_7$ | Cl | $CH_3$ |
| 307 | $S\text{-}i\text{-}C_3H_7$ | Cl | $CH_3$ |
| 308 | $S\text{-}n\text{-}C_4H_9$ | Cl | $CH_3$ |
| 309 | $S\text{-}s\text{-}C_4H_9$ | Cl | $CH_3$ |
| 310 | $S\text{-}i\text{-}C_4H_9$ | Cl | $CH_3$ |
| 311 | $S\text{-}t\text{-}C_4H_9$ | Cl | $CH_3$ |
| 312 | $SCHF_2$ | Cl | $CH_3$ |
| 313 | $SCF_3$ | Cl | $CH_3$ |
| 314 | $SCH_2CF_3$ | Cl | $CH_3$ |
| 315 | $SCH_2OCH_3$ | Cl | $CH_3$ |
| 316 | $NHCH_3$ | Cl | $CH_3$ |
| 317 | $NHC_2H_5$ | Cl | $CH_3$ |
| 318 | NH-phenyl | Cl | $CH_3$ |
| 319 | $N(CH_3)_2$ | Cl | $CH_3$ |
| 320 | $N(CH_2CH_3)_2$ | Cl | $CH_3$ |
| 321 | $N(phenyl)_2$ | Cl | $CH_3$ |
| 322 | $(CH_2)_2COCH_3$ | Cl | $CH_3$ |
| 323 | phenyl | Cl | $CH_3$ |
| 324 | 2-F-phenyl | Cl | $CH_3$ |
| 325 | 3-F-phenyl | Cl | $CH_3$ |
| 362 | 4-F-phenyl | Cl | $CH_3$ |
| 327 | 2-Cl-phenyl | Cl | $CH_3$ |
| 328 | 3-Cl-phenyl | Cl | $CH_3$ |
| 329 | 4-Cl-phenyl | Cl | $CH_3$ |
| 330 | 2-OH-phenyl | Cl | $CH_3$ |
| 331 | 3-OH-phenyl | Cl | $CH_3$ |
| 332 | 4-OH-phenyl | Cl | $CH_3$ |
| 333 | $2\text{-}OCH_3\text{-phenyl}$ | Cl | $CH_3$ |
| 334 | $3\text{-}OCH_3\text{-phenyl}$ | Cl | $CH_3$ |
| 335 | $4\text{-}OCH_3\text{-phenyl}$ | Cl | $CH_3$ |
| 336 | $2\text{-}OCF_3\text{-phenyl}$ | Cl | $CH_3$ |
| 337 | $3\text{-}OCF_3\text{-phenyl}$ | Cl | $CH_3$ |
| 338 | $4\text{-}OCF_3\text{-phenyl}$ | Cl | $CH_3$ |
| 339 | $2\text{-}OCHF_2\text{-phenyl}$ | Cl | $CH_3$ |
| 340 | $3\text{-}OCHF_2\text{-phenyl}$ | Cl | $CH_3$ |
| 341 | $4\text{-}OCHF_2\text{-phenyl}$ | Cl | $CH_3$ |
| 342 | $2\text{-}CF_3\text{-phenyl}$ | Cl | $CH_3$ |
| 343 | $3\text{-}CF_3\text{-phenyl}$ | Cl | $CH_3$ |
| 344 | $4\text{-}CF_3\text{-phenyl}$ | Cl | $CH_3$ |
| 345 | $2\text{-}CH_3\text{-phenyl}$ | Cl | $CH_3$ |
| 346 | $3\text{-}CH_3\text{-phenyl}$ | Cl | $CH_3$ |
| 347 | $4\text{-}CH_3\text{-phenyl}$ | Cl | $CH_3$ |
| 348 | $2\text{-}NO_2\text{-phenyl}$ | Cl | $CH_3$ |
| 349 | $3\text{-}NO_2\text{-phenyl}$ | Cl | $CH_3$ |
| 350 | $4\text{-}NO_2\text{-phenyl}$ | Cl | $CH_3$ |
| 351 | 2-pyridyl | Cl | $CH_3$ |
| 352 | 3-pyridyl | Cl | $CH_3$ |
| 353 | 4-pyridyl | Cl | $CH_3$ |
| 354 | $3'\text{-}CH_3\text{-2-pyridyl}$ | Cl | $CH_3$ |
| 355 | $4'\text{-}CH_3\text{-2-pyridyl}$ | Cl | $CH_3$ |
| 356 | $5'\text{-}CH_3\text{-2-pyridyl}$ | Cl | $CH_3$ |
| 357 | $6'\text{-}CH_3\text{-2-pyridyl}$ | Cl | $CH_3$ |
| 358 | $2'\text{-}CH_3\text{-3-pyridyl}$ | Cl | $CH_3$ |
| 359 | $4'\text{-}CH_3\text{-3-pyridyl}$ | Cl | $CH_3$ |
| 360 | $5'\text{-}CH_3\text{-3-pyridyl}$ | Cl | $CH_3$ |
| 361 | $6'\text{-}CH_3\text{-3-pyridyl}$ | Cl | $CH_3$ |
| 362 | $2'\text{-}CH_3\text{-4-pyridyl}$ | Cl | $CH_3$ |
| 363 | $3'\text{-}CH_3\text{-4-pyridyl}$ | Cl | $CH_3$ |
| 364 | 3'-Cl-2-pyridyl | Cl | $CH_3$ |
| 365 | 4'-Cl-2-pyridyl | Cl | $CH_3$ |
| 366 | 5'-Cl-2-pyridyl | Cl | $CH_3$ |
| 367 | 6'-Cl-2-pyridyl | Cl | $CH_3$ |
| 368 | 2'-Cl-3-pyridyl | Cl | $CH_3$ |
| 369 | 4'-Cl-3-pyridyl | Cl | $CH_3$ |
| 370 | 5'-Cl-3-pyridyl | Cl | $CH_3$ |
| 371 | 6'-Cl-3-pyridyl | Cl | $CH_3$ |
| 372 | 2'-Cl-4-pyridyl | Cl | $CH_3$ |
| 373 | 3'-Cl-4-pyridyl | Cl | $CH_3$ |
| 374 | cyclohexylamino | Cl | $CH_3$ |
| 375 | cyclopentylamino | Cl | $CH_3$ |
| 376 | morpholino | Cl | $CH_3$ |
| 377 | $CO_2H$ | Cl | $CH_3$ |
| 378 | $CO_2CH_3$ | Cl | $CH_3$ |
| 379 | $CO_2C_2H_5$ | Cl | $CH_3$ |
| 380 | $CO_2\text{-}n\text{-}C_3H_7$ | Cl | $CH_3$ |
| 381 | $CO_2\text{-}i\text{-}C_3H_7$ | Cl | $CH_3$ |
| 382 | $CO_2\text{-}n\text{-}C_4H_9$ | Cl | $CH_3$ |
| 383 | $CO_2\text{-}s\text{-}C_4H_9$ | Cl | $CH_3$ |
| 384 | $CO_2\text{-}i\text{-}C_4H_9$ | Cl | $CH_3$ |
| 385 | $CO_2\text{-}t\text{-}C_4H_9$ | Cl | $CH_3$ |
| 386 | $CO_2$-phenyl | Cl | $CH_3$ |
| 387 | $CO_2$-3-pyridyl | Cl | $CH_3$ |
| 388 | $CONHCH_3$ | Cl | $CH_3$ |
| 389 | $CONHC_2H_5$ | Cl | $CH_3$ |
| 390 | CONH-phenyl | Cl | $CH_3$ |
| 391 | $CON(CH_3)_2$ | Cl | $CH_3$ |
| 392 | $CON(CH_2CH_3)_2$ | Cl | $CH_3$ |
| 393 | $CON(phenyl)_2$ | Cl | $CH_3$ |
| 394 | H | $CH_3$ | H |
| 394 | F | $CH_3$ | H |
| 396 | Cl | $CH_3$ | H |
| 397 | Br | $CH_3$ | H |
| 398 | OH | $CH_3$ | H |
| 399 | SH | $CH_3$ | H |
| 400 | $NH_2$ | $CH_3$ | H |
| 401 | CN | $CH_3$ | H |
| 402 | $NO_2$ | $CH_3$ | H |
| 403 | SCN | $CH_3$ | H |
| 404 | $NH{-}NH_2$ | $CH_3$ | H |
| 405 | $CH_3$ | $CH_3$ | H |
| 406 | $C_2H_5$ | $CH_3$ | H |
| 407 | $n\text{-}C_3H_7$ | $CH_3$ | H |
| 408 | $i\text{-}C_3H_7$ | $CH_3$ | H |
| 049 | $n\text{-}C_4H_9$ | $CH_3$ | H |
| 410 | $s\text{-}C_4H_9$ | $CH_3$ | H |
| 411 | $i\text{-}C_4H_9$ | $CH_3$ | H |
| 412 | $t\text{-}C_4H_9$ | $CH_3$ | H |
| 413 | $CH_2Cl$ | $CH_3$ | H |
| 414 | $CHCl_2$ | $CH_3$ | H |
| 415 | $CCl_3$ | $CH_3$ | H |
| 416 | $CH_2F$ | $CH_3$ | H |
| 417 | $CHF_2$ | $CH_3$ | H |
| 418 | $CF_3$ | $CH_3$ | H |
| 419 | $CH_2CF_3$ | $CH_3$ | H |
| 420 | $CH_2OCH_3$ | $CH_3$ | H |
| 421 | $CH_2OCH_2CH_3$ | $CH_3$ | H |
| 422 | $CH_2NH_2$ | $CH_3$ | H |
| 423 | $OCH_3$ | $CH_3$ | H |
| 424 | $OC_2H_5$ | $CH_3$ | H |
| 425 | $O\text{-}n\text{-}C_3H_7$ | $CH_3$ | H |
| 462 | $O\text{-}i\text{-}C_3H_7$ | $CH_3$ | H |
| 427 | $O\text{-}n\text{-}C_4H_9$ | $CH_3$ | H |
| 428 | $O\text{-}s\text{-}C_4H_9$ | $CH_3$ | H |
| 429 | $O\text{-}i\text{-}C_4H_9$ | $CH_3$ | H |
| 430 | $O\text{-}t\text{-}C_4H_9$ | $CH_3$ | H |
| 431 | $OCHF_2$ | $CH_3$ | H |
| 432 | $OCF_3$ | $CH_3$ | H |
| 433 | $OCH_2CF_3$ | $CH_3$ | H |
| 434 | $OCH_2OCH_3$ | $CH_3$ | H |
| 435 | $SCH_3$ | $CH_3$ | H |
| 436 | $SC_2H_5$ | $CH_3$ | H |
| 437 | $S\text{-}n\text{-}C_3H_7$ | $CH_3$ | H |
| 438 | $S\text{-}i\text{-}C_3H_7$ | $CH_3$ | H |
| 439 | $S\text{-}n\text{-}C_4H_9$ | $CH_3$ | H |
| 440 | $S\text{-}s\text{-}C_4H_9$ | $CH_3$ | H |
| 441 | $S\text{-}i\text{-}C_4H_9$ | $CH_3$ | H |
| 442 | $S\text{-}t\text{-}C_4H_9$ | $CH_3$ | H |
| 443 | $SCHF_2$ | $CH_3$ | H |
| 444 | $SCF_3$ | $CH_3$ | H |
| 445 | $SCH_2CF_3$ | $CH_3$ | H |
| 446 | $SCH_2OCH_3$ | $CH_3$ | H |
| 447 | $NHCH_3$ | $CH_3$ | H |
| 448 | $NHC_2H_5$ | $CH_3$ | H |
| 449 | NH-phenyl | $CH_3$ | H |
| 450 | $N(CH_3)_2$ | $CH_3$ | H |

TABLE A-continued

Particularly preferred combinations of $R^1$, $R^2$ and $R^3$

| | $R^3$ | $R^1$ | $R^2$ |
|---|---|---|---|
| 451 | $N(CH_2CH_3)_2$ | $CH_3$ | H |
| 452 | $N(phenyl)_2$ | $CH_3$ | H |
| 453 | $(CH_2)_2COCH_3$ | $CH_3$ | H |
| 454 | phenyl | $CH_3$ | H |
| 455 | 2-F-phenyl | $CH_3$ | H |
| 456 | 3-F-phenyl | $CH_3$ | H |
| 457 | 4-F-phenyl | $CH_3$ | H |
| 458 | 2-Cl-phenyl | $CH_3$ | H |
| 459 | 3-Cl-phenyl | $CH_3$ | H |
| 460 | 4-Cl-phenyl | $CH_3$ | H |
| 461 | 2-OH-phenyl | $CH_3$ | H |
| 462 | 3-OH-phenyl | $CH_3$ | H |
| 463 | 4-OH-phenyl | $CH_3$ | H |
| 464 | 2-$OCH_3$-phenyl | $CH_3$ | H |
| 465 | 3-$OCH_3$-phenyl | $CH_3$ | H |
| 466 | 4-$OCH_3$-phenyl | $CH_3$ | H |
| 467 | 2-$OCF_3$-phenyl | $CH_3$ | H |
| 468 | 3-$OCF_3$-phenyl | $CH_3$ | H |
| 469 | 4-$OCF_3$-phenyl | $CH_3$ | H |
| 470 | 2-$OCHF_2$-phenyl | $CH_3$ | H |
| 471 | 3-$OCHF_2$-phenyl | $CH_3$ | H |
| 472 | 4-$OCHF_2$-phenyl | $CH_3$ | H |
| 473 | 2-$CF_3$-phenyl | $CH_3$ | H |
| 474 | 3-$CF_3$-phenyl | $CH_3$ | H |
| 475 | 4-$CF_3$-phenyl | $CH_3$ | H |
| 476 | 2-$CH_3$-phenyl | $CH_3$ | H |
| 477 | 3-$CH_3$-phenyl | $CH_3$ | H |
| 478 | 4-$CH_3$-phenyl | $CH_3$ | H |
| 479 | 2-$NO_2$-phenyl | $CH_3$ | H |
| 480 | 3-$NO_2$-phenyl | $CH_3$ | H |
| 481 | 4-$NO_2$-phenyl | $CH_3$ | H |
| 482 | 2-pyridyl | $CH_3$ | H |
| 483 | 3-pyridyl | $CH_3$ | H |
| 484 | 4-pyridyl | $CH_3$ | H |
| 485 | 3'-$CH_3$-2-pyridyl | $CH_3$ | H |
| 486 | 4'-$CH_3$-2-pyridyl | $CH_3$ | H |
| 487 | 5'-$CH_3$-2-pyridyl | $CH_3$ | H |
| 488 | 6'-$CH_3$-2-pyridyl | $CH_3$ | H |
| 489 | 2'-$CH_3$-3-pyridyl | $CH_3$ | H |
| 490 | 4'-$CH_3$-3-pyridyl | $CH_3$ | H |
| 491 | 5'-$CH_3$-3-pyridyl | $CH_3$ | H |
| 492 | 6'-$CH_3$-3-pyridyl | $CH_3$ | H |
| 493 | 2'-$CH_3$-4-pyridyl | $CH_3$ | H |
| 494 | 3'-$CH_3$-4-pyridyl | $CH_3$ | H |
| 495 | 3'-Cl-2-pyridyl | $CH_3$ | H |
| 496 | 4'-Cl-2-pyridyl | $CH_3$ | H |
| 497 | 5'-Cl-2-pyridyl | $CH_3$ | H |
| 498 | 6'-Cl-2-pyridyl | $CH_3$ | H |
| 499 | 2'-Cl-3-pyridyl | $CH_3$ | H |
| 500 | 4'-Cl-3-pyridyl | $CH_3$ | H |
| 501 | 5'-Cl-3-pyridyl | $CH_3$ | H |
| 502 | 6'-Cl-3-pyridyl | $CH_3$ | H |
| 503 | 2'-Cl-4-pyridyl | $CH_3$ | H |
| 504 | 3'-Cl-4-pyridyl | $CH_3$ | H |
| 505 | cyclohexylamino | $CH_3$ | H |
| 506 | cyclopentylamino | $CH_3$ | H |
| 507 | morpholino | $CH_3$ | H |
| 508 | $CO_2H$ | $CH_3$ | H |
| 509 | $CO_2CH_3$ | $CH_3$ | H |
| 510 | $CO_2C_2H_5$ | $CH_3$ | H |
| 511 | $CO_2$-n-$C_3H_7$ | $CH_3$ | H |
| 512 | $CO_2$-i-$C_3H_7$ | $CH_3$ | H |
| 513 | $CO_2$-n-$C_4H_9$ | $CH_3$ | H |
| 514 | $CO_2$-s-$C_4H_9$ | $CH_3$ | H |
| 515 | $CO_2$-i-$C_4H_9$ | $CH_3$ | H |
| 516 | $CO_2$-t-$C_4H_9$ | $CH_3$ | H |
| 517 | $CO_2$-Ph | $CH_3$ | H |
| 518 | $CO_2$-3-pyridyl | $CH_3$ | H |
| 519 | $CONHCH_3$ | $CH_3$ | H |
| 520 | $CONHC_2H_5$ | $CH_3$ | H |
| 521 | CONH-phenyl | $CH_3$ | H |
| 522 | $CON(CH_3)_2$ | $CH_3$ | H |
| 523 | $CON(CH_2CH_3)_2$ | $CH_3$ | H |
| 524 | $CON(phenyl)_2$ | $CH_3$ | H |
| 525 | H | $OCH_3$ | H |
| 526 | F | $OCH_3$ | H |
| 527 | Cl | $OCH_3$ | H |
| 528 | Br | $OCH_3$ | H |
| 529 | OH | $OCH_3$ | H |
| 530 | SH | $OCH_3$ | H |
| 531 | $NH_2$ | $OCH_3$ | H |
| 532 | CN | $OCH_3$ | H |
| 533 | $NO_2$ | $OCH_3$ | H |
| 534 | SCN | $OCH_3$ | H |
| 535 | NH—$NH_2$ | $OCH_3$ | H |
| 536 | $CH_3$ | $OCH_3$ | H |
| 537 | $C_2H_5$ | $OCH_3$ | H |
| 538 | n-$C_3H_7$ | $OCH_3$ | H |
| 539 | i-$C_3H_7$ | $OCH_3$ | H |
| 540 | n-$C_4H_9$ | $OCH_3$ | H |
| 541 | s-$C_4H_9$ | $OCH_3$ | H |
| 542 | i-$C_4H_9$ | $OCH_3$ | H |
| 543 | t-$C_4H_9$ | $OCH_3$ | H |
| 544 | $CH_2Cl$ | $OCH_3$ | H |
| 545 | $CHCl_2$ | $OCH_3$ | H |
| 546 | $CCl_3$ | $OCH_3$ | H |
| 547 | $CH_2F$ | $OCH_3$ | H |
| 548 | $CHF_2$ | $OCH_3$ | H |
| 549 | $CF_3$ | $OCH_3$ | H |
| 550 | $CH_2CF_3$ | $OCH_3$ | H |
| 551 | $CH_2OCH_3$ | $OCH_3$ | H |
| 552 | $CH_2OCH_2CH_3$ | $OCH_3$ | H |
| 553 | $CH_2NH_2$ | $OCH_3$ | H |
| 554 | $OCH_3$ | $OCH_3$ | H |
| 555 | $OC_2H_5$ | $OCH_3$ | H |
| 556 | O-n-$C_3H_7$ | $OCH_3$ | H |
| 557 | O-i-$C_3H_7$ | $OCH_3$ | H |
| 558 | O-n-$C_4H_9$ | $OCH_3$ | H |
| 559 | O-s-$C_4H_9$ | $OCH_3$ | H |
| 560 | O-i-$C_4H_9$ | $OCH_3$ | H |
| 561 | O-t-$C_4H_9$ | $OCH_3$ | H |
| 562 | $OCHF_2$ | $OCH_3$ | H |
| 563 | $OCF_3$ | $OCH_3$ | H |
| 564 | $OCH_2CF_3$ | $OCH_3$ | H |
| 565 | $OCH_2OCH_3$ | $OCH_3$ | H |
| 566 | $SCH_3$ | $OCH_3$ | H |
| 567 | $SC_2H_5$ | $OCH_3$ | H |
| 568 | S-n-$C_3H_7$ | $OCH_3$ | H |
| 569 | S-i-$C_3H_7$ | $OCH_3$ | H |
| 570 | S-n-$C_4H_9$ | $OCH_3$ | H |
| 571 | S-s-$C_4H_9$ | $OCH_3$ | H |
| 572 | S-i-$C_4H_9$ | $OCH_3$ | H |
| 573 | S-t-$C_4H_9$ | $OCH_3$ | H |
| 574 | $SCHF_2$ | $OCH_3$ | H |
| 575 | $SCF_3$ | $OCH_3$ | H |
| 576 | $SCH_2CF_3$ | $OCH_3$ | H |
| 577 | $SCH_2OCH_3$ | $OCH_3$ | H |
| 578 | $NHCH_3$ | $OCH_3$ | H |
| 579 | $NHC_2H_5$ | $OCH_3$ | H |
| 580 | NHPh | $OCH_3$ | H |
| 581 | $N(CH_3)_2$ | $OCH_3$ | H |
| 582 | $N(CH_2CH_3)_2$ | $OCH_3$ | H |
| 583 | $N(phenyl)_2$ | $OCH_3$ | H |
| 584 | $(CH_2)_2COCH_3$ | $OCH_3$ | H |
| 585 | phenyl | $OCH_3$ | H |
| 586 | 2-F-phenyl | $OCH_3$ | H |
| 587 | 3-F-phenyl | $OCH_3$ | H |
| 588 | 4-F-phenyl | $OCH_3$ | H |
| 589 | 2-Cl-phenyl | $OCH_3$ | H |
| 590 | 3-Cl-phenyl | $OCH_3$ | H |
| 591 | 4-Cl-phenyl | $OCH_3$ | H |
| 592 | 2-OH-phenyl | $OCH_3$ | H |
| 593 | 3-OH-phenyl | $OCH_3$ | H |
| 594 | 4-OH-phenyl | $OCH_3$ | H |
| 595 | 2-$OCH_3$-phenyl | $OCH_3$ | H |
| 596 | 3-$OCH_3$-phenyl | $OCH_3$ | H |
| 597 | 4-$OCH_3$-phenyl | $OCH_3$ | H |
| 598 | 2-$OCF_3$-phenyl | $OCH_3$ | H |
| 599 | 3-$OCF_3$-phenyl | $OCH_3$ | H |
| 600 | 4-$OCF_3$-phenyl | $OCH_3$ | H |

TABLE A-continued

Particularly preferred combinations of $R^1$, $R^2$ and $R^3$

| | $R^3$ | $R^1$ | $R^2$ |
|---|---|---|---|
| 601 | 2-OCHF$_2$-phenyl | OCH$_3$ | H |
| 602 | 3-OCHF$_2$-phenyl | OCH$_3$ | H |
| 603 | 4-OCHF$_2$-phenyl | OCH$_3$ | H |
| 604 | 2-CF$_3$-phenyl | OCH$_3$ | H |
| 605 | 3-CF$_3$-phenyl | OCH$_3$ | H |
| 606 | 4-CF$_3$-phenyl | OCH$_3$ | H |
| 607 | 2-CH$_3$-phenyl | OCH$_3$ | H |
| 608 | 3-CH$_3$-phenyl | OCH$_3$ | H |
| 609 | 4-CH$_3$-phenyl | OCH$_3$ | H |
| 610 | 2-NO$_2$-phenyl | OCH$_3$ | H |
| 611 | 3-NO$_2$-phenyl | OCH$_3$ | H |
| 612 | 4-NO$_2$-phenyl | OCH$_3$ | H |
| 613 | 2-pyridyl | OCH$_3$ | H |
| 614 | 3-pyridyl | OCH$_3$ | H |
| 615 | 4-pyridyl | OCH$_3$ | H |
| 616 | 3'-CH$_3$-2-pyridyl | OCH$_3$ | H |
| 617 | 4'-CH$_3$-2-pyridyl | OCH$_3$ | H |
| 618 | 5'-CH$_3$-2-pyridyl | OCH$_3$ | H |
| 619 | 6'-CH$_3$-2-pyridyl | OCH$_3$ | H |
| 620 | 2'-CH$_3$-3-pyridyl | OCH$_3$ | H |
| 621 | 4'-CH$_3$-3-pyridyl | OCH$_3$ | H |
| 622 | 5'-CH$_3$-3-pyridyl | OCH$_3$ | H |
| 623 | 6'-CH$_3$-3-pyridyl | OCH$_3$ | H |
| 624 | 2'-CH$_3$-4-pyridyl | OCH$_3$ | H |
| 625 | 3'-CH$_3$-4-pyridyl | OCH$_3$ | H |
| 626 | 3'-Cl-2-pyridyl | OCH$_3$ | H |
| 627 | 4'-Cl-2-pyridyl | OCH$_3$ | H |
| 628 | 5'-Cl-2-pyridyl | OCH$_3$ | H |
| 629 | 6'-Cl-2-pyridyl | OCH$_3$ | H |
| 630 | 2'-Cl-3-pyridyl | OCH$_3$ | H |
| 631 | 4'-Cl-3-pyridyl | OCH$_3$ | H |
| 632 | 5'-Cl-3-pyridyl | OCH$_3$ | H |
| 633 | 6'-Cl-3-pyridyl | OCH$_3$ | H |
| 634 | 2'-Cl-4-pyridyl | OCH$_3$ | H |
| 635 | 3'-Cl-4-pyridyl | OCH$_3$ | H |
| 636 | cyclohexylamino | OCH$_3$ | H |
| 637 | cyclopentylamino | OCH$_3$ | H |
| 638 | morpholino | OCH$_3$ | H |
| 639 | CO$_2$H | OCH$_3$ | H |
| 640 | CO$_2$CH$_3$ | OCH$_3$ | H |
| 641 | CO$_2$C$_2$H$_5$ | OCH$_3$ | H |
| 642 | CO$_2$-n-C$_3$H$_7$ | OCH$_3$ | H |
| 643 | CO$_2$-i-C$_3$H$_7$ | OCH$_3$ | H |
| 644 | CO$_2$-n-C$_4$H$_9$ | OCH$_3$ | H |
| 645 | CO$_2$-s-C$_4$H$_9$ | OCH$_3$ | H |
| 646 | CO$_2$-i-C$_4$H$_9$ | OCH$_3$ | H |
| 647 | CO$_2$-t-C$_4$H$_9$ | OCH$_3$ | H |
| 648 | CO$_2$-Ph | OCH$_3$ | H |
| 649 | CO$_2$-3-pyridyl | OCH$_3$ | H |
| 650 | CONHCH$_3$ | OCH$_3$ | H |
| 651 | CONHC$_2$H$_5$ | OCH$_3$ | H |
| 652 | CONH-phenyl | OCH$_3$ | H |
| 653 | CON(CH$_3$)$_2$ | OCH$_3$ | H |
| 654 | CON(CH$_2$CH$_3$)$_2$ | OCH$_3$ | H |
| 655 | CON(phenyl)$_2$ | OCH$_3$ | H |
| 656 | H | Cl | H |
| 657 | F | Cl | H |
| 658 | Cl | Cl | H |
| 659 | Br | Cl | H |
| 660 | OH | Cl | H |
| 661 | SH | Cl | H |
| 662 | NH$_2$ | Cl | H |
| 663 | CN | Cl | H |
| 664 | NO$_2$ | Cl | H |
| 665 | SCN | Cl | H |
| 666 | NH—NH$_2$ | Cl | H |
| 667 | CH$_3$ | Cl | H |
| 668 | C$_2$H$_5$ | Cl | H |
| 669 | n-C$_3$H$_7$ | Cl | H |
| 670 | i-C$_3$H$_7$ | Cl | H |
| 671 | n-C$_4$H$_9$ | Cl | H |
| 672 | s-C$_4$H$_9$ | Cl | H |
| 673 | i-C$_4$H$_9$ | Cl | H |
| 674 | t-C$_4$H$_9$ | Cl | H |
| 675 | CH$_2$Cl | Cl | H |
| 676 | CHCl$_2$ | Cl | H |
| 677 | CCl$_3$ | Cl | H |
| 678 | CH$_2$F | Cl | H |
| 679 | CHF$_2$ | Cl | H |
| 680 | CF$_3$ | Cl | H |
| 681 | CH$_2$CF$_3$ | Cl | H |
| 682 | CH$_2$OCH$_3$ | Cl | H |
| 683 | CH$_2$OCH$_2$CH$_3$ | Cl | H |
| 684 | CH$_2$NH$_2$ | Cl | H |
| 685 | OCH$_3$ | Cl | H |
| 686 | OC$_2$H$_5$ | Cl | H |
| 687 | O-n-C$_3$H$_7$ | Cl | H |
| 688 | O-i-C$_3$H$_7$ | Cl | H |
| 689 | O-n-C$_4$H$_9$ | Cl | H |
| 690 | O-s-C$_4$H$_9$ | Cl | H |
| 691 | O-i-C$_4$H$_9$ | Cl | H |
| 692 | O-t-C$_4$H$_9$ | Cl | H |
| 693 | OCHF$_2$ | Cl | H |
| 694 | OCF$_3$ | Cl | H |
| 695 | OCH$_2$CF$_3$ | Cl | H |
| 696 | OCH$_2$OCH$_3$ | Cl | H |
| 697 | SCH$_3$ | Cl | H |
| 698 | SC$_2$H$_5$ | Cl | H |
| 699 | S-n-C$_3$H$_7$ | Cl | H |
| 700 | S-i-C$_3$H$_7$ | Cl | H |
| 701 | S-n-C$_4$H$_9$ | Cl | H |
| 702 | S-s-C$_4$H$_9$ | Cl | H |
| 703 | S-i-C$_4$H$_9$ | Cl | H |
| 704 | S-t-C$_4$H$_9$ | Cl | H |
| 705 | SCHF$_2$ | Cl | H |
| 706 | SCF$_3$ | Cl | H |
| 707 | SCH$_2$CF$_3$ | Cl | H |
| 708 | SCH$_2$OCH$_3$ | Cl | H |
| 709 | NHCH$_3$ | Cl | H |
| 710 | NHC$_2$H$_5$ | Cl | H |
| 711 | NHPh | Cl | H |
| 712 | N(CH$_3$)$_2$ | Cl | H |
| 713 | N(CH$_2$CH$_3$)$_2$ | Cl | H |
| 714 | N(phenyl)$_2$ | Cl | H |
| 715 | (CH$_2$)$_2$COCH$_3$ | Cl | H |
| 716 | phenyl | Cl | H |
| 717 | 2-F-phenyl | Cl | H |
| 718 | 3-F-phenyl | Cl | H |
| 719 | 4-F-phenyl | Cl | H |
| 720 | 2-Cl-phenyl | Cl | H |
| 721 | 3-Cl-phenyl | Cl | H |
| 722 | 4-Cl-phenyl | Cl | H |
| 723 | 2-OH-phenyl | Cl | H |
| 724 | 3-OH-phenyl | Cl | H |
| 725 | 4-OH-phenyl | Cl | H |
| 726 | 2-OCH$_3$-phenyl | Cl | H |
| 727 | 3-OCH$_3$-phenyl | Cl | H |
| 728 | 4-OCH$_3$-phenyl | Cl | H |
| 729 | 2-OCF$_3$-phenyl | Cl | H |
| 730 | 3-OCF$_3$-phenyl | Cl | H |
| 731 | 4-OCF$_3$-phenyl | Cl | H |
| 732 | 2-OCHF$_2$-phenyl | Cl | H |
| 733 | 3-OCHF$_2$-phenyl | Cl | H |
| 734 | 4-OCHF$_2$-phenyl | Cl | H |
| 735 | 2-CF$_3$-phenyl | Cl | H |
| 736 | 3-CF$_3$-phenyl | Cl | H |
| 737 | 4-CF$_3$-phenyl | Cl | H |
| 738 | 2-CH$_3$-phenyl | Cl | H |
| 739 | 3-CH$_3$-phenyl | Cl | H |
| 740 | 4-CH$_3$-phenyl | Cl | H |
| 741 | 2-NO$_2$-phenyl | Cl | H |
| 742 | 3-NO$_2$-phenyl | Cl | H |
| 743 | 4-NO$_2$-phenyl | Cl | H |
| 744 | 2-pyridyl | Cl | H |
| 745 | 3-pyridyl | Cl | H |
| 746 | 4-pyridyl | Cl | H |
| 747 | 3'-CH$_3$-2-pyridyl | Cl | H |
| 748 | 4'-CH$_3$-2-pyridyl | Cl | H |
| 749 | 5'-CH$_3$-2-pyridyl | Cl | H |
| 750 | 6'-CH$_3$-2-pyridyl | Cl | H |

TABLE A-continued

Particularly preferred combinations of $R^1$, $R^2$ and $R^3$

| | $R^3$ | $R^1$ | $R^2$ |
|---|---|---|---|
| 751 | 2'-CH$_3$-3-pyridyl | Cl | H |
| 752 | 4'-CH$_3$-3-pyridyl | Cl | H |
| 753 | 5'-CH$_3$-3-pyridyl | Cl | H |
| 754 | 6'-CH$_3$-3-pyridyl | Cl | H |
| 755 | 2'-CH$_3$-4-pyridyl | Cl | H |
| 756 | 3'-CH$_3$-4-pyridyl | Cl | H |
| 757 | 3'-Cl-2-pyridyl | Cl | H |
| 758 | 4'-Cl-2-pyridyl | Cl | H |
| 759 | 5'-Cl-2-pyridyl | Cl | H |
| 760 | 6'-Cl-2-pyridyl | Cl | H |
| 761 | 2'-Cl-3-pyridyl | Cl | H |
| 762 | 4'-Cl-3-pyridyl | Cl | H |
| 763 | 5'-Cl-3-pyridyl | Cl | H |
| 764 | 6'-Cl-3-pyridyl | cl | H |
| 765 | 2'-Cl-4-pyridyl | Cl | H |
| 766 | 3'-Cl-4-pyridyl | Cl | H |
| 767 | cyclohexylamino | Cl | H |
| 768 | cyclopentylamino | Cl | H |
| 769 | morpholino | Cl | H |
| 770 | CO$_2$H | Cl | H |
| 771 | CO$_2$CH$_3$ | Cl | H |
| 772 | CO$_2$C$_2$H$_5$ | Cl | H |
| 773 | CO$_2$-n-C$_3$H$_7$ | Cl | H |
| 774 | CO$_2$-i-C$_3$H$_7$ | Cl | H |
| 775 | CO$_2$-n-C$_4$H$_9$ | Cl | H |
| 776 | CO$_2$-s-C$_4$H$_9$ | Cl | H |
| 777 | CO$_2$-i-C$_4$H$_9$ | Cl | H |
| 778 | CO$_2$-t-C$_4$H$_9$ | Cl | H |
| 779 | CO$_2$-phenyl | Cl | H |
| 780 | CO$_2$-3-pyridyl | Cl | H |
| 781 | CONHCH$_3$ | Cl | H |
| 782 | CONHC$_2$H$_5$ | Cl | H |
| 783 | CONH-phenyl | Cl | H |
| 784 | CON(CH$_3$)$_2$ | Cl | H |
| 785 | CON(CH$_2$CH$_3$)$_2$ | Cl | H |
| 786 | CON(phenyl)$_2$ | Cl | H |
| 787 | 2-fluorophenoxy | CH$_3$ | CH$_3$ |
| 788 | 2-fluorophenoxy | OCH$_3$ | CH$_3$ |
| 789 | 2-fluorophenoxy | Cl | CH$_3$ |
| 790 | 2-fluorophenoxy | CH$_3$ | H |
| 791 | 2-fluorophenoxy | OCH$_3$ | H |
| 792 | 2-fluorophenoxy | Cl | H |
| 793 | phenoxy | CH$_3$ | CH$_3$ |
| 794 | phenoxy | OCH$_3$ | CH$_3$ |
| 795 | phenoxy | Cl | CH$_3$ |
| 796 | phenoxy | CH$_3$ | H |
| 797 | phenoxy | OCH$_3$ | H |
| 798 | phenoxy | Cl | H |
| 799 | 2-methoxyphenoxy | CH$_3$ | CH$_3$ |
| 800 | 2-methoxyphenoxy | OCH$_3$ | CH$_3$ |
| 801 | 2-methoxyphenoxy | Cl | CH$_3$ |
| 802 | 2-methoxyphenoxy | CH$_3$ | H |
| 803 | 2-methoxyphenoxy | OCH$_3$ | H |
| 804 | 2-methoxyphenoxy | Cl | H |
| 805 | cyclopropyl | CH$_3$ | CH$_3$ |
| 806 | cyclopropyl | OCH$_3$ | CH$_3$ |
| 807 | cyclopropyl | Cl | CH$_3$ |
| 808 | cyclopropyl | CH$_3$ | H |
| 809 | cyclopropyl | OCH$_3$ | H |
| 810 | cyclopropyl | Cl | H |

Here are some further particular examples:
2-F-phenyl = 2-fluorophenyl
2-Cl-phenyl = 2-chlorophenyl
2-OH-phenyl = 2-hydroxyphenyl
2-OCH$_3$-phenyl = 2-methoxyphenyl
2-OCF$_3$-phenyl = 2-trifluoromethoxyphenyl
2-OCHF$_2$-phenyl = 2-difluoromethoxyphenyl
2-NO$_2$-phenyl = 2-nitrophenyl
3'-CH$_3$-2-pyridyl = 3'-methylpyridin-2-yl Examples of benzothiazol-5-ylcarbonyl derivatives of cyclohexenones (compounds I-1=compounds I where X=C—R$^3$ and Y=S) which are particularly preferred according to the invention are the compounds listed in Tables 1 to 25.

TABLE 1

Compounds I-1a.1 to I-1a.810

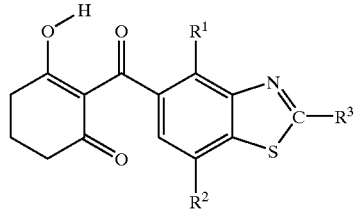

I-1a

Compounds of the formula I-1a, in which the substituents $R^1$, $R^2$ and $R^3$ for each individual compound correspond in each case to one row of Table A.

TABLE 2

Compounds I-1b.1 to I-1b.810

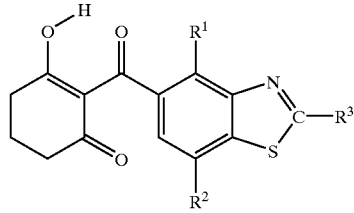

I-1b

Compounds of the formula I-1b, in which the substituents $R^1$ $R^2$ and $R^3$ for each individual compound correspond in each case to one row of Table A.

TABLE 3

Compounds I-1c.1 to I-1c.810

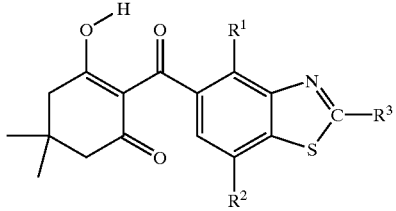

I-1c

Compounds of the formula I-1c, in which the substituents $R_1$, $R^2$ and $R^3$ for each individual compound correspond in each case to one row of Table A.

TABLE 4

Compounds I-1d.1 to I-1d.810

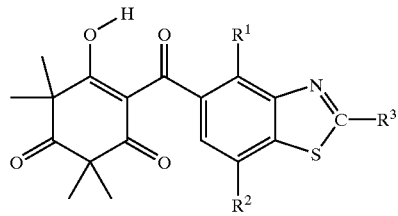

I-1d

Compounds of the formula I-1d, in which the substituents $R^1$, $R^2$ and $R^3$ for each individual compound correspond in each case to one row of Table A.

TABLE 5

Compounds I-1e.1 to I-1e.810

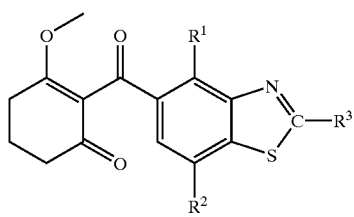

I-1e

Compounds of the formula I-1e, in which the substituents $R^1$, $R^2$ and $R^3$ for each individual compound correspond in each case to one row of Table A.

TABLE 6

Compounds I-1f.1 to I-1f.810

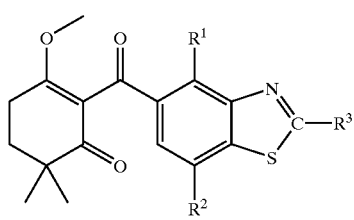

I-1f

Compounds of the formula I-1f, in which the substituents $R^1$, $R^2$ and $R^3$ for each individual compound correspond in each case to one row of Table A.

TABLE 7

Compounds I-1g.1 to I-1g.810

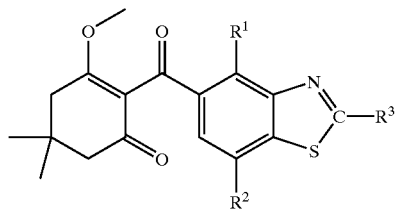

I-1g

Compounds of the formula I-1g, in which the substituents $R^1$, $R^2$ and $R^3$ for each individual compound correspond in each case to one row of Table A.

TABLE 8

Compounds I-1h.1 to I-1h.810

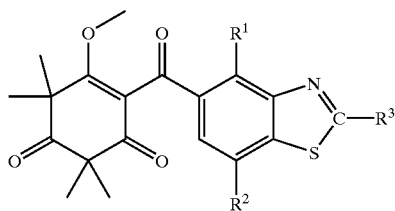

I-1h

Compounds of the formula I-1h, in which the substituents $R^1$, $R^2$ and $R^3$ for each individual compound correspond in each case to one row of Table A.

TABLE 9

Compounds I-1i.1 to I-1i.810

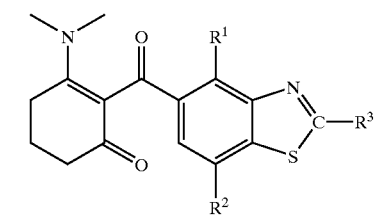

I-1i

Compounds of the formula I-1i, in which the substituents $R^1$, $R^2$ and $R^3$ for each individual compound correspond in each case to one row of Table A.

TABLE 10

Compounds I-1k.1 to I-1k.810

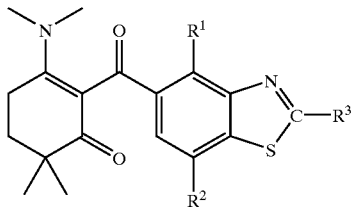

I-1k

Compounds of the formula I-1k, in which the substituents $R^1$, $R^2$ and $R^3$ for each individual compound correspond in each case to one row of Table A.

TABLE 11

Compounds I-1l.1 to I-1l.810

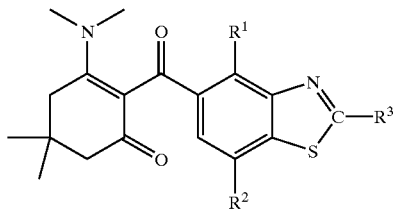

I-1l

Compounds of the formula I-1l, in which the substituents $R^1$, $R^2$ and $R^3$ for each individual compound correspond in each case to one row of Table A.

TABLE 12

Compounds I-1m.1 to I-1m.810

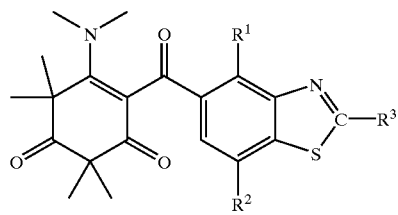

I-1m

Compounds of the formula I-1m, in which the substituents $R^1$, $R^2$ and $R^3$ for each individual compound correspond in each case to one row of Table A.

TABLE 13

Compounds I-1n.1 to I-1n.810

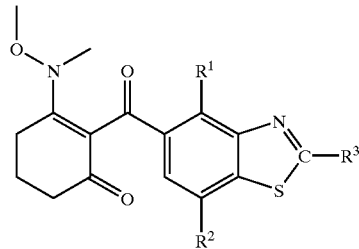

I-1n

Compounds of the formula I-1n, in which the substituents $R^1$, $R^2$ and $R^3$ for each individual compound correspond in each case to one row of Table A.

TABLE 14

Compounds I-1o.1 to I-1o.810

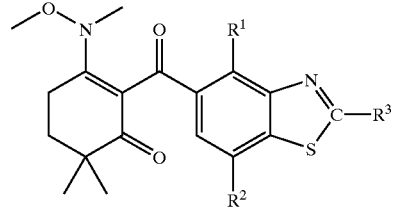

I-1o

Compounds of the formula I-1o, in which the substituents $R^1$, $R^2$ and $R^3$ for each individual compound correspond in each case to one row of Table A.

TABLE 15

Compounds I-1p.1 to I-1p.810

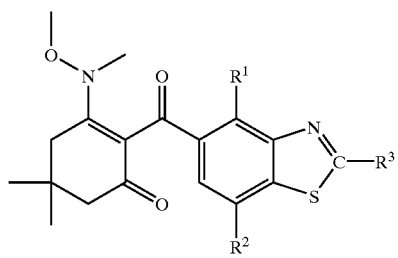

I-1p

Compounds of the formula I-1p, in which the substituents R¹, R² and R³ for each individual compound correspond in each case to one row of Table A.

TABLE 16

Compounds I-1q.1 to I-1q.810

I-1q

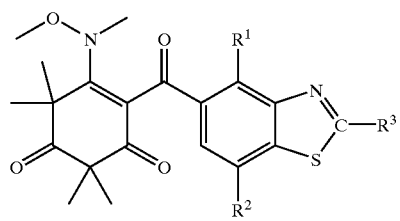

Compounds of the formula I-1q, in which the substituents R¹, R² and R³ for each individual compound correspond in each case to one row of Table A.

TABLE 17

Compounds I-1r.1 to I-1r.810

I-1r

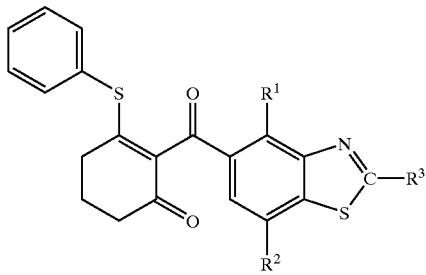

Compounds of the formula I-1r, in which the substituents R¹, R² and R³ for each individual compound correspond in each case to one row of Table A.

TABLE 18

Compounds I-1s.1 to I-1s.810

I-1s

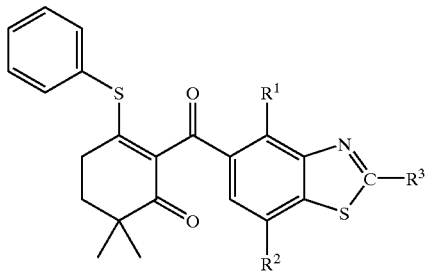

Compounds of the formula I-1s, in which the substituents R¹, R² and R³ for each individual compound correspond in each case to one row of Table A.

TABLE 19

Compounds I-1t.1 to I-1t.810

I-1t

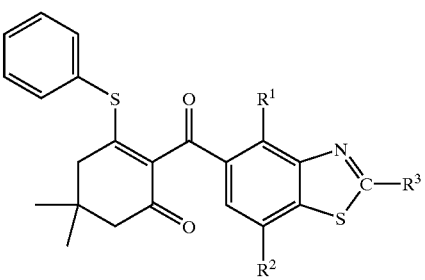

Compounds of the formula I-1t, in which the substituents R¹, R² and R³ for each individual compound correspond in each case to one row of Table A.

TABLE 20

Compounds I-1u.1 to I-1u.810

I-1u

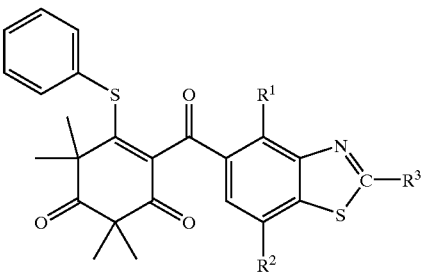

Compounds of the formula I-1u, in which the substituents R¹, R² and R³ for each individual compound correspond in each case to one row of Table A.

TABLE 21

Compounds I-1v.1 to I-1v.810

I-1v

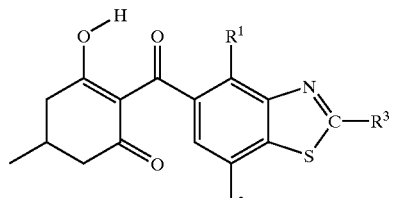

Compounds of the formula I-1v, in which the substituents $R^1$, $R^2$ and $R^3$ for each individual compound correspond in each case to one row of Table A..

TABLE 22

Compounds I-1w.1 to I-1w.810

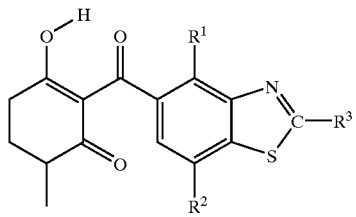

I-1w

Compounds of the formula I-1w, in which the substituents $R^1$, $R^2$ and $R^3$ for each individual compound correspond in each-case to one row of Table A.

TABLE 23

Compounds I-1x.1 to I-1x.810

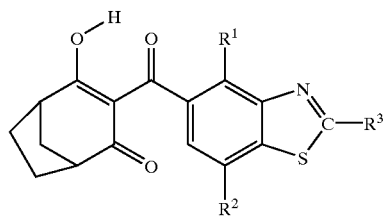

I-1x

Compounds of the formula I-1x, in which the substituents $R^1$, $R^2$ and $R^3$ for each individual compound correspond in each case to one row of Table A.

TABLE 24

Compounds I-1y.1 to I-1y.810

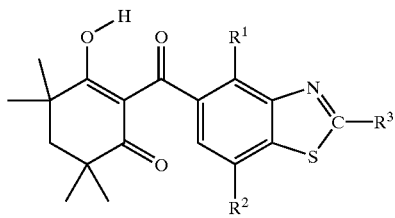

I-1y

Compounds of the formula I-1y, in which the substituents $R^1$, $R^2$ and $R^3$ for each individual compound correspond in each case to one row of Table A.

TABLE 25

Compounds I-1z.1 to I-1z.810

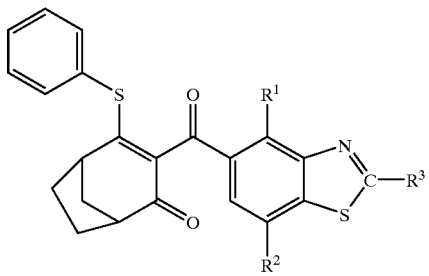

I-1z

Compounds of the formula I-1z, in which the substituents $R^1$, $R^2$ and $R^3$ for each individual compound correspond in each case to one row of Table A.

Examples of particularly preferred compounds according to the invention are the benzothiazole S-dioxide compounds I-1'a.1 to I-1'a.810, I-1'b.1 to I-1'b.810, . . . I-1'z.1 to I-1'z.810 (compounds I-1'=compounds I where X=C—$R^3$ and Y=$SO_2$). They differ from the benzothiazole compounds I-1a.1 to I-1a.810, I-1b.1 to I-1b.810, . . . I-1z.1 to I-1z.810 listed in Tables 1 to 25 in that the heterocyclic sulfur atom is present as an $SO_2$ group.

Examples of particularly preferred cyclohexenone derivatives of benzoxazole-5-carbonyl compounds according to the invention (compounds I-2 =compounds I where X=C—$R^3$ and Y=O) are the compounds mentioned in Tables 26 to 50.

TABLE 26

Compounds I-2a.1 to I-2a.810

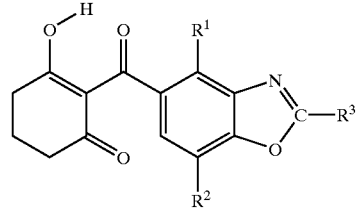

I-2a

TABLE 27

Compounds I-2b.1 to I-2b.810

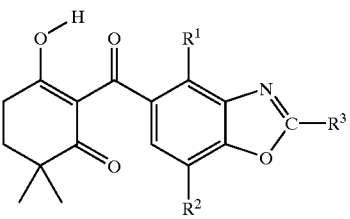

I-2b

Compounds of the formula I-2b, in which the substituents $R^1$, $R^2$ and $R^3$ for each individual compound correspond in each case to one row of Table A.

TABLE 28

Compounds I-2c.1 to I-2c.810

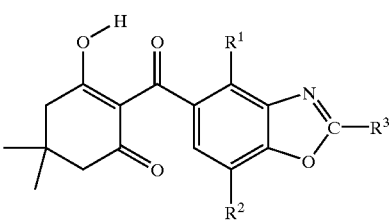

I-2c

Compounds of the formula I-2c, in which the substituents $R^1$, $R^2$ and $R^3$ for each individual compound correspond in each case to one row of Table A.

TABLE 29

Compounds I-2d.1 to I-2d.810

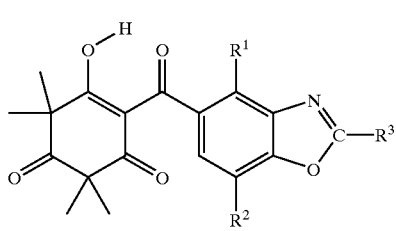

I-2d

Compounds of the formula I-2d, in which the substituents $R^1$, $R^2$ and $R^3$ for each individual compound correspond in each case to one row of Table A.

TABLE 30

Compounds I-2e.1 to I-2e.810

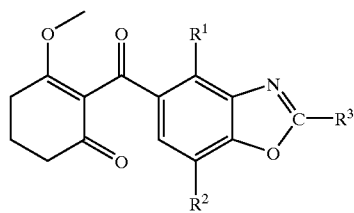

I-2e

Compounds of the formula I-2e, in which the substituents $R^1$, $R^2$ and $R^3$ for each individual compound correspond in each case to one row of Table A.

TABLE 31

Compounds I-2f.1 to I-2f.810

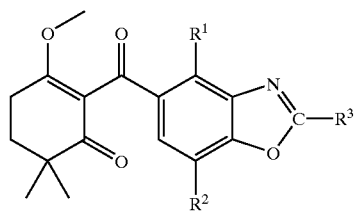

I-2f

Compounds of the formula I-2f, in which the substituents $R^1$, $R^2$ and $R^3$ for each individual compound correspond in each case to one row of Table A.

TABLE 32

Compounds I-2g.1 to I-2g.810

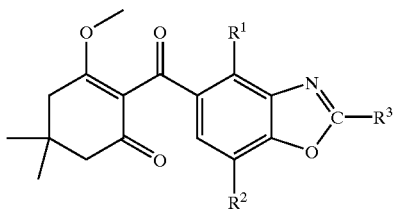

I-2g

Compounds of the formula I-2g, in which the substituents R$^1$, R$^2$ and R$^3$ for each individual compound correspond in each case to one row of Table A.

TABLE 33

Compounds I-2h.1 to I-2h.810

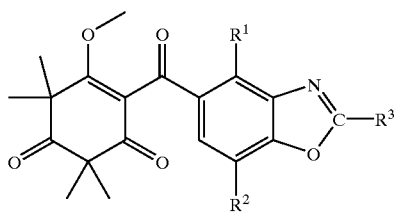

I-2h

Compounds of the formula I-2h, in which the substituents R$^1$, R$^2$ and R$^3$ for each individual compound correspond in each case to one row of Table A.

TABLE 34

Compounds I-2i.1 to I-2i.810

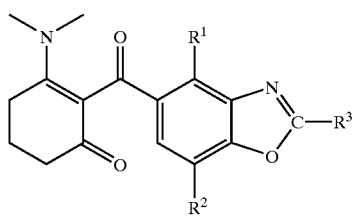

I-2i

Compounds of the formula I-2i, in which the substituents R$^1$, R$^2$ and R$^3$ for each individual compound correspond in each case to one row of Table A.

TABLE 35

Compounds I-2k.1 to I-2k.810

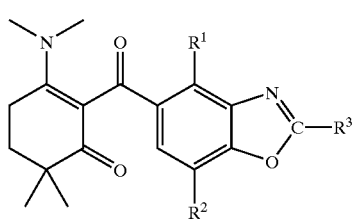

I-2k

Compounds of the formula I-2k, in which the substituents R$^1$, R$^2$ and R$^3$ for each individual compound correspond in each case to one row of Table A.

TABLE 36

Compounds I-2l.1 to I-2l.810

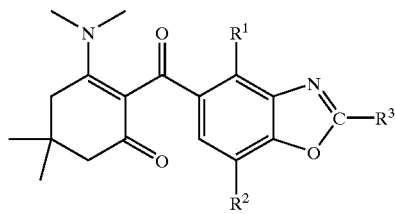

I-2l

Compounds of the formula I-2l, in which the substituents R$^1$, R$^2$ and R$^3$ for each individual compound correspond in each case to one row of Table A.

TABLE 37

Compounds I-2m.1 to I-2m.810

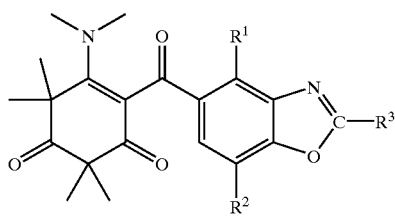

I-2m

Compounds of the formula I-2m, in which the substituents R$^1$, R$^2$ and R$^3$ for each individual compound correspond in each case to one row of Table A.

TABLE 38

Compounds I-2n.1 to I-2n.810

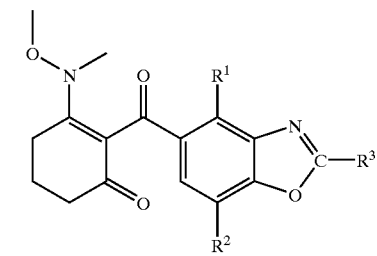

I-2n

Compounds of the formula I-2n, in which the substituents $R^1$, $R^2$ and $R^3$ for each individual compound correspond in each case to one row of Table A.

TABLE 39

Compounds I-2o.1 to I-2o.810

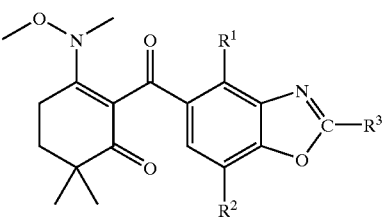

I-2o

Compounds of the formula I-2o, in which the substituents $R^1$, $R^2$ and $R^3$ for each individual compound correspond in each case to one row of Table A.

TABLE 40

Compounds I-2p.1 to I-2p.810

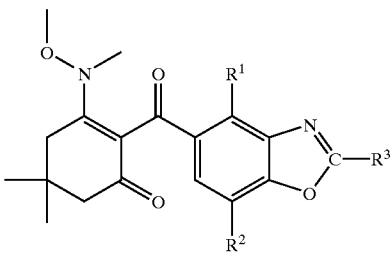

I-2p

Compounds of the formula I-2p, in which the substituents $R^1$, $R^2$ and $R^3$ for each individual compound correspond in each case to one row of Table A.

TABLE 41

Compounds I-2q.1 to I-2q.810

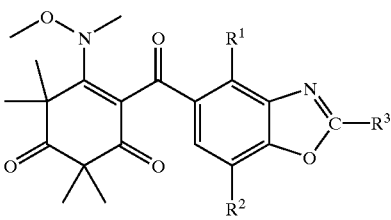

I-2q

Compounds of the formula I-2q, in which the substituents $R^1$, $R^2$ and $R^3$ for each individual compound correspond in each case to one row of Table A.

TABLE 42

Compounds I-2r.1 to I-2r.810

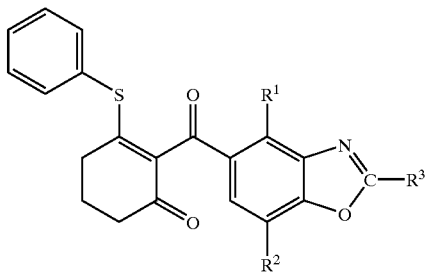

I-2r

Compounds of the formula I-2r, in which the substituents $R^1$, $R^2$ and $R^3$ for each individual compound correspond in each case to one row of Table A.

TABLE 43

Compounds I-2s.1 to I-2s.810

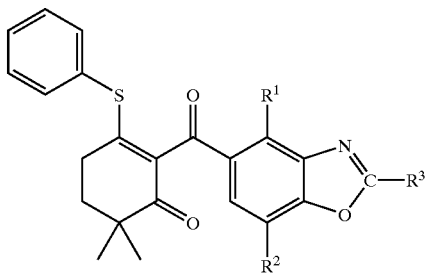

I-2s

Compounds of the formula I-2s, in which the substituents $R^1$, $R^2$ and $R^3$ for each individual compound correspond in each case to one row of Table A.

TABLE 44

Compounds I-2t.1 to I-2t.810

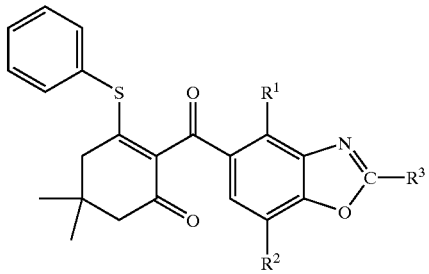

I-2t

Compounds of the formula I-2t, in which the substituents $R^1$, $R^2$ and $R^3$ for each individual compound correspond in each case to one row of Table A.

TABLE 45

Compounds I-2u.1 to I-2u.810

I-2u

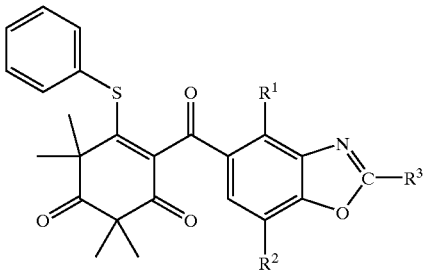

Compounds of the formula I-2u, in which the substituents $R^1$, $R^2$ and $R^3$ for each individual compound correspond in each case to one row of Table A.

TABLE 46

Compounds I-2v.1 to I-2v.810

I-2v

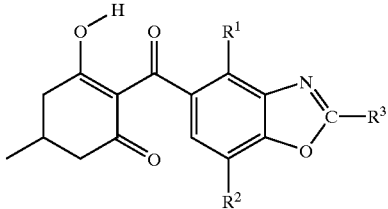

Compounds of the formula I-2v, in which the substituents $R^1$, $R^2$ and $R^3$ for each individual compound correspond in each case to one row of Table A.

TABLE 47

Compounds I-2w.1 to I-2w.810

I-2w

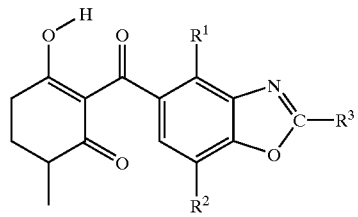

Compounds of the formula I-2w, in which the substituents $R^1$, $R^2$ and $R^3$ for each individual compound correspond in each case to one row of Table A.

TABLE 48

Compounds I-2x.1 to I-2x.810

I-2x

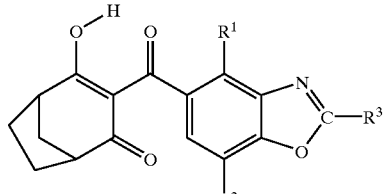

Compounds of the formula I-2x, in which the substituents $R^1$, $R^2$ and $R^3$ for each individual-compound correspond in each case to one row of Table A.

TABLE 49

Compounds I-2y.1 to I-2y.810

I-2y

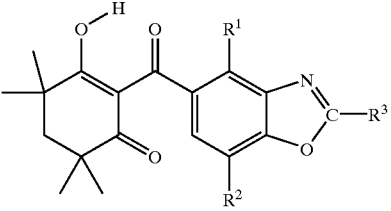

Compounds of the formula I-2y, in which the substituents $R^1$, $R^2$ and $R^3$ for each individual compound correspond in each case to one row of Table A.

TABLE 50

Compounds I-2z.1 to I-2z.810

I-2z

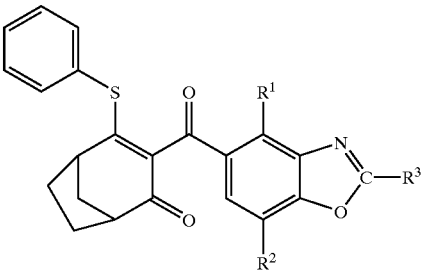

Compounds of the formula I-2z, in which the substituents $R^1$, $R^2$ and $R^3$ for each individual compound correspond in each case to one row of Table A.

Particularly preferred combinations of $R^1$, $R^2$, $R^3$ and $R^4$ for cyclohexenone derivatives of the formula I according to the invention which are derived from benzimidazole-5-carboxylic acids are listed in Table B below.

TABLE B

| | R³ | R¹ | R² | R⁴ |
|---|---|---|---|---|
| 1 | CH₃ | CH₃ | CH₃ | H |
| 2 | C₂H₅ | CH₃ | CH₃ | H |
| 3 | n-C₃H₇ | CH₃ | CH₃ | H |
| 4 | i-C₃H₇ | CH₃ | CH₃ | H |
| 5 | n-C₄H₉ | CH₃ | CH₃ | H |
| 6 | s-C₄H₉ | CH₃ | CH₃ | H |
| 7 | i-C₄H₉ | CH₃ | CH₃ | H |
| 8 | t-C₄H₉ | CH₃ | CH₃ | H |
| 9 | CH₂Cl | CH₃ | CH₃ | H |
| 10 | CHCl₂ | CH₃ | CH₃ | H |
| 11 | CCl₃ | CH₃ | CH₃ | H |
| 12 | CH₂F | CH₃ | CH₃ | H |
| 13 | CHF₂ | CH₃ | CH₃ | H |
| 14 | CF₃ | CH₃ | CH₃ | H |
| 15 | CH₂CF₃ | CH₃ | CH₃ | H |
| 16 | CH₂OCH₃ | CH₃ | CH₃ | H |
| 17 | CH₂OCH₂CH₃ | CH₃ | CH₃ | H |
| 18 | CH₂NH₂ | CH₃ | CH₃ | H |
| 19 | (CH₂)₂COCH₃ | CH₃ | CH₃ | H |
| 20 | phenyl | CH₃ | CH₃ | H |
| 21 | 2-F-phenyl | CH₃ | CH₃ | H |
| 22 | 3-F-phenyl | CH₃ | CH₃ | H |
| 23 | 4-F-phenyl | CH₃ | CH₃ | H |
| 24 | 2-Cl-phenyl | CH₃ | CH₃ | H |
| 25 | 3-Cl-phenyl | CH₃ | CH₃ | H |
| 26 | 4-Cl-phenyl | CH₃ | CH₃ | H |
| 27 | 2-OH-phenyl | CH₃ | CH₃ | H |
| 28 | 3-OH-phenyl | CH₃ | CH₃ | H |
| 29 | 4-OH-phenyl | CH₃ | CH₃ | H |
| 30 | 2-OCH₃-phenyl | CH₃ | CH₃ | H |
| 31 | 3-OCH₃-phenyl | CH₃ | CH₃ | H |
| 32 | 4-OCH₃-phenyl | CH₃ | CH₃ | H |
| 33 | 2-OCF₃-phenyl | CH₃ | CH₃ | H |
| 34 | 3-OCF₃-phenyl | CH₃ | CH₃ | H |
| 35 | 4-OCF₃-phenyl | CH₃ | CH₃ | H |
| 36 | 2-OCHF₂-phenyl | CH₃ | CH₃ | H |
| 37 | 3-OCHF₂-phenyl | CH₃ | CH₃ | H |
| 38 | 4-OCHF₂-phenyl | CH₃ | CH₃ | H |
| 39 | 2-CF₃-phenyl | CH₃ | CH₃ | H |
| 40 | 3-CF₃-phenyl | CH₃ | CH₃ | H |
| 41 | 4-CF₃-phenyl | CH₃ | CH₃ | H |
| 42 | 2-CH₃-phenyl | CH₃ | CH₃ | H |
| 43 | 3-CH₃-phenyl | CH₃ | CH₃ | H |
| 44 | 4-CH₃-phenyl | CH₃ | CH₃ | H |
| 45 | 2-NO₂-phenyl | CH₃ | CH₃ | H |
| 46 | 3-NO₂-phenyl | CH₃ | CH₃ | H |
| 47 | 4-NO₂-phenyl | CH₃ | CH₃ | H |
| 48 | 2-pyridyl | CH₃ | CH₃ | H |
| 49 | 3-pyridyl | CH₃ | CH₃ | H |
| 50 | 4-pyridyl | CH₃ | CH₃ | H |
| 51 | cyclohexylamino | CH₃ | CH₃ | H |
| 52 | cyclopentylamino | CH₃ | CH₃ | H |
| 53 | H | OCH₃ | CH₃ | H |
| 54 | CH₃ | OCH₃ | CH₃ | H |
| 55 | C₂H₅ | OCH₃ | CH₃ | H |
| 56 | n-C₃H₇ | OCH₃ | CH₃ | H |
| 57 | i-C₃H₇ | OCH₃ | CH₃ | H |
| 58 | n-C₄H₉ | OCH₃ | CH₃ | H |
| 59 | s-C₄H₉ | OCH₃ | CH₃ | H |
| 60 | i-C₄H₉ | OCH₃ | CH₃ | H |
| 61 | t-C₄H₉ | OCH₃ | CH₃ | H |
| 62 | CH₂Cl | OCH₃ | CH₃ | H |
| 63 | CHCl₂ | OCH₃ | CH₃ | H |
| 64 | CCl₃ | OCH₃ | CH₃ | H |
| 65 | CH₂F | OCH₃ | CH₃ | H |
| 66 | CHF₂ | OCH₃ | CH₃ | H |
| 67 | CF₃ | OCH₃ | CH₃ | H |
| 68 | CH₂CF₃ | OCH₃ | CH₃ | H |
| 69 | CH₂OCH₃ | OCH₃ | CH₃ | H |
| 70 | CH₂OCH₂CH₃ | OCH₃ | CH₃ | H |
| 71 | CH₂NH₂ | OCH₃ | CH₃ | H |
| 72 | (CH₂)₂COCH₃ | OCH₃ | CH₃ | H |
| 73 | phenyl | OCH₃ | CH₃ | H |
| 74 | 2-F-phenyl | OCH₃ | CH₃ | H |
| 75 | 3-F-phenyl | OCH₃ | CH₃ | H |
| 76 | 4-F-phenyl | OCH₃ | CH₃ | H |
| 77 | 2-Cl-phenyl | OCH₃ | CH₃ | H |
| 78 | 3-Cl-phenyl | OCH₃ | CH₃ | H |
| 79 | 4-Cl-phenyl | OCH₃ | CH₃ | H |
| 80 | 2-OH-phenyl | OCH₃ | CH₃ | H |
| 81 | 3-OH-phenyl | OCH₃ | CH₃ | H |
| 82 | 4-OH-phenyl | OCH₃ | CH₃ | H |
| 83 | 2-OCH₃-phenyl | OCH₃ | CH₃ | H |
| 84 | 3-OCH₃-phenyl | OCH₃ | CH₃ | H |
| 85 | 4-OCH₃-phenyl | OCH₃ | CH₃ | H |
| 86 | 2-OCF₃-phenyl | OCH₃ | CH₃ | H |
| 87 | 3-OCF₃-phenyl | OCH₃ | CH₃ | H |
| 88 | 4-OCF₃-phenyl | OCH₃ | CH₃ | H |
| 89 | 2-OCHF₂-phenyl | OCH₃ | CH₃ | H |
| 90 | 3-OCHF₂-phenyl | OCH₃ | CH₃ | H |
| 91 | 4-OCHF₂-phenyl | OCH₃ | CH₃ | H |
| 92 | 2-CF₃-phenyl | OCH₃ | CH₃ | H |
| 93 | 3-CF₃-phenyl | OCH₃ | CH₃ | H |
| 94 | 4-CF₃-phenyl | OCH₃ | CH₃ | H |
| 95 | 2-CH₃-phenyl | OCH₃ | CH₃ | H |
| 96 | 3-CH₃-phenyl | OCH₃ | CH₃ | H |
| 97 | 4-CH₃-phenyl | OCH₃ | CH₃ | H |
| 98 | 2-NO₂-phenyl | OCH₃ | CH₃ | H |
| 99 | 3-NO₂-phenyl | OCH₃ | CH₃ | H |
| 00 | 4-NO₂-phenyl | OCH₃ | CH₃ | H |
| 101 | 2-pyridyl | OCH₃ | CH₃ | H |
| 102 | 3-pyridyl | OCH₃ | CH₃ | H |
| 103 | 4-pyridyl | OCH₃ | CH₃ | H |
| 104 | cyclohexylamino | OCH₃ | CH₃ | H |
| 105 | cyclopentylamino | OCH₃ | CH₃ | H |
| 106 | H | Cl | CH₃ | H |
| 107 | CH₃ | Cl | CH₃ | H |
| 108 | C₂H₅ | Cl | CH₃ | H |
| 109 | n-C₃H₇ | Cl | CH₃ | H |
| 110 | i-C₃H₇ | Cl | CH₃ | H |
| 111 | n-C₄H₉ | Cl | CH₃ | H |
| 112 | s-C₄H₉ | Cl | CH₃ | H |
| 113 | i-C₄H₉ | Cl | CH₃ | H |
| 114 | t-C₄H₉ | Cl | CH₃ | H |
| 115 | CH₂Cl | Cl | CH₃ | H |
| 116 | CHCl₂ | Cl | CH₃ | H |
| 117 | CCl₃ | Cl | CH₃ | H |
| 118 | CH₂F | Cl | CH₃ | H |
| 119 | CHF₂ | Cl | CH₃ | H |
| 120 | CF₃ | Cl | CH₃ | H |
| 121 | CH₂CF₃ | Cl | CH₃ | H |
| 122 | CH₂OCH₃ | Cl | CH₃ | H |
| 123 | CH₂OCH₂CH₃ | Cl | CH₃ | H |
| 124 | CH₂NH₂ | Cl | CH₃ | H |
| 125 | (CH₂)₂COCH₃ | Cl | CH₃ | H |
| 126 | phenyl | Cl | CH₃ | H |
| 127 | 2-F-phenyl | Cl | CH₃ | H |
| 128 | 3-F-phenyl | Cl | CH₃ | H |
| 129 | 4-F-phenyl | Cl | CH₃ | H |
| 130 | 2-Cl-phenyl | Cl | CH₃ | H |
| 131 | 3-Cl-phenyl | Cl | CH₃ | H |
| 132 | 4-Cl-phenyl | Cl | CH₃ | H |
| 133 | 2-OH-phenyl | Cl | CH₃ | H |
| 134 | 3-OH-phenyl | Cl | CH₃ | H |
| 135 | 4-OH-phenyl | Cl | CH₃ | H |
| 136 | 2-OCH₃-phenyl | Cl | CH₃ | H |
| 137 | 3-OCH₃-phenyl | Cl | CH₃ | H |
| 138 | 4-OCH₃-phenyl | Cl | CH₃ | H |
| 139 | 2-OCF₃-phenyl | Cl | CH₃ | H |
| 140 | 3-OCF₃-phenyl | Cl | CH₃ | H |
| 141 | 4-OCF₃-phenyl | Cl | CH₃ | H |
| 142 | 2-OCHF₂-phenyl | Cl | CH₃ | H |
| 143 | 3-OCHF₂-phenyl | Cl | CH₃ | H |
| 144 | 4-OCHF₂-phenyl | Cl | CH₃ | H |
| 145 | 2-CF₃-phenyl | Cl | CH₃ | H |
| 146 | 3-CF₃-phenyl | Cl | CH₃ | H |
| 147 | 4-CF₃-phenyl | Cl | CH₃ | H |
| 148 | 2-CH₃-phenyl | Cl | CH₃ | H |
| 149 | 3-CH₃-phenyl | Cl | CH₃ | H |
| 150 | 4-CH₃-phenyl | Cl | CH₃ | H |
| 151 | 2-NO₂-phenyl | Cl | CH₃ | H |
| 152 | 3-NO₂-phenyl | Cl | CH₃ | H |
| 153 | 4-NO₂-phenyl | Cl | CH₃ | H |
| 154 | 2-pyridyl | Cl | CH₃ | H |

TABLE B-continued

| | R³ | R¹ | R² | R⁴ |
|---|---|---|---|---|
| 155 | 3-pyridyl | Cl | $CH_3$ | H |
| 156 | 4-pyridyl | Cl | $CH_3$ | H |
| 157 | cyclohexylamino | Cl | $CH_3$ | H |
| 158 | cyclopentylamino | Cl | $CH_3$ | H |
| 159 | $CH_3$ | $CH_3$ | H | H |
| 160 | $C_2H_5$ | $CH_3$ | H | H |
| 161 | n-$C_3H_7$ | $CH_3$ | H | H |
| 162 | i-$C_3H_7$ | $CH_3$ | H | H |
| 163 | n-$C_4H_9$ | $CH_3$ | H | H |
| 164 | s-$C_4H_9$ | $CH_3$ | H | H |
| 165 | i-$C_4H_9$ | $CH_3$ | H | H |
| 166 | t-$C_4H_9$ | $CH_3$ | H | H |
| 167 | $CH_2Cl$ | $CH_3$ | H | H |
| 168 | $CHCl_2$ | $CH_3$ | H | H |
| 169 | $CCl_3$ | $CH_3$ | H | H |
| 170 | $CH_2F$ | $CH_3$ | H | H |
| 171 | $CHF_2$ | $CH_3$ | H | H |
| 172 | $CF_3$ | $CH_3$ | H | H |
| 173 | $CH_2CF_3$ | $CH_3$ | H | H |
| 174 | $CH_2OCH_3$ | $CH_3$ | H | H |
| 175 | $CH_2OCH_2CH_3$ | $CH_3$ | H | H |
| 176 | $CH_2NH_2$ | $CH_3$ | H | H |
| 177 | $(CH_2)_2COCH_3$ | $CH_3$ | H | H |
| 178 | phenyl | $CH_3$ | H | H |
| 179 | 2-F-phenyl | $CH_3$ | H | H |
| 180 | 3-F-phenyl | $CH_3$ | H | H |
| 181 | 4-F-phenyl | $CH_3$ | H | H |
| 182 | 2-Cl-phenyl | $CH_3$ | H | H |
| 183 | 3-Cl-phenyl | $CH_3$ | H | H |
| 184 | 4-Cl-phenyl | $CH_3$ | H | H |
| 185 | 2-OH-phenyl | $CH_3$ | H | H |
| 186 | 3-OH-phenyl | $CH_3$ | H | H |
| 187 | 4-OH-phenyl | $CH_3$ | H | H |
| 188 | 2-$OCH_3$-phenyl | $CH_3$ | H | H |
| 189 | 3-$OCH_3$-phenyl | $CH_3$ | H | H |
| 190 | 4-$OCH_3$-phenyl | $CH_3$ | H | H |
| 191 | 2-$OCF_3$-phenyl | $CH_3$ | H | H |
| 192 | 3-$OCF_3$-phenyl | $CH_3$ | H | H |
| 193 | 4-$OCF_3$-phenyl | $CH_3$ | H | H |
| 194 | 2-$OCHF_2$-phenyl | $CH_3$ | H | H |
| 195 | 3-$OCHF_2$-phenyl | $CH_3$ | H | H |
| 196 | 4-$OCHF_2$-phenyl | $CH_3$ | H | H |
| 197 | 2-$CF_3$-phenyl | $CH_3$ | H | H |
| 198 | 3-$CF_3$-phenyl | $CH_3$ | H | H |
| 199 | 4-$CF_3$-phenyl | $CH_3$ | H | H |
| 200 | 2-$CH_3$-phenyl | $CH_3$ | H | H |
| 201 | 3-$CH_3$-phenyl | $CH_3$ | H | H |
| 202 | 4-$CH_3$-phenyl | $CH_3$ | H | H |
| 203 | 2-$NO_2$-phenyl | $CH_3$ | H | H |
| 204 | 3-$NO_2$-phenyl | $CH_3$ | H | H |
| 205 | 4-$NO_2$-phenyl | $CH_3$ | H | H |
| 206 | 2-pyridyl | $CH_3$ | H | H |
| 207 | 3-pyridyl | $CH_3$ | H | H |
| 208 | 4-pyridyl | $CH_3$ | H | H |
| 209 | cyclohexylamino | $CH_3$ | H | H |
| 210 | cyclopentylamino | $CH_3$ | H | H |
| 211 | H | $OCH_3$ | H | H |
| 212 | $CH_3$ | $OCH_3$ | H | H |
| 213 | $C_2H_5$ | $OCH_3$ | H | H |
| 214 | n-$C_3H_7$ | $OCH_3$ | H | H |
| 215 | i-$C_3H_7$ | $OCH_3$ | H | H |
| 216 | n-$C_4H_9$ | $OCH_3$ | H | H |
| 217 | s-$C_4H_9$ | $OCH_3$ | H | H |
| 218 | i-$C_4H_9$ | $OCH_3$ | H | H |
| 219 | t-$C_4H_9$ | $OCH_3$ | H | H |
| 220 | $CH_2Cl$ | $OCH_3$ | H | H |
| 221 | $CHCl_2$ | $OCH_3$ | H | H |
| 222 | $CCl_3$ | $OCH_3$ | H | H |
| 223 | $CH_2F$ | $OCH_3$ | H | H |
| 224 | $CHF_2$ | $OCH_3$ | H | H |
| 225 | $CF_3$ | $OCH_3$ | H | H |
| 226 | $CH_2CF_3$ | $OCH_3$ | H | H |
| 227 | $CH_2OCH_3$ | $OCH_3$ | H | H |
| 228 | $CH_2OCH_2CH_3$ | $OCH_3$ | H | H |
| 229 | $CH_2NH_2$ | $OCH_3$ | H | H |
| 230 | $(CH_2)_2COCH_3$ | $OCH_3$ | H | H |
| 231 | phenyl | $OCH_3$ | H | H |
| 232 | 2-F-phenyl | $OCH_3$ | H | H |
| 233 | 3-F-phenyl | $OCH_3$ | H | H |
| 234 | 4-F-phenyl | $OCH_3$ | H | H |
| 235 | 2-Cl-phenyl | $OCH_3$ | H | H |
| 236 | 3-Cl-phenyl | $OCH_3$ | H | H |
| 237 | 4-Cl-phenyl | $OCH_3$ | H | H |
| 238 | 2-OH-phenyl | $OCH_3$ | H | H |
| 239 | 3-OH-phenyl | $OCH_3$ | H | H |
| 240 | 4-OH-phenyl | $OCH_3$ | H | H |
| 241 | 2-$OCH_3$-phenyl | $OCH_3$ | H | H |
| 242 | 3-$OCH_3$-phenyl | $OCH_3$ | H | H |
| 243 | 4-$OCH_3$-phenyl | $OCH_3$ | H | H |
| 244 | 2-$OCF_3$-phenyl | $OCH_3$ | H | H |
| 245 | 3-$OCF_3$-phenyl | $OCH_3$ | H | H |
| 246 | 4-$OCF_3$-phenyl | $OCH_3$ | H | H |
| 247 | 2-$OCHF_2$-phenyl | $OCH_3$ | H | H |
| 248 | 3-$OCHF_2$-phenyl | $OCH_3$ | H | H |
| 249 | 4-$OCHF_2$-phenyl | $OCH_3$ | H | H |
| 250 | 2-$CF_3$-phenyl | $OCH_3$ | H | H |
| 251 | 3-$CF_3$-phenyl | $OCH_3$ | H | H |
| 252 | 4-$CF_3$-phenyl | $OCH_3$ | H | H |
| 253 | 2-$CH_3$-phenyl | $OCH_3$ | H | H |
| 254 | 3-$CH_3$-phenyl | $OCH_3$ | H | H |
| 255 | 4-$CH_3$-phenyl | $OCH_3$ | H | H |
| 256 | 2-$NO_2$-phenyl | $OCH_3$ | H | H |
| 257 | 3-$NO_2$-phenyl | $OCH_3$ | H | H |
| 258 | 4-$NO_2$-phenyl | $OCH_3$ | H | H |
| 259 | 2-pyridyl | $OCH_3$ | H | H |
| 260 | 3-pyridyl | $OCH_3$ | H | H |
| 261 | 4-pyridyl | $OCH_3$ | H | H |
| 262 | cyclohexylamino | $OCH_3$ | H | H |
| 263 | cyclopentylamino | $OCH_3$ | H | H |
| 264 | H | Cl | H | H |
| 265 | $CH_3$ | Cl | H | H |
| 266 | $C_2H_5$ | Cl | H | H |
| 267 | n-$C_3H_7$ | Cl | H | H |
| 268 | i-$C_3H_7$ | Cl | H | H |
| 269 | n-$C_4H_9$ | Cl | H | H |
| 270 | s-$C_4H_9$ | Cl | H | H |
| 271 | i-$C_4H_9$ | Cl | H | H |
| 272 | t-$C_4H_9$ | Cl | H | H |
| 273 | $CH_2Cl$ | Cl | H | H |
| 274 | $CHCl_2$ | Cl | H | H |
| 275 | $CCl_3$ | Cl | H | H |
| 276 | $CH_2F$ | Cl | H | H |
| 277 | $CHF_2$ | Cl | H | H |
| 278 | $CF_3$ | Cl | H | H |
| 279 | $CH_2CF_3$ | Cl | H | H |
| 280 | $CH_2OCH_3$ | Cl | H | H |
| 281 | $CH_2OCH_2CH_3$ | Cl | H | H |
| 282 | $CH_2NH_2$ | Cl | H | H |
| 283 | $(CH_2)_2COCH_3$ | Cl | H | H |
| 284 | phenyl | Cl | H | H |
| 285 | 2-F-phenyl | Cl | H | H |
| 286 | 3-F-phenyl | Cl | H | H |
| 287 | 4-F-phenyl | Cl | H | H |
| 288 | 2-Cl-phenyl | Cl | H | H |
| 289 | 3-Cl-phenyl | Cl | H | H |
| 290 | 4-Cl-phenyl | Cl | H | H |
| 291 | 2-OH-phenyl | Cl | H | H |
| 292 | 3-OH-phenyl | Cl | H | H |
| 293 | 4-OH-phenyl | Cl | H | H |
| 294 | 2-$OCH_3$-phenyl | Cl | H | H |
| 295 | 3-$OCH_3$-phenyl | Cl | H | H |
| 296 | 4-$OCH_3$-phenyl | Cl | H | H |
| 297 | 2-$OCF_3$-phenyl | Cl | H | H |
| 298 | 3-$OCF_3$-phenyl | Cl | H | H |
| 299 | 4-$OCF_3$-phenyl | Cl | H | H |
| 300 | 2-$OCHF_2$-phenyl | Cl | H | H |
| 301 | 3-$OCHF_2$-phenyl | Cl | H | H |
| 302 | 4-$OCHF_2$-phenyl | Cl | H | H |
| 303 | 2-$CF_3$-phenyl | Cl | H | H |
| 304 | 3-$CF_3$-phenyl | Cl | H | H |
| 305 | 4-$CF_3$-phenyl | Cl | H | H |
| 306 | 2-$CH_3$-phenyl | Cl | H | H |
| 307 | 3-$CH_3$-phenyl | Cl | H | H |
| 308 | 4-$CH_3$-phenyl | Cl | H | H |

TABLE B-continued

| | R³ | R¹ | R² | R⁴ |
|---|---|---|---|---|
| 309 | 2-NO₂-phenyl | Cl | H | H |
| 310 | 3-NO₂-phenyl | Cl | H | H |
| 311 | 4-NO₂-phenyl | Cl | H | H |
| 312 | 2-pyridyl | Cl | H | H |
| 313 | 3-pyridyl | Cl | H | H |
| 314 | 4-pyridyl | Cl | H | H |
| 315 | cyclohexylamino | Cl | H | H |
| 316 | cyclopentylamino | Cl | H | H |
| 317 | CH₃ | CH₃ | CH₃ | CH₃ |
| 318 | C₂H₅ | CH₃ | CH₃ | CH₃ |
| 319 | n-C₃H₇ | CH₃ | CH₃ | CH₃ |
| 320 | i-C₃H₇ | CH₃ | CH₃ | CH₃ |
| 321 | n-C₄H₉ | CH₃ | CH₃ | CH₃ |
| 322 | s-C₄H₉ | CH₃ | CH₃ | CH₃ |
| 323 | i-C₄H₉ | CH₃ | CH₃ | CH₃ |
| 324 | t-C₄H₉ | CH₃ | CH₃ | CH₃ |
| 325 | CH₂Cl | CH₃ | CH₃ | CH₃ |
| 326 | CHCl₂ | CH₃ | CH₃ | CH₃ |
| 327 | CCl₃ | CH₃ | CH₃ | CH₃ |
| 328 | CH₂F | CH₃ | CH₃ | CH₃ |
| 329 | CHF₂ | CH₃ | CH₃ | CH₃ |
| 330 | CF₃ | CH₃ | CH₃ | CH₃ |
| 331 | CH₂CF₃ | CH₃ | CH₃ | CH₃ |
| 332 | CH₂OCH₃ | CH₃ | CH₃ | CH₃ |
| 333 | CH₂OCH₂CH₃ | CH₃ | CH₃ | CH₃ |
| 334 | CH₂NH₂ | CH₃ | CH₃ | CH₃ |
| 335 | (CH₂)₂COCH₃ | CH₃ | CH₃ | CH₃ |
| 336 | phenyl | CH₃ | CH₃ | CH₃ |
| 337 | 2-F-phenyl | CH₃ | CH₃ | CH₃ |
| 338 | 3-F-phenyl | CH₃ | CH₃ | CH₃ |
| 339 | 4-F-phenyl | CH₃ | CH₃ | CH₃ |
| 340 | 2-Cl-phenyl | CH₃ | CH₃ | CH₃ |
| 341 | 3-Cl-phenyl | CH₃ | CH₃ | CH₃ |
| 342 | 4-Cl-phenyl | CH₃ | CH₃ | CH₃ |
| 343 | 2-OH-phenyl | CH₃ | CH₃ | CH₃ |
| 344 | 3-OH-phenyl | CH₃ | CH₃ | CH₃ |
| 345 | 4-OH-phenyl | CH₃ | CH₃ | CH₃ |
| 346 | 2-OCH₃-phenyl | CH₃ | CH₃ | CH₃ |
| 347 | 3-OCH₃-phenyl | CH₃ | CH₃ | CH₃ |
| 348 | 4-OCH₃-phenyl | CH₃ | CH₃ | CH₃ |
| 349 | 2-OCF₃-phenyl | CH₃ | CH₃ | CH₃ |
| 350 | 3-OCF₃-phenyl | CH₃ | CH₃ | CH₃ |
| 351 | 4-OCF₃-phenyl | CH₃ | CH₃ | CH₃ |
| 352 | 2-OCHF₂-phenyl | CH₃ | CH₃ | CH₃ |
| 353 | 3-OCHF₂-phenyl | CH₃ | CH₃ | CH₃ |
| 354 | 4-OCHF₂-phenyl | CH₃ | CH₃ | CH₃ |
| 355 | 2-CF₃-phenyl | CH₃ | CH₃ | CH₃ |
| 356 | 3-CF₃-phenyl | CH₃ | CH₃ | CH₃ |
| 357 | 4-CF₃-phenyl | CH₃ | CH₃ | CH₃ |
| 358 | 2-CH₃-phenyl | CH₃ | CH₃ | CH₃ |
| 359 | 3-CH₃-phenyl | CH₃ | CH₃ | CH₃ |
| 360 | 4-CH₃-phenyl | CH₃ | CH₃ | CH₃ |
| 361 | 2-NO₂-phenyl | CH₃ | CH₃ | CH₃ |
| 362 | 3-NO₂-phenyl | CH₃ | CH₃ | CH₃ |
| 363 | 4-NO₂-phenyl | CH₃ | CH₃ | CH₃ |
| 364 | 2-pyridyl | CH₃ | CH₃ | CH₃ |
| 365 | 3-pyridyl | CH₃ | CH₃ | CH₃ |
| 366 | 4-pyridyl | CH₃ | CH₃ | CH₃ |
| 367 | cyclohexylamino | CH₃ | CH₃ | CH₃ |
| 368 | cyclopentylamino | CH₃ | CH₃ | CH₃ |
| 369 | H | OCH₃ | CH₃ | CH₃ |
| 370 | CH₃ | OCH₃ | CH₃ | CH₃ |
| 371 | C₂H₅ | OCH₃ | CH₃ | CH₃ |
| 372 | n-C₃H₇ | OCH₃ | CH₃ | CH₃ |
| 373 | i-C₃H₇ | OCH₃ | CH₃ | CH₃ |
| 374 | n-C₄H₉ | OCH₃ | CH₃ | CH₃ |
| 375 | s-C₄H₉ | OCH₃ | CH₃ | CH₃ |
| 376 | i-C₄H₉ | OCH₃ | CH₃ | CH₃ |
| 377 | t-C₄H₉ | OCH₃ | CH₃ | CH₃ |
| 378 | CH₂Cl | OCH₃ | CH₃ | CH₃ |
| 379 | CHCl₂ | OCH₃ | CH₃ | CH₃ |
| 380 | CCl₃ | OCH₃ | CH₃ | CH₃ |
| 381 | CH₂F | OCH₃ | CH₃ | CH₃ |
| 382 | CHF₂ | OCH₃ | CH₃ | CH₃ |
| 383 | CF₃ | OCH₃ | CH₃ | CH₃ |
| 384 | CH₂CF₃ | OCH₃ | CH₃ | CH₃ |
| 385 | CH₂OCH₃ | OCH₃ | CH₃ | CH₃ |
| 386 | CH₂OCH₂CH₃ | OCH₃ | CH₃ | CH₃ |
| 387 | CH₂NH₂ | OCH₃ | CH₃ | CH₃ |
| 388 | (CH₂)₂COCH₃ | OCH₃ | CH₃ | CH₃ |
| 389 | phenyl | OCH₃ | CH₃ | CH₃ |
| 390 | 2-F-phenyl | OCH₃ | CH₃ | CH₃ |
| 391 | 3-F-phenyl | OCH₃ | CH₃ | CH₃ |
| 392 | 4-F-phenyl | OCH₃ | CH₃ | CH₃ |
| 393 | 2-Cl-phenyl | OCH₃ | CH₃ | CH₃ |
| 394 | 3-Cl-phenyl | OCH₃ | CH₃ | CH₃ |
| 395 | 4-Cl-phenyl | OCH₃ | CH₃ | CH₃ |
| 396 | 2-OH-phenyl | OCH₃ | CH₃ | CH₃ |
| 397 | 3-OH-phenyl | OCH₃ | CH₃ | CH₃ |
| 398 | 4-OH-phenyl | OCH₃ | CH₃ | CH₃ |
| 399 | 2-OCH₃-phenyl | OCH₃ | CH₃ | CH₃ |
| 400 | 3-OCH₃-phenyl | OCH₃ | CH₃ | CH₃ |
| 401 | 4-OCH₃-phenyl | OCH₃ | CH₃ | CH₃ |
| 402 | 2-OCF₃-phenyl | OCH₃ | CH₃ | CH₃ |
| 403 | 3-OCF₃-phenyl | OCH₃ | CH₃ | CH₃ |
| 404 | 4-OCF₃-phenyl | OCH₃ | CH₃ | CH₃ |
| 405 | 2-OCHF₂-phenyl | OCH₃ | CH₃ | CH₃ |
| 406 | 3-OCHF₂-phenyl | OCH₃ | CH₃ | CH₃ |
| 407 | 4-OCHF₂-phenyl | OCH₃ | CH₃ | CH₃ |
| 408 | 2-CF₃-phenyl | OCH₃ | CH₃ | CH₃ |
| 409 | 3-CF₃-phenyl | OCH₃ | CH₃ | CH₃ |
| 410 | 4-CF₃-phenyl | OCH₃ | CH₃ | CH₃ |
| 411 | 2-CH₃-phenyl | OCH₃ | CH₃ | CH₃ |
| 412 | 3-CH₃-phenyl | OCH₃ | CH₃ | CH₃ |
| 413 | 4-CH₃-phenyl | OCH₃ | CH₃ | CH₃ |
| 414 | 2-NO₂-phenyl | OCH₃ | CH₃ | CH₃ |
| 415 | 3-NO₂-phenyl | OCH₃ | CH₃ | CH₃ |
| 416 | 4-NO₂-phenyl | OCH₃ | CH₃ | CH₃ |
| 417 | 2-pyridyl | OCH₃ | CH₃ | CH₃ |
| 418 | 3-pyridyl | OCH₃ | CH₃ | CH₃ |
| 419 | 4-pyridyl | OCH₃ | CH₃ | CH₃ |
| 420 | cyclohexylamino | OCH₃ | CH₃ | CH₃ |
| 421 | cyclopentylamino | OCH₃ | CH₃ | CH₃ |
| 422 | H | Cl | CH₃ | CH₃ |
| 423 | CH₃ | Cl | CH₃ | CH₃ |
| 424 | C₂H₅ | Cl | CH₃ | CH₃ |
| 445 | n-C₃H₇ | Cl | CH₃ | CH₃ |
| 426 | i-C₃H₇ | Cl | CH₃ | CH₃ |
| 427 | n-C₄H₉ | Cl | CH₃ | CH₃ |
| 428 | s-C₄H₉ | Cl | CH₃ | CH₃ |
| 429 | i-C₄H₉ | Cl | CH₃ | CH₃ |
| 430 | t-C₄H₉ | Cl | CH₃ | CH₃ |
| 431 | CH₂Cl | Cl | CH₃ | CH₃ |
| 432 | CHCl₂ | Cl | CH₃ | CH₃ |
| 433 | CCl₃ | Cl | CH₃ | CH₃ |
| 434 | CH₂F | Cl | CH₃ | CH₃ |
| 435 | CHF₂ | Cl | CH₃ | CH₃ |
| 436 | CF₃ | Cl | CH₃ | CH₃ |
| 437 | CH₂CF₃ | Cl | CH₃ | CH₃ |
| 438 | CH₂OCH₃ | Cl | CH₃ | CH₃ |
| 439 | CH₂OCH₂CH₃ | Cl | CH₃ | CH₃ |
| 440 | CH₂NH₂ | Cl | CH₃ | CH₃ |
| 441 | (CH₂)₂COCH₃ | Cl | CH₃ | CH₃ |
| 442 | phenyl | Cl | CH₃ | CH₃ |
| 443 | 2-F-phenyl | Cl | CH₃ | CH₃ |
| 444 | 3-F-phenyl | Cl | CH₃ | CH₃ |
| 445 | 4-F-phenyl | Cl | CH₃ | CH₃ |
| 446 | 2-Cl-phenyl | Cl | CH₃ | CH₃ |
| 447 | 3-Cl-phenyl | Cl | CH₃ | CH₃ |
| 448 | 4-Cl-phenyl | Cl | CH₃ | CH₃ |
| 449 | 2-OH-phenyl | Cl | CH₃ | CH₃ |
| 450 | 3-OH-phenyl | Cl | CH₃ | CH₃ |
| 451 | 4-OH-phenyl | Cl | CH₃ | CH₃ |
| 452 | 2-OCH₃-phenyl | Cl | CH₃ | CH₃ |
| 453 | 3-OCH₃-phenyl | Cl | CH₃ | CH₃ |
| 454 | 4-OCH₃-phenyl | Cl | CH₃ | CH₃ |
| 455 | 2-OCF₃-phenyl | Cl | CH₃ | CH₃ |
| 456 | 3-OCF₃-phenyl | Cl | CH₃ | CH₃ |
| 457 | 4-OCF₃-phenyl | Cl | CH₃ | CH₃ |
| 458 | 2-OCHF₂-phenyl | Cl | CH₃ | CH₃ |
| 459 | 3-OCHF₂-phenyl | Cl | CH₃ | CH₃ |
| 460 | 4-OCHF₂-phenyl | Cl | CH₃ | CH₃ |
| 461 | 2-CF₃-phenyl | Cl | CH₃ | CH₃ |
| 462 | 3-CF₃-phenyl | Cl | CH₃ | CH₃ |

TABLE B-continued

| | R³ | R¹ | R² | R⁴ |
|---|---|---|---|---|
| 463 | 4-CF₃-phenyl | Cl | CH₃ | CH₃ |
| 464 | 2-CH₃-phenyl | Cl | CH₃ | CH₃ |
| 465 | 3-CH₃-phenyl | Cl | CH₃ | CH₃ |
| 466 | 4-CH₃-phenyl | Cl | CH₃ | CH₃ |
| 467 | 2-NO₂-phenyl | Cl | CH₃ | CH₃ |
| 468 | 3-NO₂-phenyl | Cl | CH₃ | CH₃ |
| 469 | 4-NO₂-phenyl | Cl | CH₃ | CH₃ |
| 470 | 2-pyridyl | Cl | CH₃ | CH₃ |
| 471 | 3-pyridyl | Cl | CH₃ | CH₃ |
| 472 | 4-pyridyl | Cl | CH₃ | CH₃ |
| 473 | cyclohexylamino | Cl | CH₃ | CH₃ |
| 474 | cyclopentylamino | Cl | CH₃ | CH₃ |
| 475 | CH₃ | CH₃ | H | CH₃ |
| 476 | C₂H₅ | CH₃ | H | CH₃ |
| 477 | n-C₃H₇ | CH₃ | H | CH₃ |
| 478 | i-C₃H₇ | CH₃ | H | CH₃ |
| 479 | n-C₄H₉ | CH₃ | H | CH₃ |
| 480 | s-C₄H₉ | CH₃ | H | CH₃ |
| 481 | i-C₄H₉ | CH₃ | H | CH₃ |
| 482 | t-C₄H₉ | CH₃ | H | CH₃ |
| 483 | CH₂Cl | CH₃ | H | CH₃ |
| 484 | CHCl₂ | CH₃ | H | CH₃ |
| 485 | CCl₃ | CH₃ | H | CH₃ |
| 486 | CH₂F | CH₃ | H | CH₃ |
| 487 | CHF₂ | CH₃ | H | CH₃ |
| 488 | CF₃ | CH₃ | H | CH₃ |
| 489 | CH₂CF₃ | CH₃ | H | CH₃ |
| 490 | CH₂OCH₃ | CH₃ | H | CH₃ |
| 491 | CH₂OCH₂CH₃ | CH₃ | H | CH₃ |
| 492 | CH₂NH₂ | CH₃ | H | CH₃ |
| 493 | (CH₂)₂COCH₃ | CH₃ | H | CH₃ |
| 494 | phenyl | CH₃ | H | CH₃ |
| 495 | 2-F-phenyl | CH₃ | H | CH₃ |
| 496 | 3-F-phenyl | CH₃ | H | CH₃ |
| 497 | 4-F-phenyl | CH₃ | H | CH₃ |
| 498 | 2-Cl-phenyl | CH₃ | H | CH₃ |
| 499 | 3-Cl-phenyl | CH₃ | H | CH₃ |
| 500 | 4-Cl-phenyl | CH₃ | H | CH₃ |
| 501 | 2-OH-phenyl | CH₃ | H | CH₃ |
| 502 | 3-OH-phenyl | CH₃ | H | CH₃ |
| 503 | 4-OH-phenyl | CH₃ | H | CH₃ |
| 504 | 2-OCH₃-phenyl | CH₃ | H | CH₃ |
| 505 | 3-OCH₃-phenyl | CH₃ | H | CH₃ |
| 506 | 4-OCH₃-phenyl | CH₃ | H | CH₃ |
| 507 | 2-OCF₃-phenyl | CH₃ | H | CH₃ |
| 508 | 3-OCF₃-phenyl | CH₃ | H | CH₃ |
| 509 | 4-OCF₃-phenyl | CH₃ | H | CH₃ |
| 510 | 2-OCHF₂-phenyl | CH₃ | H | CH₃ |
| 511 | 3-OCHF₂-phenyl | CH₃ | H | CH₃ |
| 512 | 4-OCHF₂-phenyl | CH₃ | H | CH₃ |
| 513 | 2-CF₃-phenyl | CH₃ | H | CH₃ |
| 514 | 3-CF₃-phenyl | CH₃ | H | CH₃ |
| 515 | 4-CF₃-phenyl | CH₃ | H | CH₃ |
| 516 | 2-CH₃-phenyl | CH₃ | H | CH₃ |
| 517 | 3-CH₃-phenyl | CH₃ | H | CH₃ |
| 518 | 4-CH₃-phenyl | CH₃ | H | CH₃ |
| 519 | 2-NO₂-phenyl | CH₃ | H | CH₃ |
| 520 | 3-NO₂-phenyl | CH₃ | H | CH₃ |
| 521 | 4-NO₂-phenyl | CH₃ | H | CH₃ |
| 522 | 2-pyridyl | CH₃ | H | CH₃ |
| 523 | 3-pyridyl | CH₃ | H | CH₃ |
| 524 | 4-pyridyl | CH₃ | H | CH₃ |
| 525 | cyclohexylamino | CH₃ | H | CH₃ |
| 526 | cyclopentylamino | CH₃ | H | CH₃ |
| 527 | H | OCH₃ | H | CH₃ |
| 528 | CH₃ | OCH₃ | H | CH₃ |
| 529 | C₂H₅ | OCH₃ | H | CH₃ |
| 530 | n-C₃H₇ | OCH₃ | H | CH₃ |
| 531 | i-C₃H₇ | OCH₃ | H | CH₃ |
| 532 | n-C₄H₉ | OCH₃ | H | CH₃ |
| 533 | s-C₄H₉ | OCH₃ | H | CH₃ |
| 534 | i-C₄H₉ | OCH₃ | H | CH₃ |
| 535 | t-C₄H₉ | OCH₃ | H | CH₃ |
| 536 | CH₂Cl | OCH₃ | H | CH₃ |
| 537 | CHCl₂ | OCH₃ | H | CH₃ |
| 538 | CCl₃ | OCH₃ | H | CH₃ |
| 539 | CH₂F | OCH₃ | H | CH₃ |
| 540 | CHF₂ | OCH₃ | H | CH₃ |
| 541 | CF₃ | OCH₃ | H | CH₃ |
| 542 | CH₂CF₃ | OCH₃ | H | CH₃ |
| 543 | CH₂OCH₃ | OCH₃ | H | CH₃ |
| 544 | CH₂OCH₂CH₃ | OCH₃ | H | CH₃ |
| 545 | CH₂NH₂ | OCH₃ | H | CH₃ |
| 546 | (CH₂)₂COCH₃ | OCH₃ | H | CH₃ |
| 547 | phenyl | OCH₃ | H | CH₃ |
| 548 | 2-F-phenyl | OCH₃ | H | CH₃ |
| 549 | 3-F-phenyl | OCH₃ | H | CH₃ |
| 550 | 4-F-phenyl | OCH₃ | H | CH₃ |
| 551 | 2-Cl-phenyl | OCH₃ | H | CH₃ |
| 552 | 3-Cl-phenyl | OCH₃ | H | CH₃ |
| 553 | 4-Cl-phenyl | OCH₃ | H | CH₃ |
| 554 | 2-OH-phenyl | OCH₃ | H | CH₃ |
| 555 | 3-OH-phenyl | OCH₃ | H | CH₃ |
| 556 | 4-OH-phenyl | OCH₃ | H | CH₃ |
| 557 | 2-OCH₃-phenyl | OCH₃ | H | CH₃ |
| 558 | 3-OCH₃-phenyl | OCH₃ | H | CH₃ |
| 559 | 4-OCH₃-phenyl | OCH₃ | H | CH₃ |
| 560 | 2-OCF₃-phenyl | OCH₃ | H | CH₃ |
| 561 | 3-OCF₃-phenyl | OCH₃ | H | CH₃ |
| 562 | 4-OCF₃-phenyl | OCH₃ | H | CH₃ |
| 563 | 2-OCHF₂-phenyl | OCH₃ | H | CH₃ |
| 564 | 3-OCHF₂-phenyl | OCH₃ | H | CH₃ |
| 565 | 4-OCHF₂-phenyl | OCH₃ | H | CH₃ |
| 566 | 2-CF₃-phenyl | OCH₃ | H | CH₃ |
| 567 | 3-CF₃-phenyl | OCH₃ | H | CH₃ |
| 568 | 4-CF₃-phenyl | OCH₃ | H | CH₃ |
| 569 | 2-CH₃-phenyl | OCH₃ | H | CH₃ |
| 570 | 3-CH₃-phenyl | OCH₃ | H | CH₃ |
| 571 | 4-CH₃-phenyl | OCH₃ | H | CH₃ |
| 572 | 2-NO₂-phenyl | OCH₃ | H | CH₃ |
| 573 | 3-NO₂-phenyl | OCH₃ | H | CH₃ |
| 574 | 4-NO₂-phenyl | OCH₃ | H | CH₃ |
| 575 | 2-pyridyl | OCH₃ | H | CH₃ |
| 576 | 3-pyridyl | OCH₃ | H | CH₃ |
| 577 | 4-pyridyl | OCH₃ | H | CH₃ |
| 578 | cyclohexylamino | OCH₃ | H | CH₃ |
| 579 | cyclopentylamino | OCH₃ | H | CH₃ |
| 580 | H | Cl | H | CH₃ |
| 581 | CH₃ | Cl | H | CH₃ |
| 582 | C₂H₅ | Cl | H | CH₃ |
| 583 | n-C₃H₇ | Cl | H | CH₃ |
| 584 | i-C₃H₇ | Cl | H | CH₃ |
| 585 | n-C₄H₉ | Cl | H | CH₃ |
| 586 | s-C₄H₉ | Cl | H | CH₃ |
| 587 | i-C₄H₉ | Cl | H | CH₃ |
| 588 | t-C₄H₉ | Cl | H | CH₃ |
| 589 | CH₂Cl | Cl | H | CH₃ |
| 590 | CHCl₂ | Cl | H | CH₃ |
| 591 | CCl₃ | Cl | H | CH₃ |
| 592 | CH₂F | Cl | H | CH₃ |
| 593 | CHF₂ | Cl | H | CH₃ |
| 594 | CF₃ | Cl | H | CH₃ |
| 595 | CH₂CF₃ | Cl | H | CH₃ |
| 596 | CH₂OCH₃ | Cl | H | CH₃ |
| 597 | CH₂OCH₂CH₃ | Cl | H | CH₃ |
| 598 | CH₂NH₂ | Cl | H | CH₃ |
| 599 | (CH₂)₂COCH₃ | Cl | H | CH₃ |
| 600 | phenyl | Cl | H | CH₃ |
| 701 | 2-F-phenyl | Cl | H | CH₃ |
| 702 | 3-F-phenyl | Cl | H | CH₃ |
| 703 | 4-F-phenyl | Cl | H | CH₃ |
| 704 | 2-Cl-phenyl | Cl | H | CH₃ |
| 705 | 3-Cl-phenyl | Cl | H | CH₃ |
| 706 | 4-Cl-phenyl | Cl | H | CH₃ |
| 707 | 2-OH-phenyl | Cl | H | CH₃ |
| 708 | 3-OH-phenyl | Cl | H | CH₃ |
| 709 | 4-OH-phenyl | Cl | H | CH₃ |
| 710 | 2-OCH₃-phenyl | Cl | H | CH₃ |
| 711 | 3-OCH₃-phenyl | Cl | H | CH₃ |
| 712 | 4-OCH₃-phenyl | Cl | H | CH₃ |
| 713 | 2-OCF₃-phenyl | Cl | H | CH₃ |
| 714 | 3-OCF₃-phenyl | Cl | H | CH₃ |
| 715 | 4-OCF₃-phenyl | Cl | H | CH₃ |
| 716 | 2-OCHF₂-phenyl | Cl | H | CH₃ |

TABLE B-continued

| | R³ | R¹ | R² | R⁴ |
|---|---|---|---|---|
| 717 | 3-OCHF₂-phenyl | Cl | H | CH₃ |
| 718 | 4-OCHF₂-phenyl | Cl | H | CH₃ |
| 719 | 2-CF₃-phenyl | Cl | H | CH₃ |
| 720 | 3-CF₃-phenyl | Cl | H | CH₃ |
| 721 | 4-CF₃-phenyl | Cl | H | CH₃ |
| 722 | 2-CH₃-phenyl | Cl | H | CH₃ |
| 723 | 3-CH₃-phenyl | Cl | H | CH₃ |
| 724 | 4-CH₃-phenyl | Cl | H | CH₃ |
| 725 | 2-NO₂-phenyl | Cl | H | CH₃ |
| 726 | 3-NO₂-phenyl | Cl | H | CH₃ |
| 727 | 4-NO₂-phenyl | Cl | H | CH₃ |
| 728 | 2-pyridyl | Cl | H | CH₃ |
| 729 | 3-pyridyl | Cl | H | CH₃ |
| 730 | 4-pyridyl | Cl | H | CH₃ |
| 731 | cyclohexylamino | Cl | H | CH₃ |
| 732 | cyclopentylamino | Cl | H | CH₃ |
| 733 | CH₃ | CH₃ | CH₃ | C₂H₅ |
| 734 | C₂H₅ | CH₃ | CH₃ | C₂H₅ |
| 735 | n-C₃H₇ | CH₃ | CH₃ | C₂H₅ |
| 736 | i-C₃H₇ | CH₃ | CH₃ | C₂H₅ |
| 737 | n-C₄H₉ | CH₃ | CH₃ | C₂H₅ |
| 738 | s-C₄H₉ | CH₃ | CH₃ | C₂H₅ |
| 739 | i-C₄H₉ | CH₃ | CH₃ | C₂H₅ |
| 740 | t-C₄H₉ | CH₃ | CH₃ | C₂H₅ |
| 741 | CH₂Cl | CH₃ | CH₃ | C₂H₅ |
| 742 | CHCl₂ | CH₃ | CH₃ | C₂H₅ |
| 743 | CCl₃ | CH₃ | CH₃ | C₂H₅ |
| 744 | CH₂F | CH₃ | CH₃ | C₂H₅ |
| 745 | CHF₂ | CH₃ | CH₃ | C₂H₅ |
| 746 | CF₃ | CH₃ | CH₃ | C₂H₅ |
| 747 | CH₂CF₃ | CH₃ | CH₃ | C₂H₅ |
| 748 | CH₂OCH₃ | CH₃ | CH₃ | C₂H₅ |
| 749 | CH₂OCH₂CH₃ | CH₃ | CH₃ | C₂H₅ |
| 750 | CH₂NH₂ | CH₃ | CH₃ | C₂H₅ |
| 751 | (CH₂)₂COCH₃ | CH₃ | CH₃ | C₂H₅ |
| 752 | phenyl | CH₃ | CH₃ | C₂H₅ |
| 753 | 2-F-phenyl | CH₃ | CH₃ | C₂H₅ |
| 754 | 3-F-phenyl | CH₃ | CH₃ | C₂H₅ |
| 755 | 4-F-phenyl | CH₃ | CH₃ | C₂H₅ |
| 756 | 2-Cl-phenyl | CH₃ | CH₃ | C₂H₅ |
| 757 | 3-Cl-phenyl | CH₃ | CH₃ | C₂H₅ |
| 758 | 4-Cl-phenyl | CH₃ | CH₃ | C₂H₅ |
| 759 | 2-OH-phenyl | CH₃ | CH₃ | C₂H₅ |
| 760 | 3-OH-phenyl | CH₃ | CH₃ | C₂H₅ |
| 761 | 4-OH-phenyl | CH₃ | CH₃ | C₂H₅ |
| 762 | 2-OCH₃-phenyl | CH₃ | CH₃ | C₂H₅ |
| 763 | 3-OCH₃-phenyl | CH₃ | CH₃ | C₂H₅ |
| 764 | 4-OCH₃-phenyl | CH₃ | CH₃ | C₂H₅ |
| 765 | 2-OCF₃-phenyl | CH₃ | CH₃ | C₂H₅ |
| 766 | 3-OCF₃-phenyl | CH₃ | CH₃ | C₂H₅ |
| 767 | 4-OCF₃-phenyl | CH₃ | CH₃ | C₂H₅ |
| 768 | 2-OCHF₂-phenyl | CH₃ | CH₃ | C₂H₅ |
| 769 | 3-OCHF₂-phenyl | CH₃ | CH₃ | C₂H₅ |
| 770 | 4-OCHF₂-phenyl | CH₃ | CH₃ | C₂H₅ |
| 771 | 2-CF₃-phenyl | CH₃ | CH₃ | C₂H₅ |
| 772 | 3-CF₃-phenyl | CH₃ | CH₃ | C₂H₅ |
| 773 | 4-CF₃-phenyl | CH₃ | CH₃ | C₂H₅ |
| 774 | 2-CH₃-phenyl | CH₃ | CH₃ | C₂H₅ |
| 775 | 3-CH₃-phenyl | CH₃ | CH₃ | C₂H₅ |
| 776 | 4-CH₃-phenyl | CH₃ | CH₃ | C₂H₅ |
| 777 | 2-NO₂-phenyl | CH₃ | CH₃ | C₂H₅ |
| 778 | 3-NO₂-phenyl | CH₃ | CH₃ | C₂H₅ |
| 779 | 4-NO₂-phenyl | CH₃ | CH₃ | C₂H₅ |
| 780 | 2-pyridyl | CH₃ | CH₃ | C₂H₅ |
| 781 | 3-pyridyl | CH₃ | CH₃ | C₂H₅ |
| 782 | 4-pyridyl | CH₃ | CH₃ | C₂H₅ |
| 783 | cyclohexylamino | CH₃ | CH₃ | C₂H₅ |
| 784 | cyclopentylamino | CH₃ | CH₃ | C₂H₅ |
| 785 | H | OCH₃ | CH₃ | C₂H₅ |
| 786 | CH₃ | OCH₃ | CH₃ | C₂H₅ |
| 787 | C₂H₅ | OCH₃ | CH₃ | C₂H₅ |
| 788 | n-C₃H₇ | OCH₃ | CH₃ | C₂H₅ |
| 789 | i-C₃H₇ | OCH₃ | CH₃ | C₂H₅ |
| 790 | n-C₄H₉ | OCH₃ | CH₃ | C₂H₅ |
| 791 | s-C₄H₉ | OCH₃ | CH₃ | C₂H₅ |
| 792 | i-C₄H₉ | OCH₃ | CH₃ | C₂H₅ |
| 793 | t-C₄H₉ | OCH₃ | CH₃ | C₂H₅ |
| 794 | CH₂Cl | OCH₃ | CH₃ | C₂H₅ |
| 795 | CHCl₂ | OCH₃ | CH₃ | C₂H₅ |
| 796 | CCl₃ | OCH₃ | CH₃ | C₂H₅ |
| 797 | CH₂F | OCH₃ | CH₃ | C₂H₅ |
| 798 | CHF₂ | OCH₃ | CH₃ | C₂H₅ |
| 799 | CF₃ | OCH₃ | CH₃ | C₂H₅ |
| 800 | CH₂CF₃ | OCH₃ | CH₃ | C₂H₅ |
| 801 | CH₂OCH₃ | OCH₃ | CH₃ | C₂H₅ |
| 802 | CH₂OCH₂CH₃ | OCH₃ | CH₃ | C₂H₅ |
| 803 | CH₂NH₂ | OCH₃ | CH₃ | C₂H₅ |
| 804 | (CH₂)₂COCH₃ | OCH₃ | CH₃ | C₂H₅ |
| 805 | phenyl | OCH₃ | CH₃ | C₂H₅ |
| 806 | 2-F-phenyl | OCH₃ | CH₃ | C₂H₅ |
| 807 | 3-F-phenyl | OCH₃ | CH₃ | C₂H₅ |
| 808 | 4-F-phenyl | OCH₃ | CH₃ | C₂H₅ |
| 809 | 2-Cl-phenyl | OCH₃ | CH₃ | C₂H₅ |
| 810 | 3-Cl-phenyl | OCH₃ | CH₃ | C₂H₅ |
| 811 | 4-Cl-phenyl | OCH₃ | CH₃ | C₂H₅ |
| 812 | 2-OH-phenyl | OCH₃ | CH₃ | C₂H₅ |
| 813 | 3-OH-phenyl | OCH₃ | CH₃ | C₂H₅ |
| 814 | 4-OH-phenyl | OCH₃ | CH₃ | C₂H₅ |
| 815 | 2-OCH₃-phenyl | OCH₃ | CH₃ | C₂H₅ |
| 816 | 3-OCH₃-phenyl | OCH₃ | CH₃ | C₂H₅ |
| 817 | 4-OCH₃-phenyl | OCH₃ | CH₃ | C₂H₅ |
| 818 | 2-OCF₃-phenyl | OCH₃ | CH₃ | C₂H₅ |
| 819 | 3-OCF₃-phenyl | OCH₃ | CH₃ | C₂H₅ |
| 820 | 4-OCF₃-phenyl | OCH₃ | CH₃ | C₂H₅ |
| 821 | 2-OCHF₂-phenyl | OCH₃ | CH₃ | C₂H₅ |
| 822 | 3-OCHF₂-phenyl | OCH₃ | CH₃ | C₂H₅ |
| 823 | 4-OCHF₂-phenyl | OCH₃ | CH₃ | C₂H₅ |
| 824 | 2-CF₃-phenyl | OCH₃ | CH₃ | C₂H₅ |
| 825 | 3-CF₃-phenyl | OCH₃ | CH₃ | C₂H₅ |
| 826 | 4-CF₃-phenyl | OCH₃ | CH₃ | C₂H₅ |
| 827 | 2-CH₃-phenyl | OCH₃ | CH₃ | C₂H₅ |
| 828 | 3-CH₃-phenyl | OCH₃ | CH₃ | C₂H₅ |
| 829 | 4-CH₃-phenyl | OCH₃ | CH₃ | C₂H₅ |
| 830 | 2-NO₂-phenyl | OCH₃ | CH₃ | C₂H₅ |
| 831 | 3-NO₂-phenyl | OCH₃ | CH₃ | C₂H₅ |
| 832 | 4-NO₂-phenyl | OCH₃ | CH₃ | C₂H₅ |
| 833 | 2-pyridyl | OCH₃ | CH₃ | C₂H₅ |
| 834 | 3-pyridyl | OCH₃ | CH₃ | C₂H₅ |
| 835 | 4-pyridyl | OCH₃ | CH₃ | C₂H₅ |
| 836 | cyclohexylamino | OCH₃ | CH₃ | C₂H₅ |
| 837 | cyclopentylamino | OCH₃ | CH₃ | C₂H₅ |
| 838 | H | Cl | CH₃ | C₂H₅ |
| 839 | CH₃ | Cl | CH₃ | C₂H₅ |
| 840 | C₂H₅ | Cl | CH₃ | C₂H₅ |
| 841 | n-C₃H₇ | Cl | CH₃ | C₂H₅ |
| 842 | i-C₃H₇ | Cl | CH₃ | C₂H₅ |
| 843 | n-C₄H₉ | Cl | CH₃ | C₂H₅ |
| 844 | s-C₄H₉ | Cl | CH₃ | C₂H₅ |
| 845 | i-C₄H₉ | Cl | CH₃ | C₂H₅ |
| 846 | t-C₄H₉ | Cl | CH₃ | C₂H₅ |
| 847 | CH₂Cl | Cl | CH₃ | C₂H₅ |
| 848 | CHCl₂ | Cl | CH₃ | C₂H₅ |
| 849 | CCl₃ | Cl | CH₃ | C₂H₅ |
| 850 | CH₂F | Cl | CH₃ | C₂H₅ |
| 851 | CHF₂ | Cl | CH₃ | C₂H₅ |
| 852 | CF₃ | Cl | CH₃ | C₂H₅ |
| 853 | CH₂CF₃ | Cl | CH₃ | C₂H₅ |
| 854 | CH₂OCH₃ | Cl | CH₃ | C₂H₅ |
| 855 | CH₂OCH₂CH₃ | Cl | CH₃ | C₂H₅ |
| 856 | CH₂NH₂ | Cl | CH₃ | C₂H₅ |
| 857 | (CH₂)₂COCH₃ | Cl | CH₃ | C₂H₅ |
| 858 | phenyl | Cl | CH₃ | C₂H₅ |
| 859 | 2-F-phenyl | Cl | CH₃ | C₂H₅ |
| 860 | 3-F-phenyl | Cl | CH₃ | C₂H₅ |
| 861 | 4-F-phenyl | Cl | CH₃ | C₂H₅ |
| 862 | 2-Cl-phenyl | Cl | CH₃ | C₂H₅ |
| 863 | 3-Cl-phenyl | Cl | CH₃ | C₂H₅ |
| 864 | 4-Cl-phenyl | Cl | CH₃ | C₂H₅ |
| 865 | 2-OH-phenyl | Cl | CH₃ | C₂H₅ |
| 866 | 3-OH-phenyl | Cl | CH₃ | C₂H₅ |
| 867 | 4-OH-phenyl | Cl | CH₃ | C₂H₅ |
| 868 | 2-OCH₃-phenyl | Cl | CH₃ | C₂H₅ |
| 869 | 3-OCH₃-phenyl | Cl | CH₃ | C₂H₅ |
| 870 | 4-OCH₃-phenyl | Cl | CH₃ | C₂H₅ |

TABLE B-continued

| | R³ | R¹ | R² | R⁴ |
|---|---|---|---|---|
| 871 | 2-OCF₃-phenyl | Cl | CH₃ | C₂H₅ |
| 872 | 3-OCF₃-phenyl | Cl | CH₃ | C₂H₅ |
| 873 | 4-OCF₃-phenyl | Cl | CH₃ | C₂H₅ |
| 874 | 2-OCHF₂-phenyl | Cl | CH₃ | C₂H₅ |
| 875 | 3-OCHF₂-phenyl | Cl | CH₃ | C₂H₅ |
| 876 | 4-OCHF₂-phenyl | Cl | CH₃ | C₂H₅ |
| 877 | 2-CF₃-phenyl | Cl | CH₃ | C₂H₅ |
| 878 | 3-CF₃-phenyl | Cl | CH₃ | C₂H₅ |
| 879 | 4-CF₃-phenyl | Cl | CH₃ | C₂H₅ |
| 880 | 2-CH₃-phenyl | Cl | CH₃ | C₂H₅ |
| 881 | 3-CH₃-phenyl | Cl | CH₃ | C₂H₅ |
| 882 | 4-CH₃-phenyl | Cl | CH₃ | C₂H₅ |
| 883 | 2-NO₂-phenyl | Cl | CH₃ | C₂H₅ |
| 884 | 3-NO₂-phenyl | Cl | CH₃ | C₂H₅ |
| 885 | 4-NO₂-phenyl | Cl | CH₃ | C₂H₅ |
| 886 | 2-pyridyl | Cl | CH₃ | C₂H₅ |
| 887 | 3-pyridyl | Cl | CH₃ | C₂H₅ |
| 888 | 4-pyridyl | Cl | CH₃ | C₂H₅ |
| 889 | cyclohexylamino | Cl | CH₃ | C₂H₅ |
| 890 | cyclopentylamino | Cl | CH₃ | C₂H₅ |
| 891 | CH₃ | CH₃ | H | C₂H₅ |
| 892 | C₂H₅ | CH₃ | H | C₂H₅ |
| 893 | n-C₃H₇ | CH₃ | H | C₂H₅ |
| 894 | i-C₃H₇ | CH₃ | H | C₂H₅ |
| 895 | n-C₄H₉ | CH₃ | H | C₂H₅ |
| 896 | s-C₄H₉ | CH₃ | H | C₂H₅ |
| 897 | i-C₄H₉ | CH₃ | H | C₂H₅ |
| 898 | t-C₄H₉ | CH₃ | H | C₂H₅ |
| 899 | CH₂Cl | CH₃ | H | C₂H₅ |
| 900 | CHCl₂ | CH₃ | H | C₂H₅ |
| 901 | CCl₃ | CH₃ | H | C₂H₅ |
| 902 | CH₂F | CH₃ | H | C₂H₅ |
| 903 | CHF₂ | CH₃ | H | C₂H₅ |
| 904 | CF₃ | CH₃ | H | C₂H₅ |
| 905 | CH₂CF₃ | CH₃ | H | C₂H₅ |
| 906 | CH₂OCH₃ | CH₃ | H | C₂H₅ |
| 907 | CH₂OCH₂CH₃ | CH₃ | H | C₂H₅ |
| 908 | CH₂NH₂ | CH₃ | H | C₂H₅ |
| 909 | (CH₂)₂COCH₃ | CH₃ | H | C₂H₅ |
| 910 | phenyl | CH₃ | H | C₂H₅ |
| 911 | 2-F-phenyl | CH₃ | H | C₂H₅ |
| 912 | 3-F-phenyl | CH₃ | H | C₂H₅ |
| 913 | 4-F-phenyl | CH₃ | H | C₂H₅ |
| 914 | 2-Cl-phenyl | CH₃ | H | C₂H₅ |
| 915 | 3-Cl-phenyl | CH₃ | H | C₂H₅ |
| 916 | 4-Cl-phenyl | CH₃ | H | C₂H₅ |
| 917 | 2-OH-phenyl | CH₃ | H | C₂H₅ |
| 918 | 3-OH-phenyl | CH₃ | H | C₂H₅ |
| 919 | 4-OH-phenyl | CH₃ | H | C₂H₅ |
| 920 | 2-OCH₃-phenyl | CH₃ | H | C₂H₅ |
| 921 | 3-OCH₃-phenyl | CH₃ | H | C₂H₅ |
| 922 | 4-OCH₃-phenyl | CH₃ | H | C₂H₅ |
| 923 | 2-OCF₃-phenyl | CH₃ | H | C₂H₅ |
| 924 | 3-OCF₃-phenyl | CH₃ | H | C₂H₅ |
| 925 | 4-OCF₃-phenyl | CH₃ | H | C₂H₅ |
| 926 | 2-OCHF₂-phenyl | CH₃ | H | C₂H₅ |
| 927 | 3-OCHF₂-phenyl | CH₃ | H | C₂H₅ |
| 928 | 4-OCHF₂-phenyl | CH₃ | H | C₂H₅ |
| 929 | 2-CF₃-phenyl | CH₃ | H | C₂H₅ |
| 930 | 3-CF₃-phenyl | CH₃ | H | C₂H₅ |
| 931 | 4-CF₃-phenyl | CH₃ | H | C₂H₅ |
| 932 | 2-CH₃-phenyl | CH₃ | H | C₂H₅ |
| 933 | 3-CH₃-phenyl | CH₃ | H | C₂H₅ |
| 934 | 4-CH₃-phenyl | CH₃ | H | C₂H₅ |
| 935 | 2-NO₂-phenyl | CH₃ | H | C₂H₅ |
| 936 | 3-NO₂-phenyl | CH₃ | H | C₂H₅ |
| 937 | 4-NO₂-phenyl | CH₃ | H | C₂H₅ |
| 938 | 2-pyridyl | CH₃ | H | C₂H₅ |
| 939 | 3-pyridyl | CH₃ | H | C₂H₅ |
| 940 | 4-pyridyl | CH₃ | H | C₂H₅ |
| 941 | cyclohexylamino | CH₃ | H | C₂H₅ |
| 942 | cyclopentylamino | CH₃ | H | C₂H₅ |
| 943 | H | OCH₃ | H | C₂H₅ |
| 944 | CH₃ | OCH₃ | H | C₂H₅ |
| 945 | C₂H₅ | OCH₃ | H | C₂H₅ |
| 946 | n-C₃H₇ | OCH₃ | H | C₂H₅ |
| 947 | i-C₃H₇ | OCH₃ | H | C₂H₅ |
| 948 | n-C₄H₉ | OCH₃ | H | C₂H₅ |
| 949 | s-C₄H₉ | OCH₃ | H | C₂H₅ |
| 950 | i-C₄H₉ | OCH₃ | H | C₂H₅ |
| 951 | t-C₄H₉ | OCH₃ | H | C₂H₅ |
| 952 | CH₂Cl | OCH₃ | H | C₂H₅ |
| 953 | CHCl₂ | OCH₃ | H | C₂H₅ |
| 954 | CCl₃ | OCH₃ | H | C₂H₅ |
| 955 | CH₂F | OCH₃ | H | C₂H₅ |
| 956 | CHF₂ | OCH₃ | H | C₂H₅ |
| 957 | CF₃ | OCH₃ | H | C₂H₅ |
| 958 | CH₂CF₃ | OCH₃ | H | C₂H₅ |
| 959 | CH₂OCH₃ | OCH₃ | H | C₂H₅ |
| 960 | CH₂OCH₂CH₃ | OCH₃ | H | C₂H₅ |
| 961 | CH₂NH₂ | OCH₃ | H | C₂H₅ |
| 962 | (CH₂)₂COCH₃ | OCH₃ | H | C₂H₅ |
| 963 | phenyl | OCH₃ | H | C₂H₅ |
| 964 | 2-F-phenyl | OCH₃ | H | C₂H₅ |
| 965 | 3-F-phenyl | OCH₃ | H | C₂H₅ |
| 966 | 4-F-phenyl | OCH₃ | H | C₂H₅ |
| 967 | 2-Cl-phenyl | OCH₃ | H | C₂H₅ |
| 968 | 3-Cl-phenyl | OCH₃ | H | C₂H₅ |
| 969 | 4-Cl-phenyl | OCH₃ | H | C₂H₅ |
| 970 | 2-OH-phenyl | OCH₃ | H | C₂H₅ |
| 971 | 3-OH-phenyl | OCH₃ | H | C₂H₅ |
| 972 | 4-OH-phenyl | OCH₃ | H | C₂H₅ |
| 973 | 2-OCH₃-phenyl | OCH₃ | H | C₂H₅ |
| 974 | 3-OCH₃-phenyl | OCH₃ | H | C₂H₅ |
| 975 | 4-OCH₃-phenyl | OCH₃ | H | C₂H₅ |
| 976 | 2-OCF₃-phenyl | OCH₃ | H | C₂H₅ |
| 977 | 3-OCF₃-phenyl | OCH₃ | H | C₂H₅ |
| 978 | 4-OCF₃-phenyl | OCH₃ | H | C₂H₅ |
| 979 | 2-OCHF₂-phenyl | OCH₃ | H | C₂H₅ |
| 980 | 3-OCHF₂-phenyl | OCH₃ | H | C₂H₅ |
| 981 | 4-OCHF₂-phenyl | OCH₃ | H | C₂H₅ |
| 982 | 2-CF₃-phenyl | OCH₃ | H | C₂H₅ |
| 983 | 3-CF₃-phenyl | OCH₃ | H | C₂H₅ |
| 984 | 4-CF₃-phenyl | OCH₃ | H | C₂H₅ |
| 985 | 2-CH₃-phenyl | OCH₃ | H | C₂H₅ |
| 986 | 3-CH₃-phenyl | OCH₃ | H | C₂H₅ |
| 987 | 4-CH₃-phenyl | OCH₃ | H | C₂H₅ |
| 988 | 2-NO₂-phenyl | OCH₃ | H | C₂H₅ |
| 989 | 3-NO₂-phenyl | OCH₃ | H | C₂H₅ |
| 990 | 4-NO₂-phenyl | OCH₃ | H | C₂H₅ |
| 991 | 2-pyridyl | OCH₃ | H | C₂H₅ |
| 992 | 3-pyridyl | OCH₃ | H | C₂H₅ |
| 993 | 4-pyridyl | OCH₃ | H | C₂H₅ |
| 994 | cyclohexylamino | OCH₃ | H | C₂H₅ |
| 995 | cyclopentylamino | OCH₃ | H | C₂H₅ |
| 996 | H | Cl | H | C₂H₅ |
| 997 | CH₃ | Cl | H | C₂H₅ |
| 998 | C₂H₅ | Cl | H | C₂H₅ |
| 999 | n-C₃H₇ | Cl | H | C₂H₅ |
| 999 | i-C₃H₇ | Cl | H | C₂H₅ |
| 1000 | n-C₄H₉ | Cl | H | C₂H₅ |
| 1001 | s-C₄H₉ | Cl | H | C₂H₅ |
| 1002 | i-C₄H₉ | Cl | H | C₂H₅ |
| 1003 | t-C₄H₉ | Cl | H | C₂H₅ |
| 1004 | CH₂Cl | Cl | H | C₂H₅ |
| 1005 | CHCl₂ | Cl | H | C₂H₅ |
| 1006 | CCl₃ | Cl | H | C₂H₅ |
| 1007 | CH₂F | Cl | H | C₂H₅ |
| 1008 | CHF₂ | Cl | H | C₂H₅ |
| 1009 | CF₃ | Cl | H | C₂H₅ |
| 1010 | CH₂CF₃ | Cl | H | C₂H₅ |
| 1011 | CH₂OCH₃ | Cl | H | C₂H₅ |
| 1012 | CH₂OCH₂CH₃ | Cl | H | C₂H₅ |
| 1013 | CH₂NH₂ | Cl | H | C₂H₅ |
| 1014 | (CH₂)₂COCH₃ | Cl | H | C₂H₅ |
| 1015 | phenyl | Cl | H | C₂H₅ |
| 1016 | 2-F-phenyl | Cl | H | C₂H₅ |
| 1017 | 3-F-phenyl | Cl | H | C₂H₅ |
| 1018 | 4-F-phenyl | Cl | H | C₂H₅ |
| 1019 | 2-Cl-phenyl | Cl | H | C₂H₅ |
| 1020 | 3-Cl-phenyl | Cl | H | C₂H₅ |
| 1021 | 4-Cl-phenyl | Cl | H | C₂H₅ |
| 1022 | 2-OH-phenyl | Cl | H | C₂H₅ |
| 1023 | 3-OH-phenyl | Cl | H | C₂H₅ |

TABLE B-continued

| | R³ | R¹ | R² | R⁴ |
|---|---|---|---|---|
| 1024 | 4-OH-phenyl | Cl | H | $C_2H_5$ |
| 1025 | 2-OCH₃-phenyl | Cl | H | $C_2H_5$ |
| 1026 | 3-OCH₃-phenyl | Cl | H | $C_2H_5$ |
| 1027 | 4-OCH₃-phenyl | Cl | H | $C_2H_5$ |
| 1028 | 2-OCF₃-phenyl | Cl | H | $C_2H_5$ |
| 1029 | 3-OCF₃-phenyl | Cl | H | $C_2H_5$ |
| 1030 | 4-OCF₃-phenyl | Cl | H | $C_2H_5$ |
| 1031 | 2-OCHF₂-phenyl | Cl | H | $C_2H_5$ |
| 1032 | 3-OCHF₂-phenyl | Cl | H | $C_2H_5$ |
| 1033 | 4-OCHF₂-phenyl | Cl | H | $C_2H_5$ |
| 1034 | 2-CF₃-phenyl | Cl | H | $C_2H_5$ |
| 1035 | 3-CF₃-phenyl | Cl | H | $C_2H_5$ |
| 1036 | 4-CF₃-phenyl | Cl | H | $C_2H_5$ |
| 1037 | 2-CH₃-phenyl | Cl | H | $C_2H_5$ |
| 1038 | 3-CH₃-phenyl | Cl | H | $C_2H_5$ |
| 1039 | 4-CH₃-phenyl | Cl | H | $C_2H_5$ |
| 1040 | 2-NO₂-phenyl | Cl | H | $C_2H_5$ |
| 1041 | 3-NO₂-phenyl | Cl | H | $C_2H_5$ |
| 1042 | 4-NO₂-phenyl | Cl | H | $C_2H_5$ |
| 1043 | 2-pyridyl | Cl | H | $C_2H_5$ |
| 1044 | 3-pyridyl | Cl | H | $C_2H_5$ |
| 1045 | 4-pyridyl | Cl | H | $C_2H_5$ |
| 1046 | cyclohexylamino | Cl | H | $C_2H_5$ |
| 1047 | cyclopentylamino | Cl | H | $C_2H_5$ |
| 1046 | CH₃ | CH₃ | CH₃ | $i-C_3H_7$ |
| 1049 | $C_2H_5$ | CH₃ | CH₃ | $i-C_3H_7$ |
| 1050 | $n-C_3H_7$ | CH₃ | CH₃ | $i-C_3H_7$ |
| 1051 | $i-C_3H_7$ | CH₃ | CH₃ | $i-C_3H_7$ |
| 1052 | $n-C_4H_9$ | CH₃ | CH₃ | $i-C_3H_7$ |
| 1053 | $s-C_4H_9$ | CH₃ | CH₃ | $i-C_3H_7$ |
| 1054 | $i-C_4H_9$ | CH₃ | CH₃ | $i-C_3H_7$ |
| 1055 | $t-C_4H_9$ | CH₃ | CH₃ | $i-C_3H_7$ |
| 1056 | CH₂Cl | CH₃ | CH₃ | $i-C_3H_7$ |
| 1057 | CHCl₂ | CH₃ | CH₃ | $i-C_3H_7$ |
| 1058 | CCl₃ | CH₃ | CH₃ | $i-C_3H_7$ |
| 1059 | CH₂F | CH₃ | CH₃ | $i-C_3H_7$ |
| 1060 | CHF₂ | CH₃ | CH₃ | $i-C_3H_7$ |
| 1061 | CF₃ | CH₃ | CH₃ | $i-C_3H_7$ |
| 1062 | CH₂CF₃ | CH₃ | CH₃ | $i-C_3H_7$ |
| 1063 | CH₂OCH₃ | CH₃ | CH₃ | $i-C_3H_7$ |
| 1064 | CH₂OCH₂CH₃ | CH₃ | CH₃ | $i-C_3H_7$ |
| 1065 | CH₂NH₂ | CH₃ | CH₃ | $i-C_3H_7$ |
| 1066 | (CH₂)₂COCH₃ | CH₃ | CH₃ | $i-C_3H_7$ |
| 1067 | phenyl | CH₃ | CH₃ | $i-C_3H_7$ |
| 1068 | 2-F-phenyl | CH₃ | CH₃ | $i-C_3H_7$ |
| 1069 | 3-F-phenyl | CH₃ | CH₃ | $i-C_3H_7$ |
| 1070 | 4-F-phenyl | CH₃ | CH₃ | $i-C_3H_7$ |
| 1071 | 2-Cl-phenyl | CH₃ | CH₃ | $i-C_3H_7$ |
| 1072 | 3-Cl-phenyl | CH₃ | CH₃ | $i-C_3H_7$ |
| 1073 | 4-Cl-phenyl | CH₃ | CH₃ | $i-C_3H_7$ |
| 1074 | 2-OH-phenyl | CH₃ | CH₃ | $i-C_3H_7$ |
| 1075 | 3-OH-phenyl | CH₃ | CH₃ | $i-C_3H_7$ |
| 1076 | 4-OH-phenyl | CH₃ | CH₃ | $i-C_3H_7$ |
| 1077 | 2-OCH₃-phenyl | CH₃ | CH₃ | $i-C_3H_7$ |
| 1078 | 3-OCH₃-phenyl | CH₃ | CH₃ | $i-C_3H_7$ |
| 1079 | 4-OCH₃-phenyl | CH₃ | CH₃ | $i-C_3H_7$ |
| 1080 | 2-OCF₃-phenyl | CH₃ | CH₃ | $i-C_3H_7$ |
| 1081 | 3-OCF₃-phenyl | CH₃ | CH₃ | $i-C_3H_7$ |
| 1082 | 4-OCF₃-phenyl | CH₃ | CH₃ | $i-C_3H_7$ |
| 1083 | 2-OCHF₂-phenyl | CH₃ | CH₃ | $i-C_3H_7$ |
| 1084 | 3-OCHF₂-phenyl | CH₃ | CH₃ | $i-C_3H_7$ |
| 1085 | 4-OCHF₂-phenyl | CH₃ | CH₃ | $i-C_3H_7$ |
| 1086 | 2-CF₃-phenyl | CH₃ | CH₃ | $i-C_3H_7$ |
| 1087 | 3-CF₃-phenyl | CH₃ | CH₃ | $i-C_3H_7$ |
| 1088 | 4-CF₃-phenyl | CH₃ | CH₃ | $i-C_3H_7$ |
| 1089 | 2-CH₃-phenyl | CH₃ | CH₃ | $i-C_3H_7$ |
| 1090 | 3-CH₃-phenyl | CH₃ | CH₃ | $i-C_3H_7$ |
| 1091 | 4-CH₃-phenyl | CH₃ | CH₃ | $i-C_3H_7$ |
| 1092 | 2-NO₂-phenyl | CH₃ | CH₃ | $i-C_3H_7$ |
| 1093 | 3-NO₂-phenyl | CH₃ | CH₃ | $i-C_3H_7$ |
| 1094 | 4-NO₂-phenyl | CH₃ | CH₃ | $i-C_3H_7$ |
| 1095 | 2-pyridyl | CH₃ | CH₃ | $i-C_3H_7$ |
| 1096 | 3-pyridyl | CH₃ | CH₃ | $i-C_3H_7$ |
| 1097 | 4-pyridyl | CH₃ | CH₃ | $i-C_3H_7$ |
| 1098 | cyclohexylamino | CH₃ | CH₃ | $i-C_3H_7$ |
| 1099 | cyclopentylamino | CH₃ | CH₃ | $i-C_3H_7$ |
| 1100 | H | OCH₃ | CH₃ | $i-C_3H_7$ |
| 1101 | CH₃ | OCH₃ | CH₃ | $i-C_3H_7$ |
| 1102 | $C_2H_5$ | OCH₃ | CH₃ | $i-C_3H_7$ |
| 1103 | $n-C_3H_7$ | OCH₃ | CH₃ | $i-C_3H_7$ |
| 1104 | $i-C_3H_7$ | OCH₃ | CH₃ | $i-C_3H_7$ |
| 1105 | $n-C_4H_9$ | OCH₃ | CH₃ | $i-C_3H_7$ |
| 1106 | $s-C_4H_9$ | OCH₃ | CH₃ | $i-C_3H_7$ |
| 1107 | $i-C_4H_9$ | OCH₃ | CH₃ | $i-C_3H_7$ |
| 1108 | $t-C_4H_9$ | OCH₃ | CH₃ | $i-C_3H_7$ |
| 1109 | CH₂Cl | OCH₃ | CH₃ | $i-C_3H_7$ |
| 1110 | CHCl₂ | OCH₃ | CH₃ | $i-C_3H_7$ |
| 1111 | CCl₃ | OCH₃ | CH₃ | $i-C_3H_7$ |
| 1112 | CH₂F | OCH₃ | CH₃ | $i-C_3H_7$ |
| 1113 | CHF₂ | OCH₃ | CH₃ | $i-C_3H_7$ |
| 1114 | CF₃ | OCH₃ | CH₃ | $i-C_3H_7$ |
| 1115 | CH₂CF₃ | OCH₃ | CH₃ | $i-C_3H_7$ |
| 1116 | CH₂OCH₃ | OCH₃ | CH₃ | $i-C_3H_7$ |
| 1117 | CH₂OCH₂CH₃ | OCH₃ | CH₃ | $i-C_3H_7$ |
| 1118 | CH₂NH₂ | OCH₃ | CH₃ | $i-C_3H_7$ |
| 1119 | (CH₂)₂COCH₃ | OCH₃ | CH₃ | $i-C_3H_7$ |
| 1120 | phenyl | OCH₃ | CH₃ | $i-C_3H_7$ |
| 1121 | 2-F-phenyl | OCH₃ | CH₃ | $i-C_3H_7$ |
| 1122 | 3-F-phenyl | OCH₃ | CH₃ | $i-C_3H_7$ |
| 1123 | 4-F-phenyl | OCH₃ | CH₃ | $i-C_3H_7$ |
| 1124 | 2-Cl-phenyl | OCH₃ | CH₃ | $i-C_3H_7$ |
| 1125 | 3-Cl-phenyl | OCH₃ | CH₃ | $i-C_3H_7$ |
| 1126 | 4-Cl-phenyl | OCH₃ | CH₃ | $i-C_3H_7$ |
| 1127 | 2-OH-phenyl | OCH₃ | CH₃ | $i-C_3H_7$ |
| 1128 | 3-OH-phenyl | OCH₃ | CH₃ | $i-C_3H_7$ |
| 1129 | 4-OH-phenyl | OCH₃ | CH₃ | $i-C_3H_7$ |
| 1130 | 2-OCH₃-phenyl | OCH₃ | CH₃ | $i-C_3H_7$ |
| 1131 | 3-OCH₃-phenyl | OCH₃ | CH₃ | $i-C_3H_7$ |
| 1132 | 4-OCH₃-phenyl | OCH₃ | CH₃ | $i-C_3H_7$ |
| 1133 | 2-OCF₃-phenyl | OCH₃ | CH₃ | $i-C_3H_7$ |
| 1134 | 3-OCF₃-phenyl | OCH₃ | CH₃ | $i-C_3H_7$ |
| 1135 | 4-OCF₃-phenyl | OCH₃ | CH₃ | $i-C_3H_7$ |
| 1136 | 2-OCHF₂-phenyl | OCH₃ | CH₃ | $i-C_3H_7$ |
| 1137 | 3-OCHF₂-phenyl | OCH₃ | CH₃ | $i-C_3H_7$ |
| 1138 | 4-OCHF₂-phenyl | OCH₃ | CH₃ | $i-C_3H_7$ |
| 1139 | 2-CF₃-phenyl | OCH₃ | CH₃ | $i-C_3H_7$ |
| 1140 | 3-CF₃-phenyl | OCH₃ | CH₃ | $i-C_3H_7$ |
| 1141 | 4-CF₃-phenyl | OCH₃ | CH₃ | $i-C_3H_7$ |
| 1142 | 2-CH₃-phenyl | OCH₃ | CH₃ | $i-C_3H_7$ |
| 1143 | 3-CH₃-phenyl | OCH₃ | CH₃ | $i-C_3H_7$ |
| 1144 | 4-CH₃-phenyl | OCH₃ | CH₃ | $i-C_3H_7$ |
| 1145 | 2-NO₂-phenyl | OCH₃ | CH₃ | $i-C_3H_7$ |
| 1146 | 3-NO₂-phenyl | OCH₃ | CH₃ | $i-C_3H_7$ |
| 1147 | 4-NO₂-phenyl | OCH₃ | CH₃ | $i-C_3H_7$ |
| 1148 | 2-pyridyl | OCH₃ | CH₃ | $i-C_3H_7$ |
| 1149 | 3-pyridyl | OCH₃ | CH₃ | $i-C_3H_7$ |
| 1150 | 4-pyridyl | OCH₃ | CH₃ | $i-C_3H_7$ |
| 1151 | cyclohexylamino | OCH₃ | CH₃ | $i-C_3H_7$ |
| 1152 | cyclopentylamino | OCH₃ | CH₃ | $i-C_3H_7$ |
| 1153 | H | Cl | CH₃ | $i-C_3H_7$ |
| 1154 | CH₃ | Cl | CH₃ | $i-C_3H_7$ |
| 1155 | $C_2H_5$ | Cl | CH₃ | $i-C_3H_7$ |
| 1156 | $n-C_3H_7$ | Cl | CH₃ | $i-C_3H_7$ |
| 1157 | $i-C_3H_7$ | Cl | CH₃ | $i-C_3H_7$ |
| 1158 | $n-C_4H_9$ | Cl | CH₃ | $i-C_3H_7$ |
| 1159 | $s-C_4H_9$ | Cl | CH₃ | $i-C_3H_7$ |
| 1160 | $i-C_4H_9$ | Cl | CH₃ | $i-C_3H_7$ |
| 1161 | $t-C_4H_9$ | Cl | CH₃ | $i-C_3H_7$ |
| 1162 | CH₂Cl | Cl | CH₃ | $i-C_3H_7$ |
| 1163 | CHCl₂ | Cl | CH₃ | $i-C_3H_7$ |
| 1164 | CCl₃ | Cl | CH₃ | $i-C_3H_7$ |
| 1165 | CH₂F | Cl | CH₃ | $i-C_3H_7$ |
| 1166 | CHF₂ | Cl | CH₃ | $i-C_3H_7$ |
| 1167 | CF₃ | Cl | CH₃ | $i-C_3H_7$ |
| 1168 | CH₂CF₃ | Cl | CH₃ | $i-C_3H_7$ |
| 1169 | CH₂OCH₃ | Cl | CH₃ | $i-C_3H_7$ |
| 1170 | CH₂OCH₂CH₃ | Cl | CH₃ | $i-C_3H_7$ |
| 1171 | CH₂NH₂ | Cl | CH₃ | $i-C_3H_7$ |
| 1172 | (CH₂)₂COCH₃ | Cl | CH₃ | $i-C_3H_7$ |
| 1173 | phenyl | Cl | CH₃ | $i-C_3H_7$ |
| 1174 | 2-F-phenyl | Cl | CH₃ | $i-C_3H_7$ |
| 1175 | 3-F-phenyl | Cl | CH₃ | $i-C_3H_7$ |
| 1176 | 4-F-phenyl | Cl | CH₃ | $i-C_3H_7$ |
| 1177 | 2-Cl-phenyl | Cl | CH₃ | $i-C_3H_7$ |

TABLE B-continued

| | R³ | R¹ | R² | R⁴ |
|---|---|---|---|---|
| 1178 | 3-Cl-phenyl | Cl | CH₃ | i-C₃H₇ |
| 1179 | 4-Cl-phenyl | Cl | CH₃ | i-C₃H₇ |
| 1180 | 2-OH-phenyl | Cl | CH₃ | i-C₃H₇ |
| 1181 | 3-OH-phenyl | Cl | CH₃ | i-C₃H₇ |
| 1182 | 4-OH-phenyl | Cl | CH₃ | i-C₃H₇ |
| 1183 | 2-OCH₃-phenyl | Cl | CH₃ | i-C₃H₇ |
| 1184 | 3-OCH₃-phenyl | Cl | CH₃ | i-C₃H₇ |
| 1185 | 4-OCH₃-phenyl | Cl | CH₃ | i-C₃H₇ |
| 1186 | 2-OCF₃-phenyl | Cl | CH₃ | i-C₃H₇ |
| 1187 | 3-OCF₃-phenyl | Cl | CH₃ | i-C₃H₇ |
| 1188 | 4-OCF₃-phenyl | Cl | CH₃ | i-C₃H₇ |
| 1189 | 2-OCHF₂-phenyl | Cl | CH₃ | i-C₃H₇ |
| 1190 | 3-OCHF₂-phenyl | Cl | CH₃ | i-C₃H₇ |
| 1191 | 4-OCHF₂-phenyl | Cl | CH₃ | i-C₃H₇ |
| 1192 | 2-CF₃-phenyl | Cl | CH₃ | i-C₃H₇ |
| 1193 | 3-CF₃-phenyl | Cl | CH₃ | i-C₃H₇ |
| 1194 | 4-CF₃-phenyl | Cl | CH₃ | i-C₃H₇ |
| 1195 | 2-CH₃-phenyl | Cl | CH₃ | i-C₃H₇ |
| 1196 | 3-CH₃-phenyl | Cl | CH₃ | i-C₃H₇ |
| 1197 | 4-CH₃-phenyl | Cl | CH₃ | i-C₃H₇ |
| 1198 | 2-NO₂-phenyl | Cl | CH₃ | i-C₃H₇ |
| 1199 | 3-NO₂-phenyl | Cl | CH₃ | i-C₃H₇ |
| 1200 | 4-NO₂-phenyl | Cl | CH₃ | i-C₃H₇ |
| 1201 | 2-pyridyl | Cl | CH₃ | i-C₃H₇ |
| 1202 | 3-pyridyl | Cl | CH₃ | i-C₃H₇ |
| 1203 | 4-pyridyl | Cl | CH₃ | i-C₃H₇ |
| 1204 | cyclohexylamino | Cl | CH₃ | i-C₃H₇ |
| 1205 | cyclopentylamino | Cl | CH₃ | i-C₃H₇ |
| 1206 | CH₃ | CH₃ | H | i-C₃H₇ |
| 1207 | C₂H₅ | CH₃ | H | i-C₃H₇ |
| 1208 | n-C₃H₇ | CH₃ | H | i-C₃H₇ |
| 1209 | i-C₃H₇ | CH₃ | H | i-C₃H₇ |
| 1210 | n-C₄H₉ | CH₃ | H | i-C₃H₇ |
| 1211 | s-C₄H₉ | CH₃ | H | i-C₃H₇ |
| 1212 | i-C₄H₉ | CH₃ | H | i-C₃H₇ |
| 1213 | t-C₄H₉ | CH₃ | H | i-C₃H₇ |
| 1214 | CH₂Cl | CH₃ | H | i-C₃H₇ |
| 1215 | CHCl₂ | CH₃ | H | i-C₃H₇ |
| 1116 | CCl₃ | CH₃ | H | i-C₃H₇ |
| 1217 | CH₂F | CH₃ | H | i-C₃H₇ |
| 1218 | CHF₂ | CH₃ | H | i-C₃H₇ |
| 1219 | CF₃ | CH₃ | H | i-C₃H₇ |
| 1220 | CH₂CF₃ | CH₃ | H | i-C₃H₇ |
| 1221 | CH₂OCH₃ | CH₃ | H | i-C₃H₇ |
| 1222 | CH₂OCH₂CH₃ | CH₃ | H | i-C₃H₇ |
| 1223 | CH₂NH₂ | CH₃ | H | i-C₃H₇ |
| 1224 | (CH₂)₂COCH₃ | CH₃ | H | i-C₃H₇ |
| 1225 | phenyl | CH₃ | H | i-C₃H₇ |
| 1226 | 2-F-phenyl | CH₃ | H | i-C₃H₇ |
| 1227 | 3-F-phenyl | CH₃ | H | i-C₃H₇ |
| 1228 | 4-F-phenyl | CH₃ | H | i-C₃H₇ |
| 1229 | 2-Cl-phenyl | CH₃ | H | i-C₃H₇ |
| 1230 | 3-Cl-phenyl | CH₃ | H | i-C₃H₇ |
| 1231 | 4-Cl-phenyl | CH₃ | H | i-C₃H₇ |
| 1232 | 2-OH-phenyl | CH₃ | H | i-C₃H₇ |
| 1233 | 3-OH-phenyl | CH₃ | H | i-C₃H₇ |
| 1234 | 4-OH-phenyl | CH₃ | H | i-C₃H₇ |
| 1235 | 2-OCH₃-phenyl | CH₃ | H | i-C₃H₇ |
| 1236 | 3-OCH₃-phenyl | CH₃ | H | i-C₃H₇ |
| 1237 | 4-OCH₃-phenyl | CH₃ | H | i-C₃H₇ |
| 1238 | 2-OCF₃-phenyl | CH₃ | H | i-C₃H₇ |
| 1239 | 3-OCF₃-phenyl | CH₃ | H | i-C₃H₇ |
| 1240 | 4-OCF₃-phenyl | CH₃ | H | i-C₃H₇ |
| 1241 | 2-OCHF₂-phenyl | CH₃ | H | i-C₃H₇ |
| 1242 | 3-OCHF₂-phenyl | CH₃ | H | i-C₃H₇ |
| 1243 | 4-OCHF₂-phenyl | CH₃ | H | i-C₃H₇ |
| 1244 | 2-CF₃-phenyl | CH₃ | H | i-C₃H₇ |
| 1245 | 3-CF₃-phenyl | CH₃ | H | i-C₃H₇ |
| 1246 | 4-CF₃-phenyl | CH₃ | H | i-C₃H₇ |
| 1247 | 2-CH₃-phenyl | CH₃ | H | i-C₃H₇ |
| 1248 | 3-CH₃-phenyl | CH₃ | H | i-C₃H₇ |
| 1249 | 4-CH₃-phenyl | CH₃ | H | i-C₃H₇ |
| 1250 | 2-NO₂-phenyl | CH₃ | H | i-C₃H₇ |
| 1251 | 3-NO₂-phenyl | CH₃ | H | i-C₃H₇ |
| 1252 | 4-NO₂-phenyl | CH₃ | H | i-C₃H₇ |
| 1253 | 2-pyridyl | CH₃ | H | i-C₃H₇ |
| 1254 | 3-pyridyl | CH₃ | H | i-C₃H₇ |
| 1255 | 4-pyridyl | CH₃ | H | i-C₃H₇ |
| 1256 | cyclohexylamino | CH₃ | H | i-C₃H₇ |
| 1257 | cyclopentylamino | CH₃ | H | i-C₃H₇ |
| 1258 | H | OCH₃ | H | i-C₃H₇ |
| 1259 | CH₃ | OCH₃ | H | i-C₃H₇ |
| 1260 | C₂H₅ | OCH₃ | H | i-C₃H₇ |
| 1261 | n-C₃H₇ | OCH₃ | H | i-C₃H₇ |
| 1262 | i-C₃H₇ | OCH₃ | H | i-C₃H₇ |
| 1263 | n-C₄H₉ | OCH₃ | H | i-C₃H₇ |
| 1264 | s-C₄H₉ | OCH₃ | H | i-C₃H₇ |
| 1265 | i-C₄H₉ | OCH₃ | H | i-C₃H₇ |
| 1266 | t-C₄H₉ | OCH₃ | H | i-C₃H₇ |
| 1267 | CH₂Cl | OCH₃ | H | i-C₃H₇ |
| 1268 | CHCl₂ | OCH₃ | H | i-C₃H₇ |
| 1269 | CCl₃ | OCH₃ | H | i-C₃H₇ |
| 1270 | CH₂F | OCH₃ | H | i-C₃H₇ |
| 1271 | CHF₂ | OCH₃ | H | i-C₃H₇ |
| 1272 | CF₃ | OCH₃ | H | i-C₃H₇ |
| 1273 | CH₂CF₃ | OCH₃ | H | i-C₃H₇ |
| 1274 | CH₂OCH₃ | OCH₃ | H | i-C₃H₇ |
| 1275 | CH₂OCH₂CH₃ | OCH₃ | H | i-C₃H₇ |
| 1276 | CH₂NH₂ | OCH₃ | H | i-C₃H₇ |
| 1277 | (CH₂)₂COCH₃ | OCH₃ | H | i-C₃H₇ |
| 1278 | phenyl | OCH₃ | H | i-C₃H₇ |
| 1279 | 2-F-phenyl | OCH₃ | H | i-C₃H₇ |
| 1280 | 3-F-phenyl | OCH₃ | H | i-C₃H₇ |
| 1281 | 4-F-phenyl | OCH₃ | H | i-C₃H₇ |
| 1282 | 2-Cl-phenyl | OCH₃ | H | i-C₃H₇ |
| 1283 | 3-Cl-phenyl | OCH₃ | H | i-C₃H₇ |
| 1284 | 4-Cl-phenyl | OCH₃ | H | i-C₃H₇ |
| 1285 | 2-OH-phenyl | OCH₃ | H | i-C₃H₇ |
| 1286 | 3-OH-phenyl | OCH₃ | H | i-C₃H₇ |
| 1287 | 4-OH-phenyl | OCH₃ | H | i-C₃H₇ |
| 1288 | 2-OCH₃-phenyl | OCH₃ | H | i-C₃H₇ |
| 1289 | 3-OCH₃-phenyl | OCH₃ | H | i-C₃H₇ |
| 1290 | 4-OCH₃-phenyl | OCH₃ | H | i-C₃H₇ |
| 1291 | 2-OCF₃-phenyl | OCH₃ | H | i-C₃H₇ |
| 1292 | 3-OCF₃-phenyl | OCH₃ | H | i-C₃H₇ |
| 1293 | 4-OCF₃-phenyl | OCH₃ | H | i-C₃H₇ |
| 1294 | 2-OCHF₂-phenyl | OCH₃ | H | i-C₃H₇ |
| 1295 | 3-OCHF₂-phenyl | OCH₃ | H | i-C₃H₇ |
| 1296 | 4-OCHF₂-phenyl | OCH₃ | H | i-C₃H₇ |
| 1297 | 2-CF₃-phenyl | OCH₃ | H | i-C₃H₇ |
| 1298 | 3-CF₃-phenyl | OCH₃ | H | i-C₃H₇ |
| 1299 | 4-CF₃-phenyl | OCH₃ | H | i-C₃H₇ |
| 1300 | 2-CH₃-phenyl | OCH₃ | H | i-C₃H₇ |
| 1301 | 3-CH₃-phenyl | OCH₃ | H | i-C₃H₇ |
| 1302 | 4-CH₃-phenyl | OCH₃ | H | i-C₃H₇ |
| 1303 | 2-NO₂-phenyl | OCH₃ | H | i-C₃H₇ |
| 1304 | 3-NO₂-phenyl | OCH₃ | H | i-C₃H₇ |
| 1305 | 4-NO₂-phenyl | OCH₃ | H | i-C₃H₇ |
| 1306 | 2-pyridyl | OCH₃ | H | i-C₃H₇ |
| 1307 | 3-pyridyl | OCH₃ | H | i-C₃H₇ |
| 1308 | 4-pyridyl | OCH₃ | H | i-C₃H₇ |
| 1309 | cyclohexylamino | OCH₃ | H | i-C₃H₇ |
| 1310 | cyclopentylamino | OCH₃ | H | i-C₃H₇ |
| 1311 | H | Cl | H | i-C₃H₇ |
| 1312 | CH₃ | Cl | H | i-C₃H₇ |
| 1313 | C₂H₅ | Cl | H | i-C₃H₇ |
| 1314 | n-C₃H₇ | Cl | H | i-C₃H₇ |
| 1315 | i-C₃H₇ | Cl | H | i-C₃H₇ |
| 1316 | n-C₄H₉ | Cl | H | i-C₃H₇ |
| 1317 | s-C₄H₉ | Cl | H | i-C₃H₇ |
| 1318 | i-C₄H₉ | Cl | H | i-C₃H₇ |
| 1319 | t-C₄H₉ | Cl | H | i-C₃H₇ |
| 1320 | CH₂Cl | Cl | H | i-C₃H₇ |
| 1321 | CHCl₂ | Cl | H | i-C₃H₇ |
| 1322 | CCl₃ | Cl | H | i-C₃H₇ |
| 1323 | CH₂F | Cl | H | i-C₃H₇ |
| 1324 | CHF₂ | Cl | H | i-C₃H₇ |
| 1325 | CF₃ | Cl | H | i-C₃H₇ |
| 1326 | CH₂CF₃ | Cl | H | i-C₃H₇ |
| 1327 | CH₂OCH₃ | Cl | H | i-C₃H₇ |
| 1328 | CH₂OCH₂CH₃ | Cl | H | i-C₃H₇ |
| 1329 | CH₂NH₂ | Cl | H | i-C₃H₇ |
| 1330 | (CH₂)₂COCH₃ | Cl | H | i-C₃H₇ |
| 1331 | phenyl | Cl | H | i-C₃H₇ |

TABLE B-continued

| | R³ | R¹ | R² | R⁴ |
|---|---|---|---|---|
| 1332 | 2-F-phenyl | Cl | H | i-C₃H₇ |
| 1333 | 3-F-phenyl | Cl | H | i-C₃H₇ |
| 1334 | 4-F-phenyl | Cl | H | i-C₃H₇ |
| 1335 | 2-Cl-phenyl | Cl | H | i-C₃H₇ |
| 1336 | 3-Cl-phenyl | Cl | H | i-C₃H₇ |
| 1337 | 4-Cl-phenyl | Cl | H | i-C₃H₇ |
| 1338 | 2-OH-phenyl | Cl | H | i-C₃H₇ |
| 1339 | 3-OH-phenyl | Cl | H | i-C₃H₇ |
| 1340 | 4-OH-phenyl | Cl | H | i-C₃H₇ |
| 1341 | 2-OCH₃-phenyl | Cl | H | i-C₃H₇ |
| 1342 | 3-OCH₃-phenyl | Cl | H | i-C₃H₇ |
| 1343 | 4-OCH₃-phenyl | Cl | H | i-C₃H₇ |
| 1344 | 2-OCF₃-phenyl | Cl | H | i-C₃H₇ |
| 1345 | 3-OCF₃-phenyl | OCH₃ | H | i-C₃H₇ |
| 1346 | 4-OCF₃-phenyl | OCH₃ | H | i-C₃H₇ |
| 1347 | 2-OCHF₂-phenyl | OCH₃ | H | i-C₃H₇ |
| 1348 | 3-OCHF₂-phenyl | OCH₃ | H | i-C₃H₇ |
| 1349 | 4-OCHF₂-phenyl | OCH₃ | H | i-C₃H₇ |
| 1350 | 2-CF₃-phenyl | OCH₃ | H | i-C₃H₇ |
| 1351 | 3-CF₃-phenyl | OCH₃ | H | i-C₃H₇ |
| 1352 | 4-CF₃-phenyl | OCH₃ | H | i-C₃H₇ |
| 1353 | 2-CH₃-phenyl | OCH₃ | H | i-C₃H₇ |
| 1353 | 3-CH₃-phenyl | OCH₃ | H | i-C₃H₇ |
| 1354 | 4-CH₃-phenyl | OCH₃ | H | i-C₃H₇ |
| 1355 | H | CH₃ | H | H |
| 1356 | 3-NO₂-phenyl | OCH₃ | H | i-C₃H₇ |
| 1357 | H | CH₃ | CH₃ | CH₃ |
| 1358 | 2-pyridyl | OCH₃ | H | i-C₃H₇ |
| 1359 | H | CH₃ | CH₃ | C₂H₅ |
| 1360 | H | CH₃ | H | C₂H₅ |
| 1361 | H | CH₃ | CH₃ | i-C₃H₇ |
| 1362 | H | CH₃ | H | i-C₃H₇ |
| 1363 | H | CH₃ | H | CH₃ |

Examples of benzimidazol-5-ylcarbonyl derivatives of cyclohexenones (compounds I-3=compounds I where X=C—R³ and Y=N—R⁴) particularly preferred according to the invention are the compounds listed in Tables 51 to 75.

TABLE 51

Compounds I-3a.1 to I-3a.1363

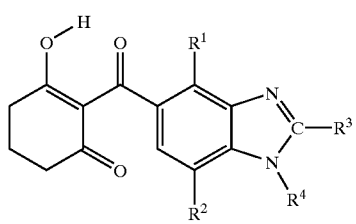

I-3a

Compounds of the formula I-3a, in which the substituents R¹, R², R³ and R⁴ for each individual compound correspond in each case to one row of Table B.

TABLE 52

Compounds I-3b.1 to I-3b.1363

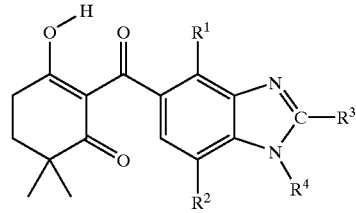

I-3b

Compounds of the formula I-3b, in which the substituents R¹, R², R³ and R⁴ for each individual compound correspond in each case to one row of Table B.

TABLE 53

Compounds I-3c.1 to I-3c.1363

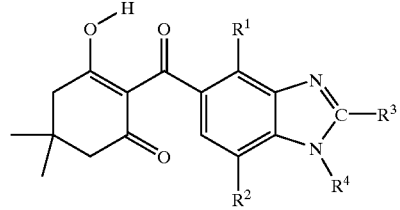

I-3c

Compounds of the formula I-3c, in which the substituents R¹, R², R³ and R⁴ for each individual compound correspond in each case to one row of Table B.

TABLE 54

Compounds I-3d.1 to I-3d.1363

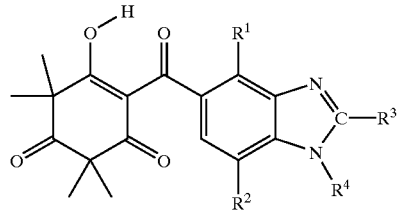

I-3d

Compounds of the formula I-3d, in which the substituents R¹, R², R³ and R⁴ for each individual compound correspond in each case to one row of Table B.

TABLE 55

Compounds I-3e.1 to I-3e.1363

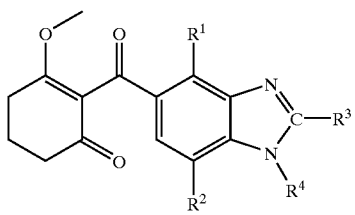

I-3e

Compounds of the formula I-3e, in which the substituents R¹, R², R³ and R⁴ for each individual compound correspond in each case to one row of Table B.

TABLE 56

Compounds I-3f.1 to I-3f.1363

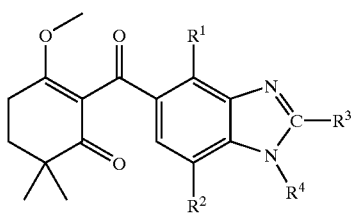

I-3f

Compounds of the formula I-3f, in which the substituents R¹, R², R³ and R⁴ for each individual compound correspond in each case to one row of Table B.

TABLE 57

Compounds I-3g.1 to I-3g.1363

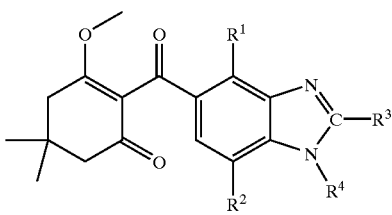

I-3g

Compounds of the formula I-3g, in which the substituents R¹, R², R³ and R⁴ for each individual compound correspond in each case to one row of Table B.

TABLE 58

Compounds I-3h.1 to I-3h.1363

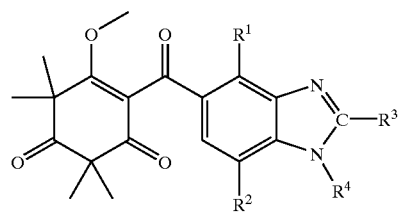

I-3h

Compounds of the formula I-3h, in which the substituents R¹, R², R³ and R⁴ for each individual compound correspond in each case to one row of Table B.

TABLE 59

Compounds I-3i.1 to I-3i.1363

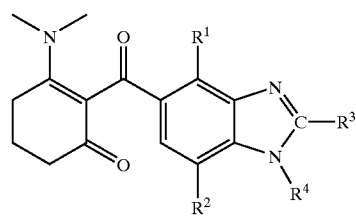

I-3i

Compounds of the formula I-3i, in which the substituents R¹, R², R³ and R⁴ for each individual compound correspond in each case to one row of Table B.

TABLE 60

Compounds I-3k.1 to I-3k.1363

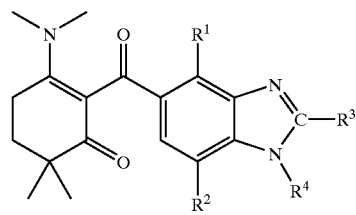

I-3k

Compounds of the formula I-3k, in which the substituents R¹, R², R³ and R⁴ for each individual compound correspond in each case to one row of Table B.

TABLE 61

Compounds I-3l.1 to I-3l.1363

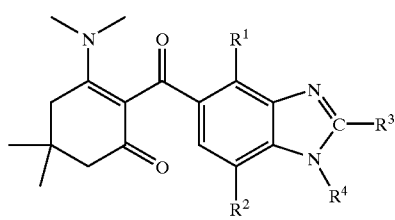

I-3l

Compounds of the formula I-3l, in which the substituents R¹, R², R³ and R⁴ for each individual compound correspond in each case to one row of Table B.

TABLE 62

Compounds I-3m.1 to I-3m.1363

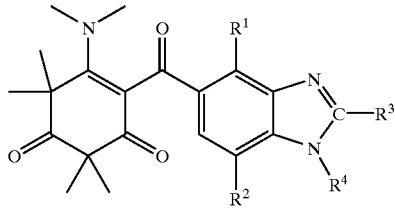

I-3m

Compounds of the formula I-3m, in which the substituents R¹, R², R³ and R⁴ for each individual compound correspond in each case to one row of Table B.

TABLE 63

Compounds I-3n.1 to I-3n.1363

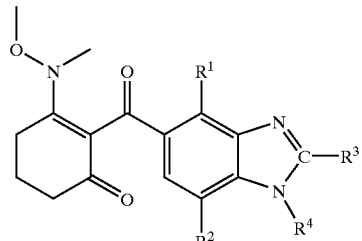

I-3n

Compounds of the formula I-3n, in which the substituents R¹, R², R³ and R⁴ for each individual compound correspond in each case to one row of Table B.

TABLE 64

Compounds I-3o.1 to I-3o.1363

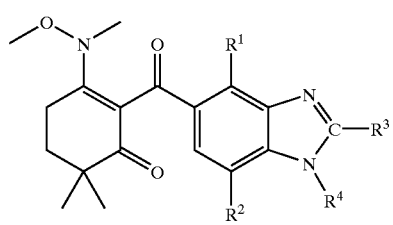

I-3o

Compounds of the formula I-3o, in which the substituents R¹, R², R³ and R⁴ for each individual compound correspond in each case to one row of Table B.

TABLE 65

Compounds I-3p.1 to I-3p.1363

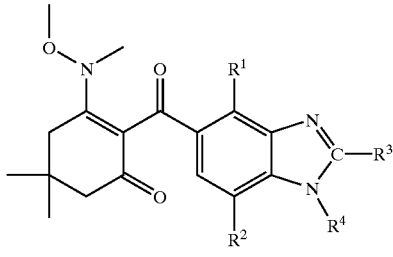

I-3p

Compounds of the formula I-3p, in which the substituents R¹, R², R³ and R⁴ for each individual compound correspond in each case to one row of Table B.

TABLE 66

Compounds I-3q.1 to I-3q.1363

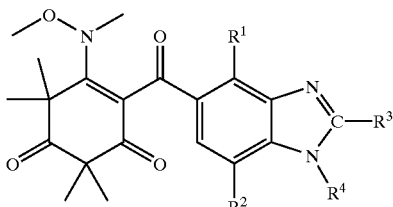

I-3q

Compounds of the formula-I-3q, in which the substituents R¹, R², R³ and R⁴ for each individual compound correspond in each case to one row of Table B.

TABLE 67

Compounds I-3r.1 to I-3r.1363

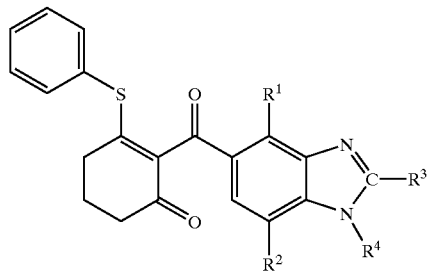

I-3r

Compounds of the formula I-3r, in which the substituents R¹, R², R³ and R⁴ for each individual compound correspond in each case to one row of Table B.

TABLE 68

Compounds I-3s.1 to I-3s.1363

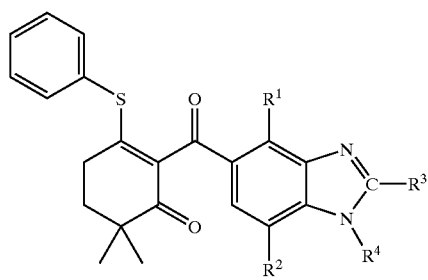

I-3s

Compounds of the formula I-3s, in which the substituents R¹, R², R³ and R⁴ for each individual compound correspond in each case to one row of Table B.

TABLE 69

Compounds I-3t.1 to I-3t.1363

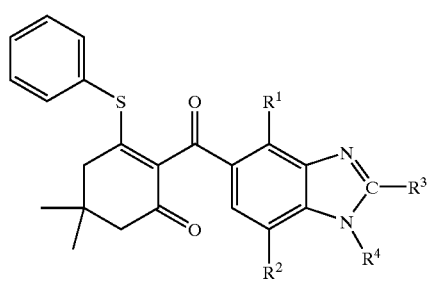

I-3t

Compounds of the formula I-3t, in which the substituents R¹, R², R³ and R⁴ for each individual compound correspond in each case to one row of Table B.

TABLE 70

Compounds I-3u.1 to I-3u.1363

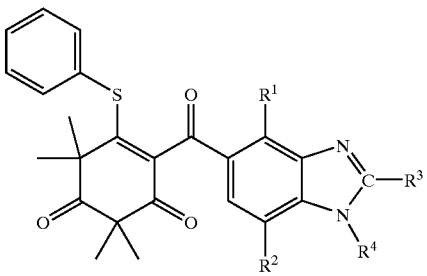

I-3u

Compounds of the formula I-3u, in which the substituents R¹, R², R³ and R⁴ for each individual compound correspond in each case to one row of Table B.

TABLE 71

Compounds I-3v.1 to I-3v.1363

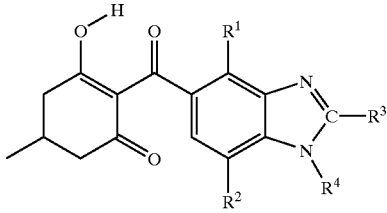

I-3v

Compounds of the formula I-3v, in which the substituents R¹, R², R³ and R⁴ for each individual compound correspond in each case to one row of Table B.

TABLE 72

Compounds I-3w.1 to I-3w.1363

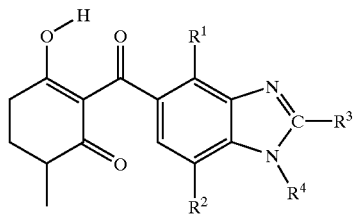

I-3w

Compounds of the formula I-3w, in which the substituents R¹, R², R³ and R⁴ for each individual compound correspond in each case to one row of Table B.

TABLE 73

Compounds I-3x.1 to I-3x.1363

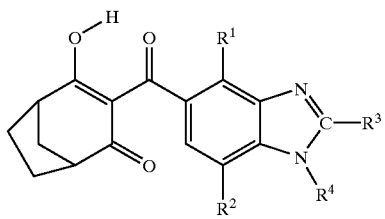

I-3x

Compounds of the formula I-3x, in which the substituents R¹, R², R³ and R⁴ for each individual compound correspond in each case to one row of Table B.

TABLE 74

Compounds I-3y.1 to I-3y.1363

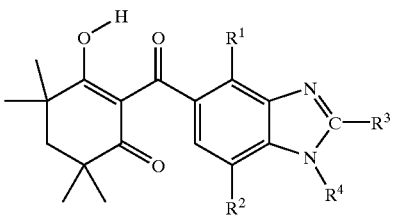

I-3y

Compounds of the formula I-3y, in which the substituents R¹, R², R³ and R⁴ for each individual compound correspond in each case to one row of Table B.

TABLE 75

Compounds I-3z.1 to I-3z.1363

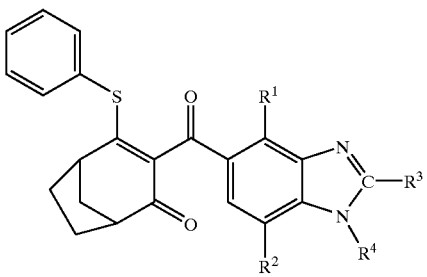

I-3z

Compounds of the formula I-3z, in which the substituents R¹, R², R³ and R⁴ for each individual compound correspond in each case to one row of Table B.

TABLE C

| | $R^1$ | $R^2$ | X | Y |
|---|---|---|---|---|
| 1 | H | H | N | S |
| 2 | $CH_3$ | H | N | S |
| 3 | Cl | H | N | S |
| 4 | $OCH_3$ | H | N | S |
| 5 | $SCH_3$ | H | N | S |
| 6 | $S(O)_2CH_3$ | H | N | S |
| 7 | H | Cl | N | S |
| 8 | $CH_3$ | Cl | N | S |
| 9 | Cl | Cl | N | S |
| 10 | $OCH_3$ | Cl | N | S |
| 11 | $SCH_3$ | Cl | N | S |
| 12 | $S(O)_2CH_3$ | Cl | N | S |
| 13 | H | $CH_3$ | N | S |
| 14 | $CH_3$ | $CH_3$ | N | S |
| 15 | Cl | $CH_3$ | N | S |
| 16 | $OCH_3$ | $CH_3$ | N | S |
| 17 | $SCH_3$ | $CH_3$ | N | S |
| 18 | $S(O)_2CH_3$ | $CH_3$ | N | S |
| 19 | H | H | N | NH |
| 20 | $CH_3$ | H | N | NH |
| 21 | Cl | H | N | NH |
| 22 | $OCH_3$ | H | N | NH |
| 23 | $SCH_3$ | H | N | NH |
| 24 | $S(O)_2CH_3$ | H | N | NH |
| 25 | H | Cl | N | NH |
| 26 | $CH_3$ | Cl | N | NH |
| 27 | Cl | Cl | N | NH |
| 28 | $OCH_3$ | Cl | N | NH |
| 29 | $SCH_3$ | Cl | N | NH |
| 30 | $S(O)_2CH_3$ | Cl | N | NH |
| 31 | H | $CH_3$ | N | NH |
| 32 | $CH_3$ | $CH_3$ | N | NH |
| 33 | Cl | $CH_3$ | N | NH |
| 34 | $OCH_3$ | $CH_3$ | N | NH |
| 35 | $SCH_3$ | $CH_3$ | N | NH |
| 36 | $S(O)_2CH_3$ | $CH_3$ | N | NH |
| 37 | H | H | N | $NCH_3$ |
| 38 | $CH_3$ | H | N | $NCH_3$ |
| 39 | Cl | H | N | $NCH_3$ |
| 40 | $OCH_3$ | H | N | $NCH_3$ |
| 41 | $SCH_3$ | H | N | $NCH_3$ |
| 42 | $S(O)_2CH_3$ | H | N | $NCH_3$ |
| 43 | H | Cl | N | $NCH_3$ |
| 44 | $CH_3$ | Cl | N | $NCH_3$ |
| 45 | Cl | Cl | N | $NCH_3$ |
| 46 | $OCH_3$ | Cl | N | $NCH_3$ |
| 47 | $SCH_3$ | Cl | N | $NCH_3$ |
| 48 | $S(O)_2CH_3$ | Cl | N | $NCH_3$ |
| 49 | H | $CH_3$ | N | $NCH_3$ |
| 50 | $CH_3$ | $CH_3$ | N | $NCH_3$ |
| 51 | Cl | $CH_3$ | N | $NCH_3$ |
| 52 | $OCH_3$ | $CH_3$ | N | $NCH_3$ |
| 53 | $SCH_3$ | $CH_3$ | N | $NCH_3$ |
| 54 | $S(O)_2CH_3$ | $CH_3$ | N | $NCH_3$ |
| 55 | H | H | N | $NC_2H_5$ |
| 56 | $CH_3$ | H | N | $NC_2H_5$ |
| 57 | Cl | H | N | $NC_2H_5$ |
| 58 | $OCH_3$ | H | N | $NC_2H_5$ |
| 59 | $SCH_3$ | H | N | $NC_2H_5$ |
| 60 | $S(O)_2CH_3$ | H | N | $NC_2H_5$ |
| 61 | H | Cl | N | $NC_2H_5$ |
| 62 | $CH_3$ | Cl | N | $NC_2H_5$ |
| 63 | Cl | Cl | N | $NC_2H_5$ |
| 64 | $OCH_3$ | Cl | N | $NC_2H_5$ |
| 65 | $SCH_3$ | Cl | N | $NC_2H_5$ |
| 66 | $S(O)_2CH_3$ | Cl | N | $NC_2H_5$ |
| 67 | H | $CH_3$ | N | $NC_2H_5$ |
| 68 | $CH_3$ | $CH_3$ | N | $NC_2H_5$ |
| 69 | Cl | $CH_3$ | N | $NC_2H_5$ |
| 70 | $OCH_3$ | $CH_3$ | N | $NC_2H_5$ |
| 71 | $SCH_3$ | $CH_3$ | N | $NC_2H_5$ |
| 72 | $S(O)_2CH_3$ | $CH_3$ | N | $NC_2H_5$ |
| 73 | H | H | N | $N\text{-}i\text{-}C_3H_7$ |
| 74 | $CH_3$ | H | N | $N\text{-}i\text{-}C_3H_7$ |
| 75 | Cl | H | N | $N\text{-}i\text{-}C_3H_7$ |
| 76 | $OCH_3$ | H | N | $N\text{-}i\text{-}C_3H_7$ |
| 77 | $SCH_3$ | H | N | $N\text{-}i\text{-}C_3H_7$ |
| 78 | $S(O)_2CH_3$ | H | N | $N\text{-}i\text{-}C_3H_7$ |
| 79 | H | Cl | N | $N\text{-}i\text{-}C_3H_7$ |
| 80 | $CH_3$ | Cl | N | $N\text{-}i\text{-}C_3H_7$ |
| 81 | Cl | Cl | N | $N\text{-}i\text{-}C_3H_7$ |

TABLE C-continued

| | R¹ | R² | X | Y |
|---|---|---|---|---|
| 82 | OCH$_3$ | Cl | N | N-i-C$_3$H$_7$ |
| 83 | SCH$_3$ | Cl | N | N-i-C$_3$H$_7$ |
| 84 | S(O)$_2$CH$_3$ | Cl | N | N-i-C$_3$H$_7$ |
| 85 | H | CH$_3$ | N | N-i-C$_3$H$_7$ |
| 86 | CH$_3$ | CH$_3$ | N | N-i-C$_3$H$_7$ |
| 87 | Cl | CH$_3$ | N | N-i-C$_3$H$_7$ |
| 88 | OCH$_3$ | CH$_3$ | N | N-i-C$_3$H$_7$ |
| 89 | SCH$_3$ | CH$_3$ | N | N-i-C$_3$H$_7$ |
| 90 | S(O)$_2$CH$_3$ | CH$_3$ | N | N-i-C$_3$H$_7$ |

Other examples of benzothiadiazol-5-ylcarbonyl derivatives of cyclohexenones (X=N, Y=S) and benzotriazol-5-ylcarbonyl derivatives of cyclohexenones (X=N, Y=N—R⁴) which are preferred according to the invention are the compounds listed in Tables 76 to 100 (compounds I-4).

TABLE 76

Compounds I-4a.1 to I-4a.90

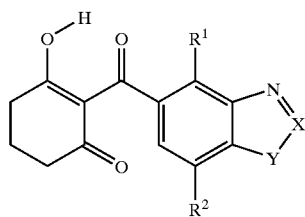

I-4a

Compounds of the formula I-4a, in which the substituents R¹, R², X and Y for each individual compound correspond in each case to one row of Table C.

TABLE 77

Compounds I-4b.1 to I-4b.90

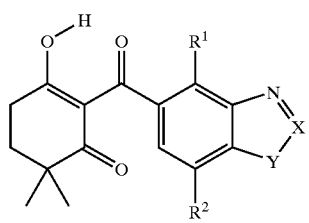

I-4b

Compounds of the formula I-4b, in which the substituents R¹, R², X and Y for each individual compound correspond in each case to one row of Table C.

TABLE 78

Compounds I-4c.1 to I-4c.90

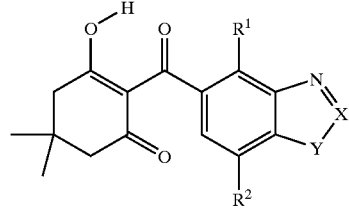

I-4c

Compounds of the formula I-4c, in which the substituents R¹, R², X and Y for each individual compound correspond in each case to one row of Table C.

TABLE 79

Compounds I-4d.1 to I-4d.90

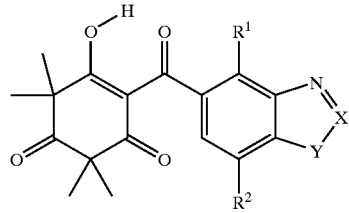

I-4d

Compounds of the formula I-4d, in which the substituents R¹, R², X and Y for each individual compound correspond in each case to one row of Table C.

TABLE 80

Compounds I-4e.1 to I-4e.90

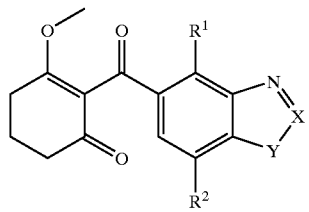

I-4e

Compounds of the formula I-4e, in which the substituents R¹, R², X and Y for each individual compound correspond in each case to one row of Table C.

TABLE 81

Compounds I-4f.1 to I-4f.90

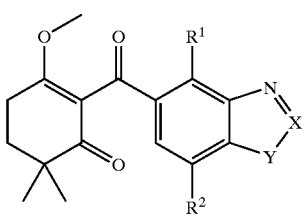

I-4f

Compounds of the formula I-4f, in which the substituents R¹, R², X and Y for each individual compound correspond in each case to one row of Table C.

TABLE 82

Compounds I-4g.1 to I-4g.90

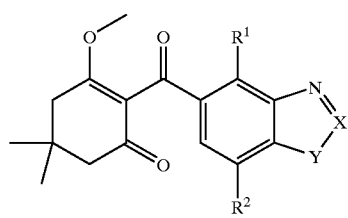

I-4g

Compounds of the formula I-4g, in which the substituents R¹, R², X and Y for each individual compound correspond in each case to one row of Table C.

TABLE 83

Compounds I-4h.1 to I-4h.90

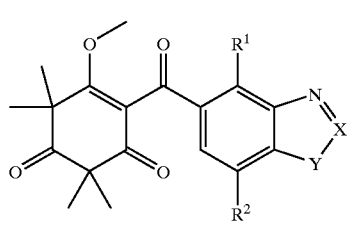

I-4h

Compounds of the formula I-4h, in which the substituents R¹, R², X and Y for each individual compound correspond in each case to one row of Table C.

TABLE 84

Compounds I-4i.1 to I-4i.90

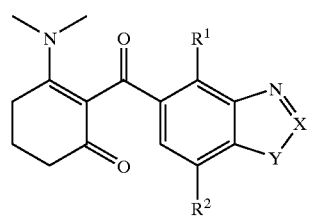

I-4i

Compounds of the formula I-4i, in which the substituents R¹, R², X and Y for each individual compound correspond in each case to one row of Table C.

TABLE 85

Compounds I-4k.1 to I-4k.90

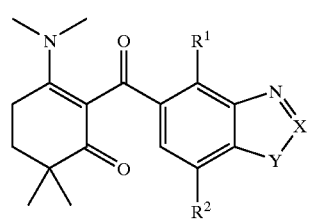

I-4k

Compounds of the formula I-4k, in which the substituents R¹, R², X and Y for each individual compound correspond in each case to one row of Table C.

TABLE 86

Compounds I-4l.1 to I-4l.90

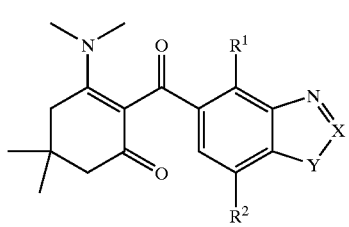

I-4l

Compounds of the formula I-4i, in which the substituents R¹, R², X and Y for each individual compound correspond in each case to one row of Table C.

TABLE 87

Compounds I-4m.1 to I-4m.90

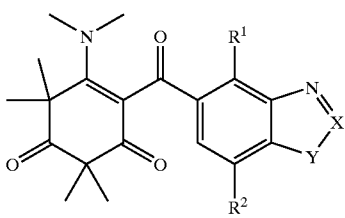

I-4m

Compounds of the formula I-4m, in which the substituents R¹, R², X and Y for each individual compound correspond in each case to one row of Table C.

TABLE 88

Compounds I-4n.1 to I-4n.90

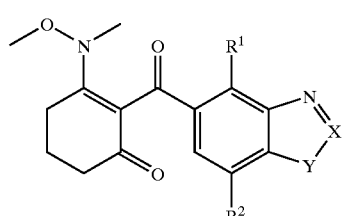

I-4n

Compounds of the formula I-4n, in which the substituents R¹, R², X and Y for each individual compound correspond in each case to one row of Table C.

TABLE 89

Compounds I-4o.1 to I-4o.90

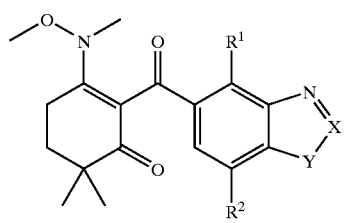

I-4o

Compounds of the formula I-4o, in which the substituents R¹, R², X and Y for each individual compound corresponding each case to one row of Table C.

TABLE 90

Compounds I-4p.1 to I-4p.90

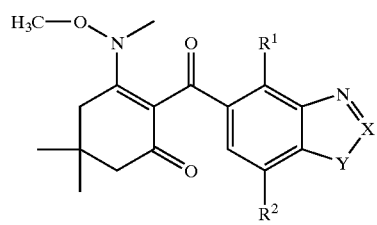

I-4p

Compounds of the formula I-4p, in which the substituents R¹, R², X and Y for each individual compound correspond in each case to one row of Table C.

TABLE 91

Compounds I-4q.1 to I-4q.90

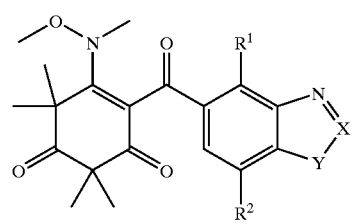

I-4q

Compounds of the formula I-4q, in which the substituents R¹, R², X and Y for each individual compound correspond in each case to one row of Table C.

TABLE 92

Compounds I-4r.1 to I-4r.90

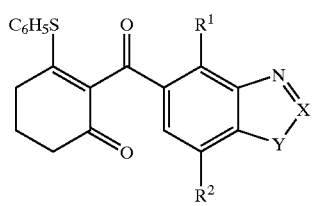

I-4r

Compounds of the formula I-4r, in which the substituents R¹, R², X and Y for each individual compound correspond in each case to one row of Table C.

TABLE 93

Compounds I-4s.1 to I-4s.90

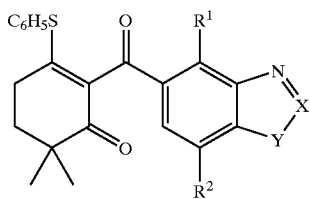

I-4s

Compounds of the formula I-4s, in which the substituents R¹, R², X and Y for each individual compound correspond in each case to one row of Table C.

TABLE 94

Compounds I-4t.1 to I-4t.90

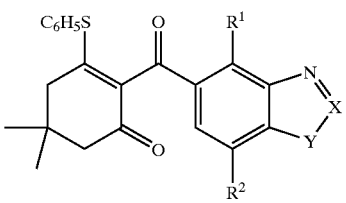

I-4t

Compounds of the formula I-4t, in which the substituents R¹, R², X and Y for each individual compound correspond in each case to one row of Table C.

TABLE 95

Compounds I-4u.1 to I-4u.90

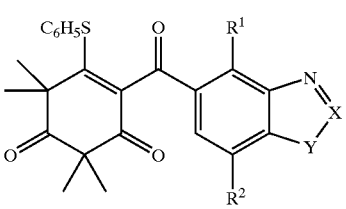

I-4u

Compounds of the formula I-4u, in which the substituents R¹, R², X and Y for each individual compound correspond in each case to one row of Table C.

TABLE 96

Compounds I-4v.1 to I-4v.90

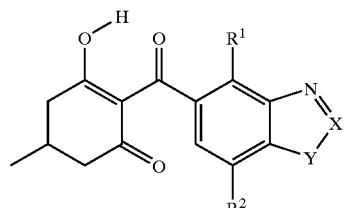

I-4v

Compounds of the formula I-4v, in which the substituents R¹, R², X and Y for each individual compound correspond in each case to one row of Table C.

TABLE 97

Compounds I-4w.1 to I-4w.90

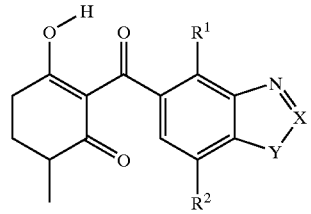

I-4w

Compounds of the formula I-4w, in which the substituents R¹, R², X and Y for each individual compound correspond in each case to one row of Table C.

TABLE 98

Compounds I-4x.1 to I-4x.90

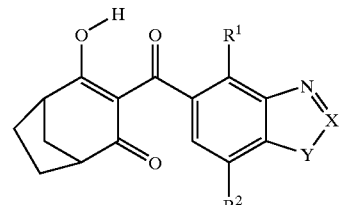

I-4x

Compounds of the formula I-4x, in which the substituents R¹, R², X and Y for each individual compound correspond in each case to one row of Table C.

TABLE 99

Compounds I-4y.1 to I-4y.90

I-4y

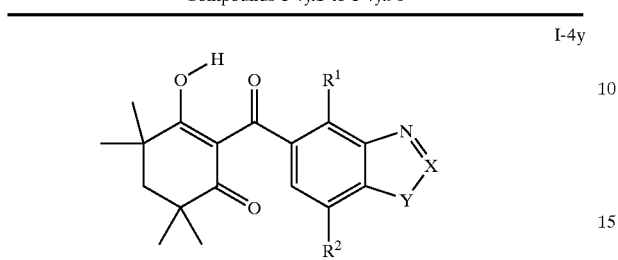

Compounds of the formula I-4y, in which the substituents R¹, R², X and Y for each individual compound correspond in each case to one row of Table C.

TABLE 100

Compounds I-4z.1 to I-4z.90

I-4z

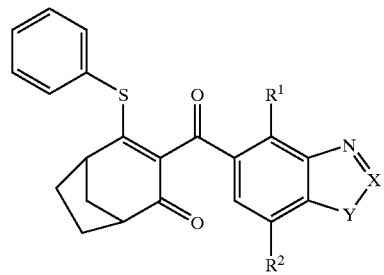

Compounds of the formula I-4z, in which the substituents R¹, R², X and Y for each individual compound correspond in each case to one row of Table C.

Compounds of the formula I where $R^8$ is hydroxyl are prepared by reacting an activated carboxylic acid IVb or a carboxylic acid IVa, which is preferably activated in situ, with a cyclohexane-1,3-dione of the formula III to give the acylation product, followed by rearrangement.

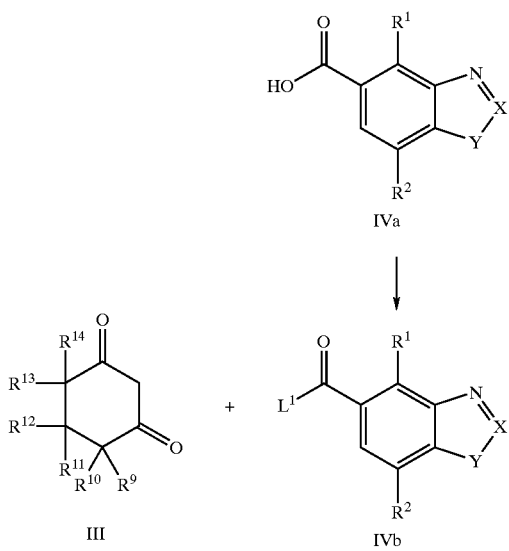

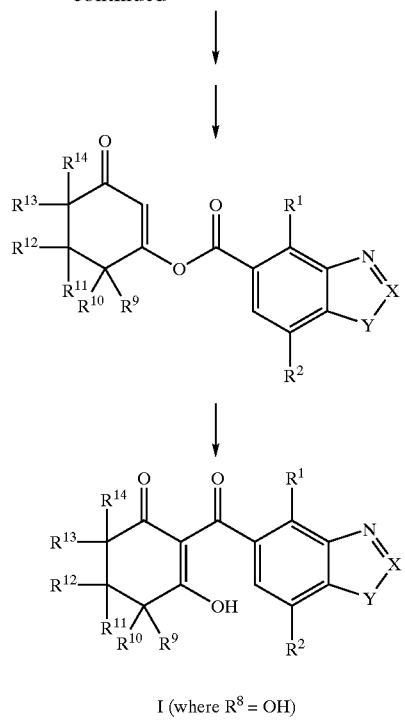

I (where $R^8$ = OH)

$L^1$ is a nucleophilically displaceable leaving group, such as halogen, for example bromine or chlorine, hetaryl, for example imidazolyl or pyridyl, carboxylate, for example acetate or trifluoroacetate, etc.

The activated carboxylic acid IVa can be employed directly, such as in the case of the benzoyl halides, or be generated in situ, for example using a carbodiimide, such as ethyl-(3'-dimethylaminopropyl)carbodiimide, dicyclohexylcarbodiimide, triphenylphosphine/ azodicarboxylic ester, 2-pyridine disulfide/ triphenylphosphine, carbonyldiimidazole, etc.

If appropriate, it may be advantageous to carry out the acylation reaction in the presence of a base. Here, the reactants and the auxiliary base are advantageously employed in equimolar amounts. In some cases, it may be advantageous to employ a slight excess of the auxiliary base, for example from 1.2 to 1.5 molar equivalents, based on IVa or IVb.

Suitable auxiliary bases are tertiary alkylamines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component used is a halide, it may be advantageous to cool the reaction mixture to 0–10° C. when adding this reactant. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. After the organic phase has been dried and the solvent has been removed, the crude ester can be employed for the rearrangement without further purification.

The rearrangement of the esters to give the compounds of the formula I is advantageously carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in an equimolar amount or an up.to 4-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetonecyanohydrin or trimethylsilyl cyanide. They are employed in an amount of 1–50 mol percent, based on the ester. Preference is given to using acetonecyanohydrin or trimethylsilyl cyanide, for example in an amount of 5–15, preferably about 10 mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the precipitate that is formed is filtered off with suction and/or extracted with methylene chloride or ethyl acetate, dried and concentrated.

B. Preparation of compounds of the formula I where $R^8$=halogen is carried out by reacting cyclohexenone derivatives of the formula I (where $R^8$=hydroxyl) with halogenating agents:

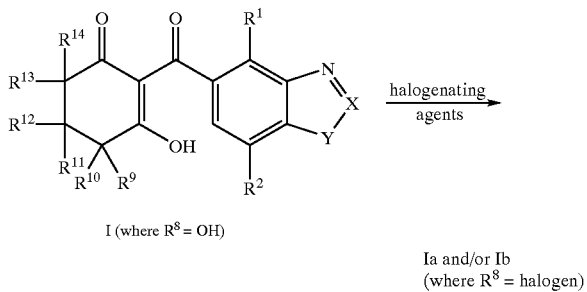

Here and below, "compound Ia" is a compound of the formula I where hex is a radical of the formula IIa and, correspondingly, compound Ib is a compound of the formula I where hex is a radical of the formula IIb.

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

C. Compounds of the formula I where $R^8$=$OR^{15}$, $OSO_2R^{16}$, $OPOR^{17}R^{12}$ or $OPSR^{17}R^{18}$ are prepared by reacting cyclohexenone derivatives of the formula I (where $R^8$=hydroxyl) with alkylating, sulfonylating or phosphonylating agents $V\alpha$, $V\beta$, $V\gamma$ and $V\delta b$, respectively.

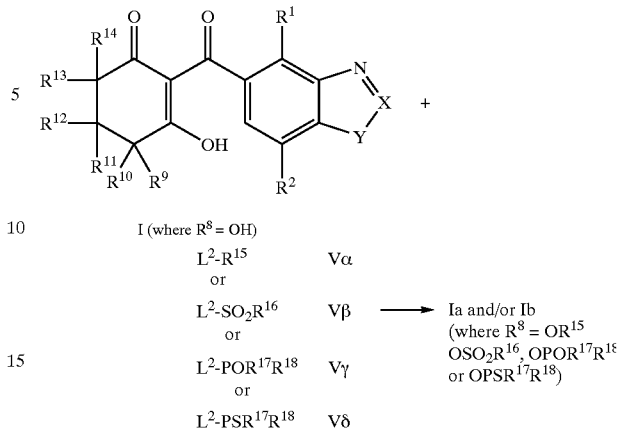

$L^2$ is a nucleophilically displaceable leaving group, such as halogen, for example chlorine or bromine, hetaryl, for example imidazolyl, carboxylate, for example aceate, or sulfonate, for example mesylate or triflate, etc.

Compounds of the formula $V\alpha$, $V\beta$, $V\gamma$ or $V\delta$ can be employed directly, such as in the case of the carbonyl halides, or be generated in situ, for example activated carboxylic acids (using carboxylic acid and dicyclohexylcarbodiimide, etc.).

D. Compounds of the formula I where $R^8$=$OR^{15}$, $SR^{15}$, $POR^{17}R^{18}$, $NR^{19}R^{20}$, $ONR^{19}R^{20}$ or N-bonded heterocyclyl are prepared by reacting compounds of the formula I where $R^8$=halogen, $OSO_2R^{16}$ with compounds of the formula $VI\alpha$, $VI\beta$, $VI\gamma$, $VI\delta$, $VI\epsilon$ or $VI\eta$, if appropriate in the presence of a base or with prior formation of salt.

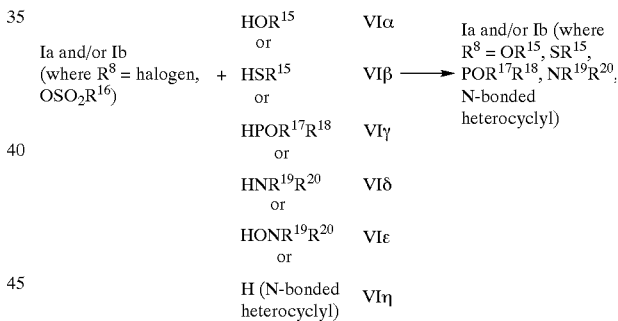

E. Compounds of the formula I where $R^8$=$SOR^{16}$, $SO_2R^{16}$ are prepared, for example, by reacting compounds of the formula I where $R^8$=$SR^{16}$ with an oxidizing agent.

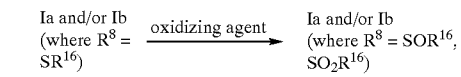

Suitable oxidizing agents are, for example, m-chloroperbenzoic acid, peroxyacetic acid, trifluoroperoxyacetic acid, hydrogen peroxide, if appropriate in the presence of a.catalyst, such as tungstate.

For the reactions mentioned under points B to E, the following conditions apply:

The starting materials are.generally employed in equimolar amounts. However, it may also be advantageous to employ an excess of one or the other component.

If appropriate, it may be advantageous to carry out the reactions in the presence of a base. Reactants and base are advantageously employed in equimolar amounts.

With respect to the processes C and D, it may, in certain cases, be advantageous to employ an excess of base, for example 1.5 to 3 molar equivalents, in each case based on the starting material.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

Depending on the reaction conditions, in the processes B to D the compounds Ia, Ib, or mixtures of these can be formed. The latter can be separated by classic separation methods, for example crystallization, chromatography, etc.

The cyclohexanedions of the formula IV used as starting materials are known or can be prepared by processes known per se (for example EP-A 71 707, EP-A 142 741, EP-A 243 313, U.S. Pat. No. 4,249,937, WO 92/13821).

The alkylating agents Vα, sulfonylating agents Vβ, phosphonylating agents Vγ and Vδ, and the compounds VIα, VIβ, VIγ, Vδ and VIε are likewise known, or they can be prepared by known processes.

The carboxylic acids of the formula IVa and their activated derivatives IVb are either known from the literature, or they can be prepared analogously to known processes.

Scheme 1 shows a customary route to benzothiazole-5-carboxylic acids (compounds IV-1).

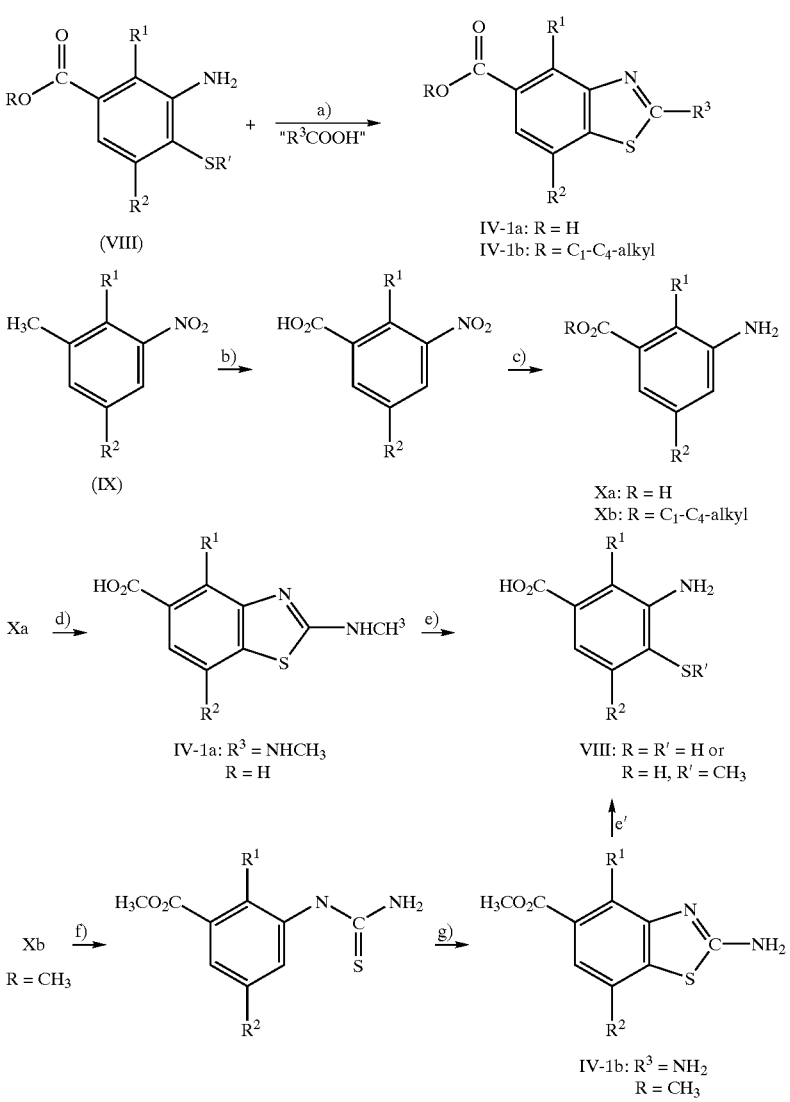

In the formula IV-1, R is hydrogen (compound IV-1a) or a hydrocarbon radical which can be hydrolyzed, for example methyl (compound IV-1b). Compounds of the formula IV-1 can be prepared, for example, according to reaction step a) by condensation of ortho-aminothiophenols of the formula VIII (R'=H) or of ortho-aminothioethers of the formula VIII (R'=$C_1$–$C_4$-alkyl, for example methyl), using a carboxylic acid equivalent "$R^3$—$CO_2H$" i.e. a carboxylic acid $R^3CO_2H$ or activated derivatives $R^3COL^1$, $R^3C(L^3)_3$ thereof where $L^1$ is a reactive leaving group and $L^3$ is a $C_1$–$C_4$-alkoxy group. Examples of $L^1$ are chlorine, bromine, carboxylate, such as acetate, trifluoroacetate, N-heterocyclyl, such as imidazolyl, pyridyl etc. Examples of $R^3COL^1$ and $R^3C(L^3)_3$ are acyl halides, carboxylic esters and carboxylic anhydrides, and the ortho esters of the carboxylic acids $R^3CO_2H$.

The condensation reaction a) is preferably carried out under neutral to acidic reaction conditions, preferably in the presence of an inorganic or organic acid, for example hydrochloric acid, sulfuric acid, p-toluenesulfonic acid and pyridinium p-toluenesulfonate, in an organic solvent at 0–150° C., preferably in the range from 20 to 120° C. Suitable solvents are, in particular, saturated hydrocarbons, halogenated hydrocarbons, aromatic hydrocarbons, such as benzene, aliphatic ethers, such as diethyl ether and tert-butyl methyl ether, or pyridine. For the preparation of benzothiazoles from o-aminothiophenols or corresponding thiomethyl ethers, see also Houben-Weyl,-Methoden der Organischen Chemie, Vol. E 8b, pp.869–871.

Step a) can also be carried out in two steps, by initially converting the amino function in VIII with a carboxylic acid $R^9$—COOH or a derivative thereof into the carboxamide, which is subsequently cyclized to give the benzothiazole of the formula IV-1.

The conversion into the amide is carried out under the conditions which are customary for amide formation, for example by reacting an acid in the presence of a water-binding agent. Cyclization is carried out with Lewis acids or phosgene. In this case, the cyclization is preferably carried out in an inert organic solvent, for example an aliphatic or aromatic hydrocarbon, or in a halogenated hydrocarbon.

According to Scheme 1, ortho-aminothiophenols of the formula VIII (R'=H) can be prepared starting with 3-nitrotoluenes of the formula IX. The methyl group can be oxidized in a known manner, catalytically or stoichiometrically, to give the carboxylic acid (step b). Suitable oxidizing agents are, for example, metal oxides of transition metals, for example manganese dioxide, chromium trioxide and their anionic complex salts, for example sodium dichromate or chromyl chloride, pyridinium chromate, furthermore oxidizing acids, for example $HNO_3$, oxidizing gases, such as oxygen or chlorine, if appropriate in the presence of transition metals (or salts thereof, for example oxides or chlorides) as catalysts. Depending on the solubility of the compound to be oxidized and depending on the oxidizing agent used, the reaction is preferably carried out in aqueous solutions, monophasic systems of water and water-miscible organic solvents or in multiphasic systems of water and organic solvents with phase-transfer catalysis. Depending on the chosen oxidizing agent, the oxidation is generally carried out in.the range from –15 to +150° C., preferably in the range from 0 to 100° C. For the oxidation of aromatic methyl.groups to benzoic acids, see, for example, Houben-Weyl: "Methoden der organischen Chemie", Vol. V, IV/1a, 1981; Vol. VIII 1952; E. Bengtsson, Acta Chem. Scand. 7 (1953), 774; Singer et al., Org. Synth. Coll. Vol III, 1955, 740; B. A. S. Hay et al., Can. J. Chem. 43 (1965), 1306).

The resulting 3-nitrobenzoic acid derivatives are subsequently, in step c), reduced to the 3-aminobenzoic acids. The selective reduction of aromatic nitro groups in the presence of carboxylic acid groups is known in principle. Suitable reducing agents are, for example, hydrazines, metal hydrides, such as aluminum hydride, and complex compounds derived therefrom, such as lithium aluminum hydride, diisobutylaluminum hydride or boranes. The preferred reducing agent is hydrogen in the presence of catalytic amounts of transition metals, for example Ni, Pd, Pt, Ru or Rh, which may be employed in supported form, for example on active carbon, in the form of activated metals, for example Raney nickel, or in the form of soluble complex compounds. Suitable solvents for the reduction are, depending on the solubility of the substrate to be hydrogenated and the chosen reducing agent, $C_1$–$C_4$-alcohols, such as methanol, ethanol, n-propanol, isopropanol or n-butanol, halogenated $C_1$–$C_6$-hydrocarbons, such as dichloromethane, trichloromethane, trichloroethane, trichloroethylene, aromatic hydrocarbons, such as benzene, toluene, xylenes, chlorobenzene, aqueous solutions of inorganic or organic acids, such as aqueous hydrochloric acid. The reduction is usually carried out in the range from –15 to +100° C., preferably in the range from 0 to 40° C. The reduction with hydrogen is usually carried out at a hydrogen pressure in the range from 1 to 50 bar, preferably in the range from 1 to 10 bar. For the catalytic hydrogenation of aromatic nitro groups, see, for example, Rylander in "Catalytic Hydrogenation over Platinum Metals", Academic Press, New York, 1967, 168–202; Furst et al., Chem. Rev. 65 (1965), 52; Tepko et al., J. Org. Chem. 45 (1980), 4992.

The resulting m-aminobenzoic acids of the formula Xa (R=H) are then, in a further reaction step d), reacted with an organic isothiocyanate (in scheme 1 methyl isothiocyanate) to give a substituted thiourea derivative which, without further isolation, is cyclized oxidatively to give the benzothiazole-5-carboxylic acid of the formula IX-1a (in scheme 1 with $R^3$=NH—$CH_3$).

The first reaction step in step d), i.e. the conversion of the m-aminobenzoic acid of the formula Xa into the substituted urea is carried out by reaction with a $C_1$–$C_6$-alkyl isothiocyanate or an unsubstituted or substituted phenyl isothiocyanate in an anhydrous organic solvent at from –15° C. to 150° C., preferably in the range from –15° C. to 100° C. Suitable solvents are, for example, aliphatic or cycloaliphatic hydrocarbons, such as n-hexane or cyclohexane, halogenated hydrocarbons, such as dichloromethane, trichloromethane, trichloroethane, trichloroethylene, aromatic hydrocarbons, such as benzene or anisole, dialkyl ethers or cyclic ethersi such as diethyl ether, methyl tert-butyl ether, tetrahydrofuran or dioxane, anhydrous carboxylic acids, such as glacial acetic acid, or pyridine. For the preparation of substituted thioureas see, for example: F. Kurzer, Org. Synth. 31 (1951), 21; R. R. Gupta et al., Synth. Commun. 17(2) (1987), 229–240; Rathke, Ber. Dtsch. Chem. Ges. 18 (1885), 3102; Schiff, Justus Liebigs Ann. Chem. 148 (1868), 338; R. L. Frank, P. V. Smith, Org. Synth. III (1955), 735, N. B. Ambati et al., Synth. Commun. 27 (9) (1997), 1487–1493; W. O. Foye, J. Pharm. Sci. 66 (7) (1977), 923–926.

The resulting substituted thiourea derivative is then, in a second reaction step of step d), cyclized using a halogen-containing oxidizing agent, such as bromine, sulfuryl chloride or chlorine in an inert organic solvent, to give the substituted 2-aminobenzothiazole-5-carboxylic acid of the general formula IV-1a (in scheme 1, $R^3$ is NH—$CH_3$). The cyclization is generally carried out in the range from –15 to +150° C., preferably in the range from 0 to 120° C. Suitable solvents are, in particular, the abovementioned aliphatic or cycloaliphatic hydrocarbons, the abovementioned aromatic hydrocarbons, the abovementioned anhydrous carboxylic acids, and furthermore $C_1$–$C_4$-alkanols, for example methanol, ethanol or isopropanol, dialkyl ethers, cyclic ethers and mixtures of the abovementioned solvents. For the oxidative cyclization of substituted thioureas to benzothiazoles see, for example, Houben-Weyl: "Methoden der organischen Chemie" V, Vol. E8B, 1994, p.865 f.

The substituted 2-aminobenzothiazole-5-carboxylic acid of the formula IV-1a can either be reacted directly in the abovementioned manner with a cyclohexane-1,3-dione of the formula III or an activated derivative thereof to give the compound I according to the invention (where Y=S and X=C—NH—R''', where R'' is $C_1$–$C_6$-alkyl or unsubstituted or substituted phenyl).

If $R^3$ in the formula IV-1a is NH—$CH_3$, it is also possible to prepare the o-aminothiobenzoic acids of the formula VIII (where R=R'=H) by hydrolysis according to step e). The hydrolysis is generally followed by the methylation to give the methyl thioether VIII (R=H, R'=$CH_3$). The hydrolysis in step e) is carried out, for example, by reacting the compound IV-1a (where $R^3$=NH—$CH_3$) with an alkali metal hydroxide, for example lithium hydroxide, sodium hydroxide or potassium hydroxide, an alkaline earthmetal hydroxide or an alkali metal iodide, such as sodium iodide, in a suitable solvent at elevated temperature, the reaction preferably being carried out in the absence of oxygen. Customary reaction temperatures are in the range from 0 to 200° C., in particular in the range from 20 to 180° C. Suitable solvents are, in addition to the abovementioned aliphatic or cycloaliphatic hydrocarbons, the halogenated hydrocarbons, the aromatic hydrocarbons, the abovementioned ethers and alcohols, in particular aqueous monophasic systems and pyridine. For the hydrolysis of the substituted 2-aminobenzothiazole-5-carboxylic acids see, for example: Organikum, 16th edition 1986, p. 415; Mc Murry, Org. React. 24 (1976), 187; Taschner et al., Rocz. Chem. 30 (1956), 323; Houben-Weyl: "Methoden der organischen Chemie", Volume E8b, 1994, p. 1010 f.; J. Chem. Soc. Perkin Trans., Part 1, No. 12, (1976), 1291–1296, in particular A. R. Katritzky et al., J. Heterocycl. Chem. 30 (1) (1993), 135–139. The conversion into the methyl thioether VIII where R=H and R'=$CH_3$ is carried out in a simple manner by reacting with methyl iodide or dimethyl sulfate.

In a similar manner, it is possible to obtain compounds of the formula VIII where R=H by initially esterifying the 3-aminobenzoic acid of the formula Xa with a $C_1$–$C_4$-alkanol, for example with methanol, in a known manner. The resulting ester of the formula Xb (R=$C_1$–$C_4$-alkyl, in particular methyl) is then, in step f), reacted with isothiocyanic acid or a suitable salt of isothiocyanic acid, for example sodium isothiocyanate, in the presence of a concentrated mineral acid, to give the thiourea derivative. The reaction conditions correspond to the reaction conditions mentioned under step d) for the urea derivatives. The thiourea derivative is subsequently, in step g), cyclized under the abovementioned conditions to give the 2-aminobenzothiazole-5-carboxylic ester of the formula IV-1b ($R^3$=$NH_2$). The resulting compound of the formula IV-1b where $R^3$=$NH_2$ can be hydrolyzed in step et) to give the compound VIII, which is subsequently, if appropriate, methylated (VIII: R=H, R'=$CH_3$).

It is also possible to convert the compound IV-1b in the manner described above into the compound I according to the invention (where X=C-$NH_2$ and Y=S). Moreover, it is possible to initially diazotize the 2-amino group of the compound IV-1b and to introduce further functionalities into the 2-position of the benzothiazole skeleton in this way. The conversion of $R^3$=$NH_2$ into $R^3$=halogen is carried out in a known manner under Sandmeyer conditions. The conversion of $R^3$=$NH_2$ into $R^3$=H is carried out in a known manner by successive reaction of the 2-aminobenzothiazole-5-carboxylic ester with nitrite under acid conditions and then with a reducing agent, such as hypophosphoric acid, sodium borohydride, trialkylsilanes, trialkylstannanes, $SnCl_2$, NO, Wilkinson catalysts; see also J. Am. Chem. Soc. 71 (1949), p. 2137; J. Am. Chem. Soc. 72 (1950), p. 3013; 76 (1954), p. 290.

A further route to the compounds of the formula VIII is shown in scheme 2.

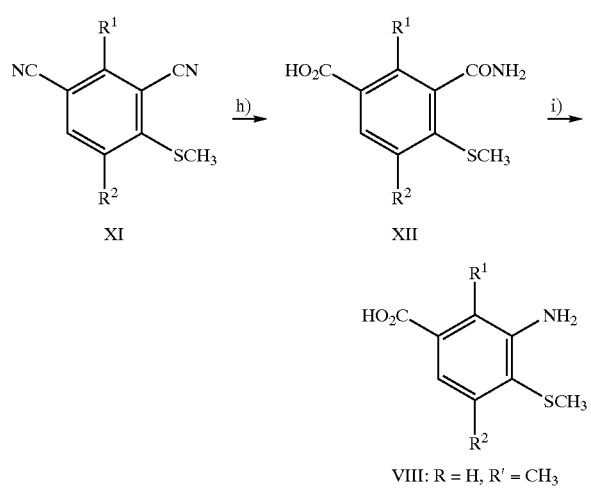

Starting from 2,4-dicyanothioanisoles of the formula XI, in step h) the amide of the formula XII is prepared by selective hydrolysis. Owing to the different reactivity of the two methyl groups, the preparation is carried out under customary alkaline hydrolysis conditions, but the progress of the reaction is preferably monitored. Methods for the alkaline hydrolysis of nitriles are known, for example, from Org. Synth. Coll. Vol. 1, 1941, p. 321. In a further step i), the amide function in the compounds of the formula XII is then converted into an amino function by Hofmann degradation. This gives compounds of the formula VIII where R=H and R'=$CH_3$. Typical conditions for the Hofmann degradation are: aqueous alkaline chlorine or hypochloride solutions, temperatures in the range from 0 to 150° C., preferably in the range from 20 to 120° C. (see also Organikum, 16th edition 1986, p. 572).

A further route to benzothiazole-5-carboxylic acids is shown in scheme 3. This route utilizes the conversion of benzothiazoles of the formula XIV into the corresponding carboxylic acids, as shown in reaction step o).

Scheme 3

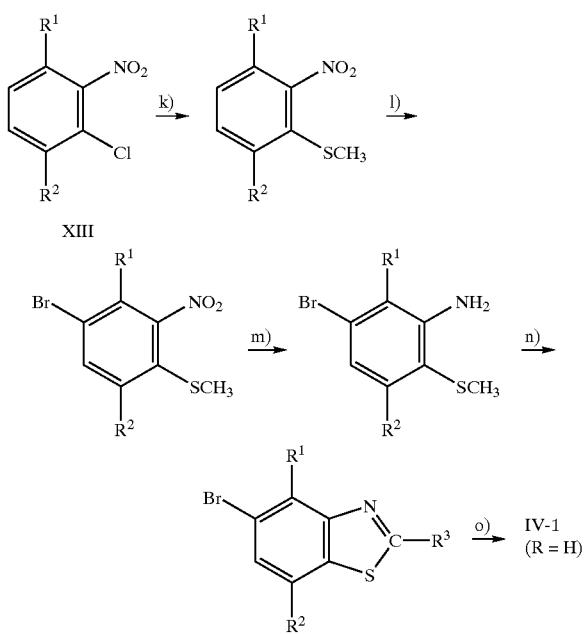

The conversion of the bromobenzothiazole of the formula XIV into the carboxylic acid of the formula IV-1 (R=H) is carried out, for example, by successive reaction of XIV with magnesium to give the corresponding Grignard compound and subsequent reaction of the Grignard compound with carbon dioxide. Alternatively, the compound XIV can be converted into the compound IV-1 by halogen-metal exchange using an alkali metal alkyl, for example a lithium alkyl, such as methyllithium, n-butyllithium or tert-butyllithium, and subsequent reaction of the reaction product with $CO_2$.

Reaction step o) in scheme 3 can also be realized by reacting the 5-bromobenzothiazole of the formula XIV with carbon monoxide, a base and water, under elevated pressure in the presence of a Pd, Ni, Co or Rh catalyst.

The catalysts nickel, cobalt, rhodium and in particular palladium can be present in metallic form or in the form of customary salts, such as in the form of halogen compounds, for example $PdCl_2$, $RhCl_3 \cdot H_2O$, acetates, for example $Pd(OAc)_2$, cyanides,- etc., in the known valence states. Metal complexes with tertiary phosphines, metal alkylcarbonyls, metal carbonyls, e.g. $CO_2(CO)_8$, $Ni(CO)_4$, metal carbonyl complexes with tertiary phosphines, e.g. $(PPh_3)_2Ni(CO)_2$, or transition metal salts complexed with tertiary phosphines can also be present. The last-mentioned embodiment is preferred, in particular when the catalyst used is palladium. Here, the type of phosphine ligands is widely variable. They can be represented, for example, by the following formulae:

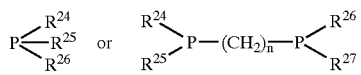

where n is the number 1, 2, 3 or 4 and the radicals $R^{24}$ to $R^{26}$ are low-molecular-weight alkyl, for example $C_1$–$C_6$-alkyl, aryl, $C_1$–$C_4$-alkylaryl, for example benzyl or phenethyl, or aryloxy. Aryl is, for example, naphthyl, anthryl and preferably unsubstituted or substituted phenyl, where, with respect to the substituents, attention has to be paid only to their inertness to the carboxylation reaction, otherwise they can be widely varied and include all inert organocarbon radicals, such as $C_1$–$C_6$-alkyl radicals, for examplemethyl, carboxyl radicals, such as COOH, COOM (M is, for example, an alkali metal, alkaline earth metal or ammonium salt), ororganocarbon radicals attached via oxygen, such as $C_1$–$C_6$-alkoxy radicals.

The phosphine complexes can be prepared in a manner known per se, for example as described in the documents mentioned at the outset. For example, customary commercially available metal salts such as $PdCl_2$ or $Pd(OCOCH_3)_2$ are used as starting materials and the phosphine, for example $P(C_6H_5)_3$, $P(n\text{---}C_4H_9)_3$, $PCH_3(C_6H_5)_2$, 1,2-bis (diphenylphosphino)ethane, is added.

The amount of phosphine, based on the transition metal, is usually from 0 to 20, in particular from 0.1 to 10, molar equivalents, particularly preferably.from 1 to 5 molar equivalents.

The amount of transition metal is not critical. Of course, for reasons of cost, preference is given to using a small amount, for example from 0.1 to 10 mol%, in particular from 1 to 5 mol%, based on the starting material IV.

For preparing the benzothiazole-5-carboxylic acids IV-1 (R=OH), the reaction is carried out with carbon monoxide and at least equimolar amounts of water, based on the starting materials XIV. The reaction component water can simultaneously also serve as solvent, i.e. the maximum amount is not critical.

However, depending on the nature of the starting materials and the catalysts used, it may also be advantageous for the solvent used to be, instead of the reaction component, another inert solvent or the base which is used for the carboxylation.

Suitable inert solvents for carboxylation reactions are customary solvents such as hydrocarbons, for example toluene, xylene, hexane, pentane, cyclohexane, ethers, for example methyl tert-butyl ether, tetrahydrofuran, dioxane, dimethoxyethane, substituted amides, such as dimethylformamide, persubstituted ureas, such as tetra-$C_1$–$C_4$-alkylureas, or nitriles, such as benzonitrile or acetonitrile.

In a preferred embodiment of the process, one of the reaction components, in particular the base, is used in an excess, so that no additional solvent is necessary Bases which are suitable for the process are all inert bases which are able to bin d hydrogen iodide or hydrogen bromide liberated during the reaction. Examples which may be mentioned here are tertiary amines, such as tert-alkylamines, for example trialkylamines, such as triethylamine, cyclic amines, such as N-methylpiperidine or N,N'-dimethylpiperazine, pyridine, alkali metal carbonates or bicarbonates, or tetraalkyl-substituted urea derivatives, such as tetra-$C_1$–$C_4$-alkylurea, for example tetramethylurea, The amount of base is not critical, customarily from 1 to 10, in particular from 1 to 5, mol are used when the base is simultaneously used as solvent, the amount is generally such that the fraction components are dissolved, unnecessarily high excesses being avoided for reasons of practicability in order to save costs, to be able to employ small reaction vessels and to ensure that the reaction components have maximum contact.

During the reaction, the carbon monoxide pressure is adjusted such that an excess of Co, based on XIV, is always present. At room temperature, the carbon monoxide pressure is preferably from 1 to 250 bar, in particular from 5 to 150 bar, of CO.

The carbonylation is generally carried out continuously or batchwise at from 20 to 250° C., in particular from 30 to 150° C. In the case of batchwise operation, carbon monoxide is advantageously continuously injected onto the reaction mixture to maintain a constant pressure.

The 5-bromobenzothiazoles XIV used as starting materials are known or can easily be prepared by suitable combination of known syntheses and according to the reaction sequence described in scheme 3.

According to scheme 3, it is possible, for example, to convert o-chloronitrobenzenes of the formula XIII into the corresponding o-nitrothioethers using alkali metal salts of alkylmercaptans (step k). The resulting thioether can be brominated selectively in the 3-position with respect to the nitro group (step l). Brominating reagents which are customarily used for this purpose are, in addition to bromine— if appropriate in combination with a Lewis acid such as $FeBr_3$ —, also N-bromosuccinimide, N-bromohydantoin and pyridinium perbromide. The bromination is preferably carried out in an organic solvent, for example an aliphatic or cycloaliphatic hydrocarbon, halogenated hydrocarbon or anhydrous organic acids, at temperatures in the range from −15 to 150° C., preferably in the range from −15 to 100° C. (see, for example, organikum, 16th edition, 1986, p. 315). Subsequently, in step m), the nitro group is reduced to the amino group. The conditions for step m) correspond to the conditions given for step c) in scheme 1. The o-aminothioether from step m) is subsequently, in step n), cyclized to the 5-bromobenzothiazole XIV. The reaction conditions required for this step correspond to the conditions given for step a) in scheme 1.

For preparing the benzothiazole S-dioxide compounds of the formula I ($Y=SO_2$), for example, the benzothiazole-5-carboxylic acids IV-1a or IV-1b or the 5-bromobenzothiazole-5-carboxylic acids XIV are reacted with an oxidizing agent giving the corresponding S-dioxide, which is then processed further as described to give the target compound of the formula I where $Y=SO_2$. However, preference is given to initially oxidizing the thiomethyl ether of the formula VIII (scheme 1, formula VIII where R=H and R'=$CH_3$) to give the S-dioxide VIIIc, which is subsequently cyclized to give the benzothiazole S-dioxide 5-carboxylic acid of the formula IV-1c.

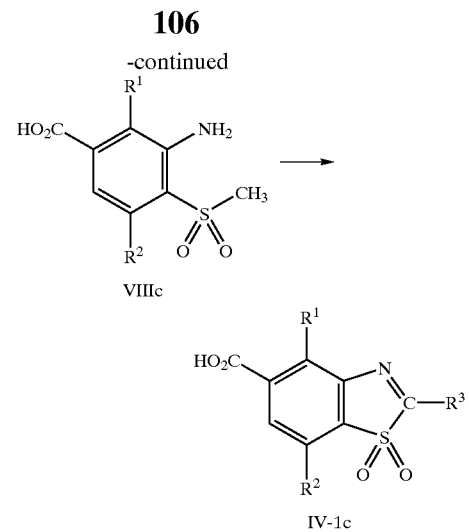

The oxidation of VIII to the S-dioxide is carried out using oxidizing agents, such as peroxy acids, for example m-chloroperbenzoic acid, peroxyacetic acid, trifluoroperoxyacetic acid, or using hydrogen peroxide, which is preferably employed together with a transition metal catalyst, for example sodium tungstate (VI). The cyclization of o-methylsulfonylaminobenzenes of the formula VIIIc is carried out analogously to the method described in Chem. Heterocycl. Comp. Vol.3, 1967, p.197 ff.

A synthesis of benzoxazole-5-carboxylic acid derivatives of the formula IV-2 ($X=C-R^3$, $Y=O$) is described in scheme 4. Here, starting from 3-nitrotoluenes of the formula IX, a 3-aminobenzoic. ester of the formula Xb (R=$C_1$–$C_4$-alkyl) is initially prepared in the manner described for scheme 1. In step p), the amino group in Xb is first diazotized in a known manner, and the product is subsequently reacted with alkali metal azides to give the corresponding 3-azidobenzoic acids of the formula XV. The azide XV is then, in reaction step q), reacted with an alkanecarboxylic acid, which may also be halogenated, for example formic acid, acetic acid, trifluoroacetic acid or propionic acid, to give the benzoxazole-5-carboxylic ester of the formula IV-2a ($R^3=C_1$–$C_4$-alkyl). The compound IV-2a can either be reacted directly to give the cyclohexenone derivative of the formula I according to the invention where $X=CR^3$ and $Y=O$ or, alternatively, be hydrolyzed in reaction step r) to give the o-aminophenol of the formula XVI. Like the o-aminothiophenols of the formula VIII, the compounds XVI can then be converted into the benzoxazole-5-carboxylic esters of the formula IV-2.

Scheme 1a

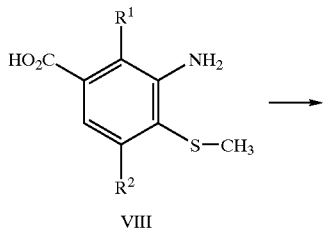

Scheme 4

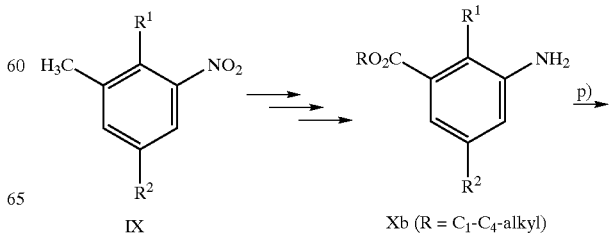

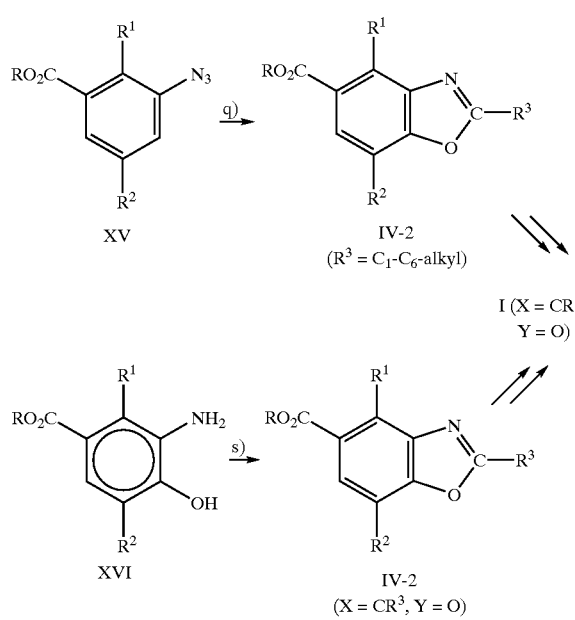

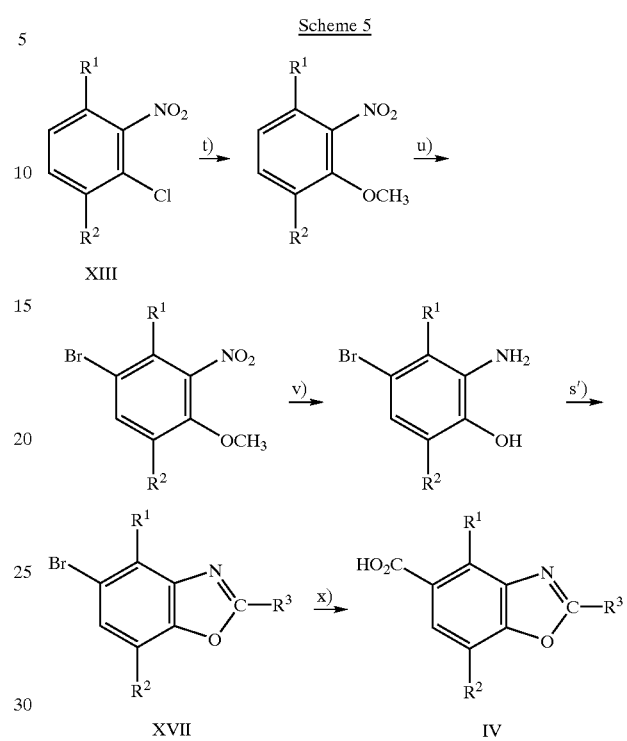

In reaction step p), initially an aromatic diazonium compound is prepared from the amine of the formula Xb, in aqueous acidic solution or in an anhydrous acid, such as formic acid, acetic acid or trifluoroacetic acid, using an inorganic nitrite, such as sodium nitrite, or an organic nitrite, such as isoamyl nitrite. An alkali metal azide, for example sodium azide, is then added to the solution or suspension of the diazonium compound, giving the 3-azidobenzoic ester according to scheme 4. The reaction temperature for the reaction is generally in the range from −15 to +50° C., preferably in the range from 0 to 20° C. See also K. G. Pinney et al., J. Org. Chem. [JOCEAH] 56 (9) (1991), 3125–3133.

Reaction step q) is preferably carried out in the anhydrous acid HOOC—$R^3$ which is desired for the condensation, in an aromatic hydrocarbon, such as benzene, toluene, xylene or chlorobenzene. The reaction temperature is generally in the range from 0 to 150° C. and preferably in the range from 50 to 145° C. (See also B. Decroix et al., Bull. Soc. Chim. Fr. 1976, 621; S. Chaudhury et al., Can. J. Chem. 60 (1982), 1122). The hydrolysis of the benzoxazole-5-carboxylic ester obtained in step q) to give the 3-amino-4-hydroxybenzoic ester of the formula XVI is carried out, for example, under the conditions given for reaction step e) in scheme 1. The condensation of compound XVI to the benzoxazole-5-carboxylic ester in step s) is carried out, for example, under the reaction conditions given for step a) in scheme 1. (For step s), see also Houben-Weyl, "Methoden der organischen Chemie", Vol. E8a, 1993, p. 1020 f.)

Another route to the benzoxazole-5-carboxylic acids of the formula IV (X=C—$R^3$, Y=O) is shown in scheme 5.

Here, an o-chloronitrobenzene of the formula XIII is initially converted by nucleophulic exchange of halogen for methoxy into an o-nitroanisole (step t)). This is then brominated under the reaction conditions given for step 1) in scheme 3, the bromine atom being introduced selectively into the p position to the methoxy group. The brominated nitroanisole is then initially reduced selectively to give the amino compound, and the hydroxyl function is subsequently released by ether cleavage. This gives 2-amino-4-bromophenols. These are then cyclized to the 5-bromobenzoxazole of the formula XVII under the reaction conditions given for step s). The compound XVII is then reacted under the reaction conditions described for step o) in scheme 3 to give the benzoxazole-5-carboyxlic acid of the formula IV (X=C—$R^3$ and Y=O).

A process for preparing benzimidazole-5-carboxylic esters is shown in scheme 6.

Scheme 6

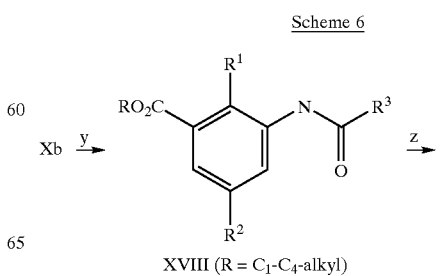

XVIII (R = $C_1$-$C_4$-alkyl)

-continued

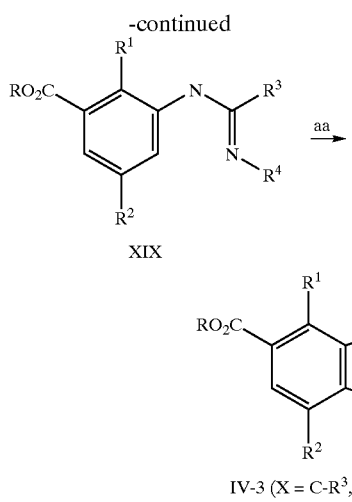

XIX

IV-3 (X = C-R³, Y = C-R⁴)

Once more, 3-nitrotoluenes are used as starting materials here, X and they are converted in the manner described above into 3-aminobenzoic esters of the formula Xb. The compounds Xb are then, in reaction step y), reacted with a carboxylic acid of the formula $R^3$–$CO_2H$ or a reactive carboxylic acid equivalent $RCOL^1$, where $L^1$ is as defined above, to give a carboxamide of the formula XVIII. Here, $R^3$ has one of the meanings given above. XVIII is then converted under acidic conditions, for example with phosgene or phosphoryl chloride, into a nitrilium ion, which is quenched with an amine of the formula $R^4$-$NH_2$ or ammonia, resulting in an imino amide of the formula XIX. The compound XIX can then be converted under oxidizing conditions, as described, for example, for reaction step b) or g) in scheme 1, into the benzimidazole-5-carboxylic ester, which for its part can be hydrolyzed to give the carboxylic acid.

Step y) is generally carried out under the customary reaction conditions for forming carboxamides from carboxylic acids or carboxylic acid derivatives and aromatic amines. The reaction temperature is generally in the range from –15 to 200° C., preferably in the range from 20 to 150° C.

For preparing the imino amide of the formula XIX, the amide of the formula XVIII is initially dissolved under exclusion of water in an organic solvent, for example one of the abovementioned cycloaliphatic or aromatic hydrocarbons or an ether, and converted into the nitrilium ion using an inorganic acid, for example hydrochloric acid or sulfuric acid, a Lewis acid, such as titanium tetrachloride, or an acid chloride, such as sulfonyl chloride, sulfuryl chloride, phosphoryl chloride or phosgene. The required temperatures for this are generally in the range from –15 to 150° C. and preferably in the range from 20 to 140° C. The nitrilium ion is then quenched with ammonia or an amine of the formula $R^4$-$NH_2$.

The cyclization of the compound XIX to the benzimidazole-5-carboxylic ester of the formula IV (X=C—$R^3$, Y=C—$R^4$) is generally carried out using an oxidizing agent, such as lead tetraacetate, thallium(III)nitrite, sulfuryl chloride or sodium hypochloride, under anhydrous conditions. Suitable solvents are, for example, aliphatic or cycloaliphatic hydrocarbons, aromatic hydrocarbons or ethers. The reaction is generally carried out in the range from –15 to +150° C. and preferably in the range from 0 to 140° C. For the preparation of benzimidazoles from iminoamides see also Can. J. Chem. 60 (1982), p.1122.

Benzoisothiodiazoles of the formula IV-4 (X—Y=S=N) are prepared, for example, starting from benzimidazole-5-carboxylic acids or their esters, in the manner described in scheme 7.

Scheme 7

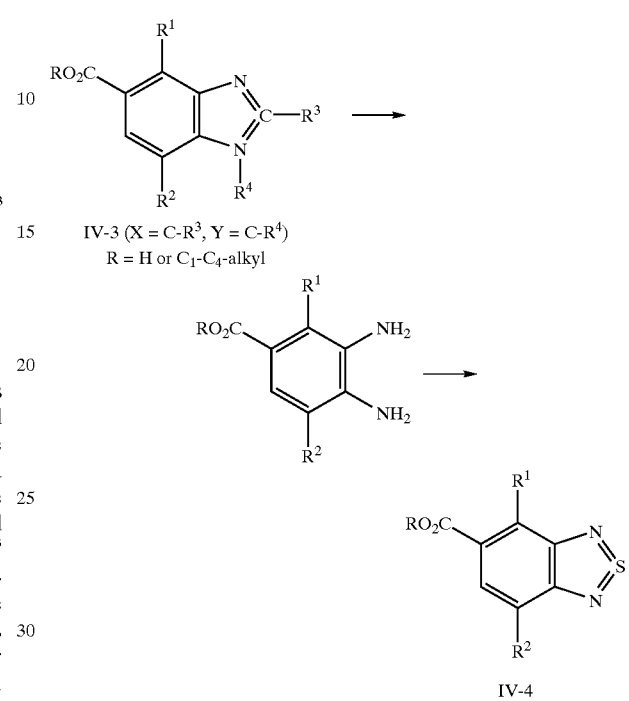

IV-3 (X = C-R³, Y = C-R⁴)
R = H or $C_1$-$C_4$-alkyl

IV-4

In this case a benzimidazolecarboxylic ester or the free, carboxylic acid is initially hydrolyzed to 3,4-diaminobenzoic acid. This is subsequently cyclized with sulfurous acid or its derivatives, for example $SO_2$ or $SO_2Cl_2$, to give the benzoisothiadiazole-5-carbbxylic acid of the formula IV-4. The cyclization is usually carried out at from 0 to 200° C. and preferably in the range from 50 to 150° C., for example in a solvent or in the melt (see also: Chem. Ber. 100 (1967), p. 2164).

Scheme 8

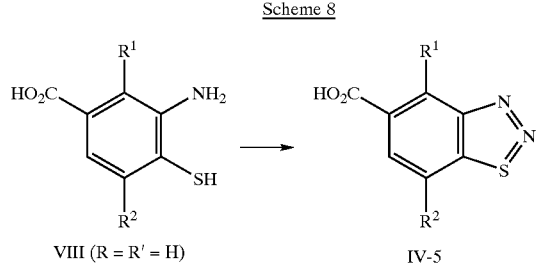

VIII (R = R' = H)   IV-5

Benzothiadiazole-5-carboxylic acids of the formula IV-5 (X=N, Y=S) can be prepared starting from 2-aminothiophenol-5-carboxylic acids of the formula VIII (R=R'=H). To this end, the compounds of the formula VIII are initially diazotized, for example by reaction with organic or inorganic nitrite in an aqueous neutral reaction medium in the range from –15 to +20° C. The aqueous solution or suspension of the diazonium salt is subsequently acidified, whereupon the compound of the formula IV-5 forms. This can be obtained in a conventional manner from the reaction mixture, for example by extraction with an organic solvent. The preparation of the starting materials VIII is described in scheme 1. The benzothiadiazolecarboxylic acids IV-5 (X=N, Y=S) can be prepared, for example, analogously to the process described in U.S. Pat. No. 5,770,758.

EXAMPLES

Abbreviations used:
EDC=ethyl(3'-dimethylaminopropyl)carbodiimide
DMAP=4-dimethylaminopyridine 5-(1'-Hydroxycyclohex-2'-en-3'-on-2'-ylcarbonyl)-1-methylbenzo-triazole (Example 1)
1.1 Cyclohexen-3-on-1-yl 1-methylbenzotriazole-5-carboxylate

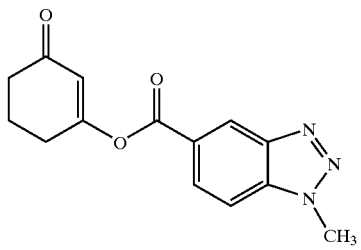

1.5 g of 1-methylbenzotriazole-5-carboxylic acid (8.5 mmol) and 1.0g of 1,3-cyclohexanedione (8.9 mmol) were dissolved in 30 ml of abs. acetonitrile and admixed with 1.6 g of EDC (8.5 mmol), 2 ml of triethylamine and a cat. amount of DMAP. After the reaction had ended, the solution was poured into water and extracted with ethyl acetate. The organic phase was washed and dried and the product was then purified by crystallization. Yield: 1.35 g (59%).
m.p.: 154–158° C.
1.2 5-(1'-Hydroxycyclohex-2'-en-3'-on-2'-ylcarbonyl)-1-methylbenzotriazole

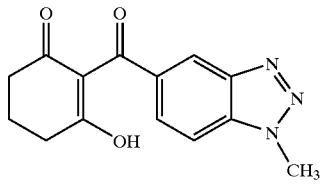

0.74 g (2.7 mmol) of cyclohexen-3-on-1-yl 1-methylbenzotriazole-5-carboxylate was dissolved in 30 ml of acetonitrile and admixed with 0.53 g of triethylamine (5.3 mmol) and 0.15 g of trimethylsilyl cyanide (1.5 mmol). The mixture was stirred at room temperature until the reaction had gone to completion, the solvent was removed under reduced pressure and the residue was taken up in water. The aqueous phase was extracted with methylene chloride, adjusted to pH 2 and extracted with ethyl acetate. The solvent was removed and the product was then purified by trituration. Yield: 0.5 g (68%).

$^1$H NMR (D$_6$-DMSO, TMS) δ=2.03 (m, 2H); 2.48 (m, 4H); 4.37 (s,3H); 7.90 (d, 1H); 7.98 (d, 1H); 8.22 (s, 1H).

The compounds of Example 2 to 40 were prepared analogously by reacting the respective carboxylic acid IVa with the appropriate cycolhexan-1,3-dione.

| Ex. | Structure/Compound No. | M.p. [° C.] or $^1$H-NMR [ppm] |
|---|---|---|
| 1 | I-4a.37 | D$_6$-DMSO, TMS: 2.03(m, 2H), 2.48(m, 4H), 4.37(s, 3H), 7.90(d, 1H), 7.98(d, 1H), 8.22(s, 1H) ppm. |
| 2 | I-1a.394 | 211–215° C. |
| 3 | I-1c.394 | 127–130° C. |

-continued
| Ex. | Structure/Compound No. | M.p. [° C.] or ¹H-NMR [ppm] |
|---|---|---|
| 4 | 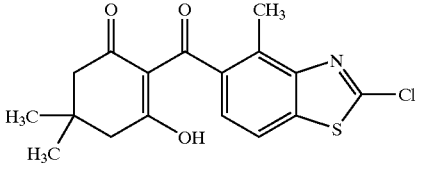 I-1c.396 | CDCl$_3$, TMS: 1.12(s, 6H), 2.34(s, 2H), 2.59(s, 3H), 2.65(s, 2H), 7.18(d, 1H), 7.63(d, 1H), 17.64(OH) ppm. |
| 5 | 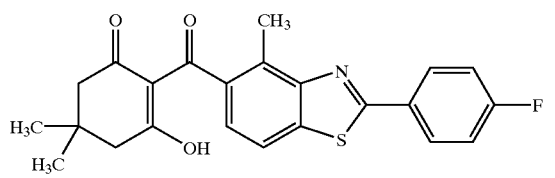 I-1c.457 | CDCl$_3$, TMS: 1.12(s, 6H), 2.35(s, 2H), 2.64(s, 2H), 2.70(s, 2H), 7.1–7.2(m, 3H), 7.76(d, 1H), 8.05–8.15(m, 2H), 17.75(OH) ppm. |
| 6 | 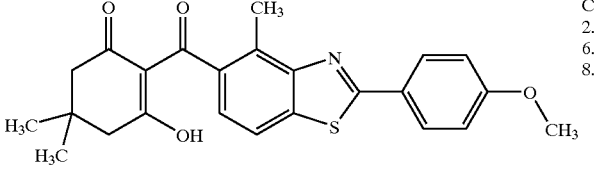 I-1c.466 | CDCl$_3$, TMS: 1.13(s, 6H), 2.35(s, 2H), 2.64(s, 2H), 2.72(s, 2H), 3.87(s, 3H), 6.98(d, 2H), 7.1(d, 1H), 7.73(d, 1H), 8.02(d, 2H), 17.78(OH) ppm. |
| 7 | 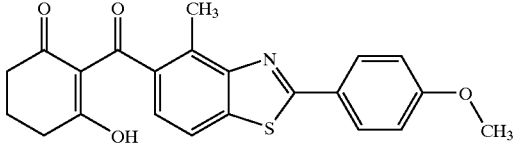 I-1a.466 | CDCl$_3$, TMS: 2.04(m, 2H), 2.45(t, 2H), 2.74(s, 3H), 2.79(t, 2H), 3.84(s, 3H), 6.98(d, 2H), 7.1(d, 1H), 7.72(d, 1H), 8.02(d, 2H), 17.68(OH) ppm. |
| 8 | 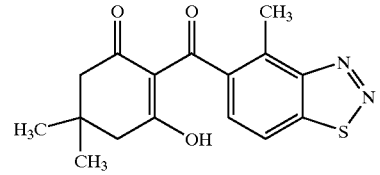 I-4c.2 | 120–122° C. |
| 9 | 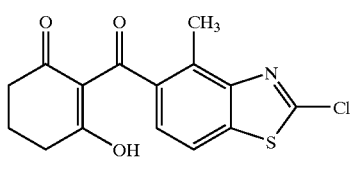 I-1a.396 | 154–155° C. |
| 10 | 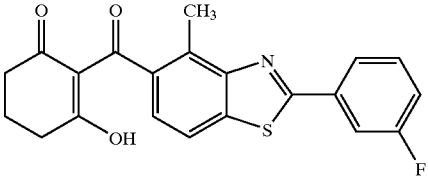 I-1a.456 | 148–150° C. |

| Ex. | Structure/Compound No. | M.p. [° C.] or $^1$H-NMR [ppm] |
|---|---|---|
| 11 | 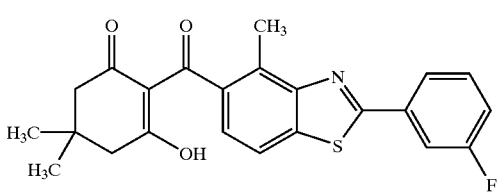<br>I-1c.456 | 158–160° C. |
| 12 | 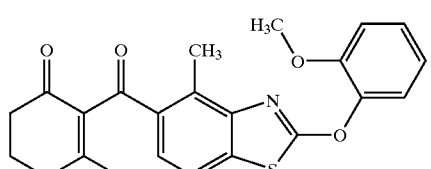<br>I-1a.802 | 150–155° C. |
| 13 | 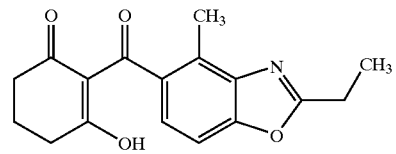<br>I-2a.406 | CDCl$_3$, TMS: 1.42(t, 3H), 2.04(m, 2H), 2.55(s, 3H), 2.63(4H), 2.98(q, 2H), 7.07(d, 1H), 7.33(d, 1H), 17.64(OH) ppm. |
| 14 | 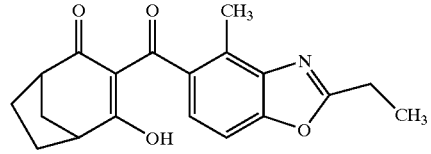<br>I-2x.406 | CDCl$_3$, TMS: 1.42(t, 3H), 1.7–1.85(m, 2H), 2.0–2.34(m, 4H), 2.48(s, 3H), 2.9(1H), 2.98(q, 2H), 3.18(1H), 7.08(d, 1H), 7.33(d, 1H), 17.68(OH) ppm. |
| 15 | 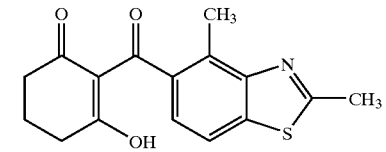<br>I-1a.405 | 112–115° C. |
| 16 | 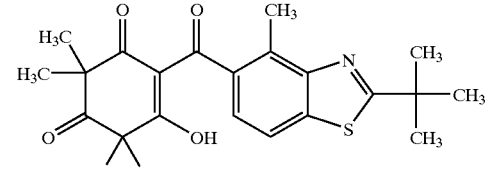<br>I-1d.412 | CDCl$_3$, TMS: 1.34(s, 6H), 1.49(s, 9H), 1.56(s, 6H), 2.70(s, 3H), 7.04(d, 1H), 7.7(d, 1H), 17.95(OH) ppm. |
| 17 | 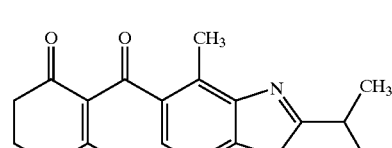<br>I-1a.408 | CDCl$_3$, TMS: 1.42(d, 6H), 2.08(m, 2H), 2.46(2H), 2.64(s, 3H), 2.8(2H), 3.42(m, 1H), 7.09(d, 1H), 7.7(d, 1H), 17.7(OH) ppm. |

-continued
| Ex. | Structure/Compound No. | M.p. [° C.] or ¹H-NMR [ppm] |
|---|---|---|
| 18 | 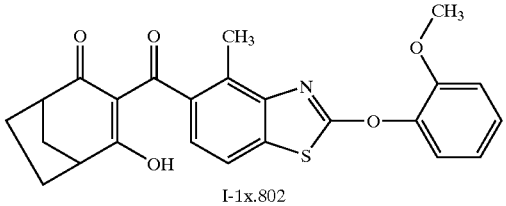 I-1x.802 | CDCl₃, TMS: 1.7–1.85(m, 2H), 2.0–2.34(m, 4H), 2.48(s, 3H), 2.9(1H), 3.18(1H), 3.92(s, 3H), 7.0–7.1(m, 3H), 7.25–7.38(m, 2H), 7.67(d, 1H), 17.65(OH) ppm. |
| 19 | 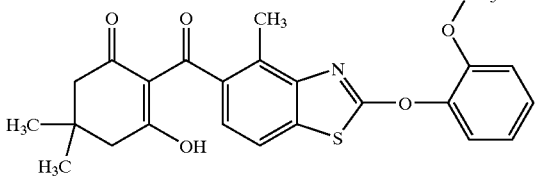 I-1c.802 | 138–141° C. |
| 20 | 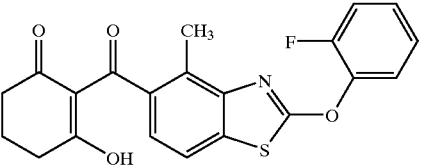 I-1a.790 | CDCl₃, TMS: 2.04(m, 2H), 2.42(2H), 2.46(s, 3H), 2.77(2H), 7.02(d, 1H), 7.15–7.33(m, 3H), 7.4–7.55(m, 2H), 17.63(OH) ppm. |
| 21 | 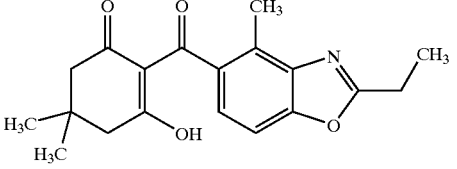 I-2c.406 | CDCl₃, TMS: 1.14(s, 6H), 1.42(t, 3H), 2.36(s, 2H), 2.54(s, 3H), 2.69(s, 2H), 2.98(q, 2H), 7.08(d, 1H), 7.3(d, 1H), 17.7(OH) ppm. |
| 22 | 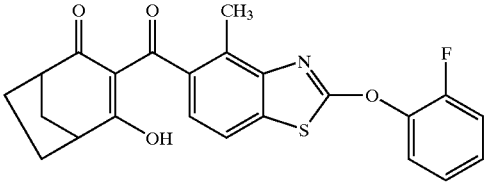 I-1x.790 | CDCl₃, TMS: 1.7–1.85(m, 2H), 2.0–2.34(m, 4H), 2.63(s, 3H), 2.9(1H), 3.18(1H), 7.08(d, 1H), 7.15–7.33(m, 3H), 7.6(dd, 1H), 7.7(d, 1H), 17.6(OH) ppm. |
| 23 | 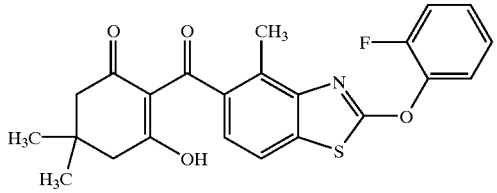 I-1c.790 | 122–174° C. |
| 24 | 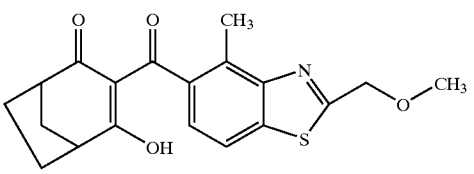 I-1x.420 | 92–98° C. |

-continued

| Ex. | Structure/Compound No. | M.p. [° C.] or $^1$H-NMR [ppm] |
|---|---|---|
| 25 | I-1a.420 | 97–101° C. |
| 26 | I-1c.418 | 160–167° C. |
| 27 | I-1a.406 | 99–101° C. |
| 28 | I-1a.418 | 167–170° C. |
| 29 | I-1x.418 | 127–143° C. |
| 30 | I-1x.394 | 128–136° C. |
| 31 | I-1x.406 | CDCl$_3$, TMS: 1.42(t, 3H), 1.7–1.9(m, 2H), 2.0–2.3(m, 4H), 2.62(s, 3H), 2.9(1H), 3.18(m, 3H), 7.1(d, 1H), 7.7(d, 1H), 17.7(OH) ppm. |

-continued

| Ex. | Structure/Compound No. | M.p. [° C.] or ¹H-NMR [ppm] |
|---|---|---|
| 32 | I-1x.435 | CDCl₃, TMS: 1.7–1.8(m, 2H), 2.0–2.3(m, 4H), 2.6(s, 3H), 2.78(s, 3H), 2.9(1H), 3.18(1H), 7.04(d, 1H), 7.58(d, 1H), 17.7(OH) ppm. |
| 33 | I-1x.397 | 70–73° C. |
| 34 | I-1a.397 | 149–152° C. |
| 35 | I-1a.435 | CDCl₃, TMS: 2.0(m, 2H), 2.52(2H), 2.59(s, 3H), 2.78(s, 3H), 2.9(2H), 7.03(d, 1H), 7.6(d, 1H), 17.7(OH) ppm. |
| 36 | I-1d.418 | CDCl₃, TMS: 1.3(s, 6H), 1.38(s, 6H), 2.78(s, 3H), 7.27(d, 1H), 7.88(d, 1H), 17.7(OH) ppm. |
| 37 | I-1a.808 | 129–133° C. |
| 38 | I-1x.808 | 125–128° C. |

-continued

| Ex. | Structure/Compound No. | M.p. [° C.] or $^1$H-NMR [ppm] |
|---|---|---|
| 39 | 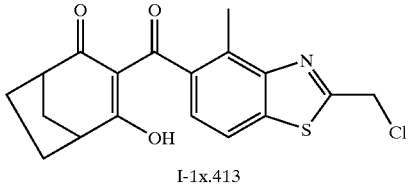<br>I-1x.413 | CDCl$_3$, TMS: 1.7–1.85(m, 2H), 2.0–2.34(m, 4H), 2.62(s, 3H), 2.9(1H), 3.18(1H), 4.93(s, 2H), 7.17(d, 1H), 7.77(d, 1H), 17.7(OH) ppm. |
| 40 | 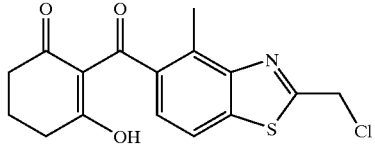<br>I-1a.413 | 95–97° C. |

The compounds of the formula I and their agriculturally useful salts are suitable, both as isomer mixtures and in the form of the pure isomers, for use as herbicides. The herbicidal compositions comprising compounds of the formula I effect very good control of vegetation on non-crop areas, especially at high application rates. In crops such as wheat, rice, maize, soybeans and cotton, they act against broad-leaved weeds and grass weeds without causing any significant damage to the crop plants. This effect is observed in particular at low application rates.

Depending on the application method in question, the compounds of the formula I or the herbicidal compositions comprising them can additionally be employed in a further number of crop.plants for eliminating undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds of the formula I can also be used in crops which tolerate the action of herbicides due to breeding, including genetic engineering methods.

The compounds of the formula I, or the herbicidal compositions comprising them, can be applied, for example, in the form of directly sprayable aqueous solutions, powders, suspensions, including highly-concentrated aqueous, oily or other suspensions or dispersions, emulsions, oil dispersions, pastes, dusts, materials for broadcasting or granules, by means of spraying, atomizing, dusting, broadcasting or pouring. The use forms depend on the intended purposes; in each case, they should ensure the finest possible distribution of the active ingredients according to the invention.

The herbicidal compositions comprise a herbicidally effective amount of at least one compound of the formula I or an agriculturally useful salt of I and usually the auxiliaries which are customarily used for formulating crop protection agents.

Suitable inert auxiliaries are essentially:

mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexenone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions,the benzoheterocyclyl-cyclohexenones of the formula I, as such or dissolved in an oil or solvent, can be homogenized in water by means of wetting agent, tackifier, dispersant or emulsifier. Alternatively, it is possible to prepare concentrates of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and the salts of sulfated hexa-, hepta- and octadecanols and of fatty alcohol glycol ethers, condensates of sulfonated naphthalene and its derivatives with formaldehyde, con densates of naphthalene or of the naphthalenesulf onic acids with phenol and formaldehyde, polyoxyethylene octyxphenol ether, ethoxyoated isooctyl-, octyl- or nonylphenol, alkylphenyl polyglycol ether, tributylphenyl polyglycol ether, alkylaryl polyester alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, less, clay, dolomite, diatomacetus earth, calcium sulfate, magnesium sulfate, magnesium oxide, ground synthetic materials, fertilizers such as ammonium sulfate, aiionium phosphate, ammonium nitrate, ureas, and products of vegetable origin such as cereal meal, tree bark meal, wood meal and nutshell meal, cellulose powders, or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound of the formula I in question are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbendzenesulfonate and 5 parts by weight of the adduct of 40 mol of ethylene oxide to 1mol of castor oil. Pouring the solution into 100,000 parts by weight of water and finely distributing it therein gives an aqueous dispersion which comprises 0.02% by weight of the active ingredient.

II. 20 parts by weight of the compound of the formula I in question are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the compound of the formula I in question are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the compound of the formula I in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the compound of the formula I in question are mixed with 97 parts by weight of finely divided kaolin. This gives a dust which comprises 3% by weight of the active ingredient.

VI. 20 parts by weight of the compound of the formula I in question are mixed intimately with 2 parts by weight of calcium dodecylbenzenesulfonate, 8 parts by weight of fatty alcohol polyglylcol ether, 2 parts by weight of the sodium salt of a phenol/urea/formaldehyde condensate and 68 parts by weight of a paraffinic mineral oil. This gives a stable oily dispersion.

VII. 1 part by weight of the compound of the formula I in question is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound of the formula I in question is dissolved in a mixture composed of 80 parts by weight of cyclohexanone and 20 parts by weight of Wettol$^R$EM 31 (=non-ionic emulsifier based on ethoxylated castor oil). This gives a stable emulsion concentrate.

The compounds of the formula I, or the herbicidal compositions, can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible,if any, with the leaves of the sensitive crop plants while the active ingredients reach the leaves of undesirable plants which grow underneath, or the bare soil surface (post-directed, lay-by).

Depending on the control target, the season, the target plants and the growth stage, the rates of application of the compound of the formula I are from 0.001 to 3.0, preferably 0.01 to 1.0, kg of active substance (a.s.)/ha.

To widen the spectrum of action and to achieve synergistic effects, the compounds of the formula I according to the invention may be mixed, and applied jointly, with a large number of representatives of other groups of herbicidal or growth-regulating active ingredients. Suitable examples of components in mixtures are 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-p henycpropionic acid and its derivatives, pyrazole, phenylpyrazoles, pyridazines, pyridinecarboxylic acid and its derivatives, pyrimidyl ethers, sulfonamides, sulfonylureas, triazines, triazinones, etriazolinones, triazolecarboxamides and uracils.

Moreover, it may be advantageous to apply the compounds of the formula I, alone or in combination with other herbicides, even in the form of a mixture together with further crop protection agents, for example with pesticides or agents for controlling phytopathogenic fungi or bacteria. Also of interest is the miscibility with mineral salt solutions which are employed for treating nutritional and trace element deficiencies.

USE EXAMPLES

The herbicidal activity of the compounds of the formula I according to the invention was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the, test plants unless this was adversely affected by the active ingredients.

For the post-emergence treatment, the test plants were first, grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rat e of application for the post-emergence treatment was 0.25 or 0.125 kg of a.s. (active substance)/ha.

Depending on the species, the plants were kept at from 10 to 25° C., or 20 to 35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage, or normal course of growth.

The plants used in the greenhouse experiments belonged to the following species:

| Bayer-code | Common name |
| --- | --- |
| AMARE | redroot pigweed |
| AVEFA | wild oats |
| CHEAL | lambsquarters (goosefoot) |
| CAPBP | shepherd's purse |
| DIGSA | fingergrass, hairy |
| ECHCG | barnyard grass |
| EPHHL | spurge |
| GASPA | smallflower |
| GALAP | catchweed bedstraw |
| LAMAM | henbit |
| MYOAR | forget-me-not |
| PAPRH | corn poppy |
| POLPE | ladysthumb |
| SETIT | foxtail |
| STEME | common chickweed |
| SOLNI | black nightshade |
| THLAR | fanweed |
| TRZAS | spring wheat |
| PHBPU | tall morningglory |
| ABUTH | velvet leaf |
| SETFA | giant foxtail |

The following experiments were performed by the post-emergence method.

At application rates of 0.25 and 0.5 kg/ha (a.s.), the compound I-1a.394 of example 2 showed very good herbicidal action against the harmful plants AMARE, CHEAL, IPOSS and POLPE, and selectivity in wheat, when applied by the post-emergence method.

At application rates of 0.25 and 0.5 kg/ha (a.s.), the compound I-1c.396 of example 4 shows good to very good herbicidal action against AMARE, CHEAL, ECHCG and SETFA, when applied by the post-emergence method.

At application rates of 0.125 and 0.25 kg/ha (a.s.), the compound I-2a.406 of example 13 shows very good herbicidal action against ABUTH, AMARE, CHEAL and IPOSS and a good herbicidal action against GALAP, when applied by the post-emergence method.

At application rates of 0.0625 and 0.125 kg/ha (a.s.), the compound I-2x.406 of example 14 shows good to very good herbicidal action against ABUTH, CHEAL, ECHCG and POLPE, when applied by the post-emergence method.

At application rates of 0.25 and 0.125 kg/ha (a.s.), the compound I-1a.405 of example 13 shows very good herbicidal action against AMARE, CHEAL, ECHCG and POLPE, when applied by the post-emergence method.

At application rates of 0.125 and 0.25 kg/ha (a.s.), the compound I-1a.408 of example 17 shows good to very good herbicidal action against ABUTH, CHEAL, ECHCG and POLPE, when applied by the post-emergence method.

At application rates of 0.125 and 0.25 kg/ha (a.s.), the compound I-1x.790 of example 22 shows very good herbicidal action against CHEAL, ECHCG, POLPE and SETFA when applied by the post-emergence method.

At application rates of 0.125 and 0.25 kg/ha (a.s.), the compound I-1x.420 of example 24 shows very good herbicidal action against CHEAL, ECHCG, PHPBU, SETFA and POLPE when applied by the post-emergence method.

At application rates of 0.125 and 0.25 kg/ha (a.s.), the compound I-1x.406 of example 31 shows very good herbicidal action against ABUTH, CHEAL, ECHCG and POLPE when applied by the post-emergence method.

At application rates of 0.0625 and 0.125 kg/ha (a.s.), the compound I-1x.435 of example 32 shows very good herbicidal action against AMARE, CHEAL and ECHCG when applied by the post-emergence method.

We claim:

1. A cyclohexenone compound of benzo-fused unsaturated 5-membered nitrogen heterocycles of the formula I,

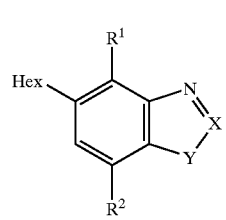

in which

X is a group C—$R^3$ or N;

Y is N-$R^4$, S, SO, $SO_2$ $R^1$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl;

129

$R^2$ is hydrogen, halogen or C1–C6-alkyl;

$R^3$ is hydrogen, halogen, nitro, cyano, hydroxyl, amino, mercapto, thiocyanato, hydrazide, $C_1$–$C_6$-alkyl, $C_1$–$C_6$-haloalkyl, $C_1$–$C_6$-hydroxyalkyl, $C_1$–$C_6$-aminoalkyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_1$–$C_6$-hydroxyalkoxy, $C_1$–$C_6$-alkoxy-$C_1$–$C_6$-alkoxy, $C_3$–$C_6$-cycloalkyl, is $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy and hydroxyl, is $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, is phenyl, naphthyl, phenoxy, phenylamino, diphenylamino, where the phenyl groups of the five last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, is $C(O)OR^5$, or $C(O)N(R^6)R^7$; and $R^4$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy; where $R^5$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl is phenyl, or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

$R^6$, $R^7$ independently of one another are hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, are phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy; and Hex is substituted (3-oxo-1-cyclohexen-2-yl)carbonyl of the formula IIa

IIa where the variables $R^8$ to $R^{14}$ are as defined below:

$R^8$ is hydroxyl, mercapto, halogen, $OR^{15}$, $SR^{15}$, $SOR^{16}$, $SO_2R^{16}$, $OSO_2R^{16}$, $P(O)R^{17}R^{18}$, $OP(O)R^{17}R^{18}$, $P(S)R^{17}R^{18}$, $OP(S)R^{17}R^{18}$, $NR^{19}R^{20}$, or $ONR^{19}R^{20}$ which

130 may be partially or fully halogenated and/or may carry one, to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$, $R^{13}$ independent of one another are hydrogen, $C_1$–$C_4$-alkyl, $C_1$–$C_4$-alkoxycarbonyl;

$R^{10}$, $R^{12}$, $R^{14}$ independently of one another are hydrogen or $C_1$–$C_4$-alkyl;

$R^{11}$ is hydrogen, halogen, hydroxyl, $C_1$–$C_6$-alkyl, $C_1$–$C_6$-haloalkyl, di($C_1$–$C_6$-alkoxy)methyl, ($C_1$–$C_6$- alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-haloalkoxycarbonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last-mentioned radicals may be substituted by one to three $C_1$–$C_4$-alkyl radicals;

or $R^{10}$ and $R^{12}$ or $R^{12}$ and $R^{14}$ together form a π bond or a $C_1$–$C_5$-alkyl chain which may carry one, two or three radicals from the following group: halogen, cyano, $C_1$–$C_4$-alkyl, $C_1$–$C_4$-haloalkyl or $C_1$–$C_4$-allkoxycarbonyl;

or $R^{10}$ and $R^{14}$ together form a $C_1$–$C_4$-alkyl chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^{11}$ and $R^{12}$ together form an —O—$(CH_2)_p$—O—, —O—$(CH_2)_p$—S—, —S—$(CH_2)_p$—S—, —O—$(CH_2)_q$— or —S—$(CH_2)_q$— chain in which p is 2, 3, 4 or 5 and q is 2, 3, 4, 5 or 6, and which may be sustituted by one, two or three radicals from the following group: halogen, cyano, $C_1$–$C_4$-alkyl, $C_1$–$C_4$-haloalkyl or $C_1$–$C_4$-alkocycarbonyl;

or $R^{11}$ and $R^{12}$ together with the carbon to which they are attached form a carbonyl group;

where $R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-(C1–C6-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl and alkoxy radicals mentioned may be partially or fully halogenated and/or may carry one two or three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N-($C_1$–$C_6$-alkyl)-N-phenylaminocarbonyl, phenyl-$C_2$–$C_6$-alkenylcarbonyl radical of the 3 last-mentioned substituents may be partially or fully halogenated and/or may carry one, to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{16}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, or phenyl-$C_1$–$C_4$-alkyl where the phenyl radical of the two last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{17}$, $R^{18}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{19}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_8$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl and alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)aminocarbonyl or $C_3$–$C_6$-cycloalkyl;

is phenyl, phenyl-$C_1$–$C_4$-alkyl, phenylcarbonyl or where the phenyl radical of the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is hydrogen, C1–C6-alkyl or C3–C6-alkenyl, C3–C6-alkynyl;

and its agriculturally useful salts.

2. A pyrazole compound as claimed in claim 1 where X in the formula I is C—$R^3$, where $R^3$ is hydrogen, halogen, cyano, thiocyanato, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, is phenyl, which may be partially or fully halogenated and/or may carry one of the following radicals: $C_1$–$C_4$-alkoxy, $C_1$–$C_4$-haloalkyl, and $C_1$–$C_4$-haloalkoxy;

or is COOR$^5$ where $R^5$ is as defined in claim 1.

3. A cyclohexenone compound as claimed in claim 1 wherein Hex in the formula I is a radical of the formula IIa, where $R^8$ is selected from the group consisting of hydroxyl, mercapto halogen OR$^{15}$, SR$^{15}$, SO$_2$R$^{16}$, NR$^{19}$R$^{20}$ and ONR$^{19}$R$^{20}$, where $R^{15}$, $R^{16}$, $R^{19}$ and $R^{20}$ are as defined in claim 1.

4. A cyclohexenone compound as claimed in claim 3, where in the formula IIa $R^8$ is selected from the group consisting of hydroxyl, $C_1$–$C_4$-alkyloxy, $C_1$–$C_4$-alkylamino, di-$C_1$–$C_4$-alkylamino, N-($C_1$–$C_4$-alkoxy)-N-($C_1$–$C_4$-alkyl)amino, O—CH$_2$-phenyl, phenylthio, phenylcarbonyloxy, 2-, 3- or 4-fluorophenylcarbonyloxy, $C_1$–$C_4$-methylthio, $C_1$–$C_4$-sulfonyloxy, phenylsulfonyloxy and 2-, 3- or 4-methylphenylsulfonyloxy.

5. A cyclohexenone derivative as claimed in claim 1, wherein in the formula IIa or IIB $R^9$, $R^{10}$, $R^{11}$, $R^{12}$, $R^{13}$ and $R^{14}$ independently of one another are hydrogen or $C_1$–$C_4$-alkyl, $R^{11}$ may also be hydroxyl, $C_1$–$C_4$-alkoxy, $C_1$–$C_4$-alkylthio, $C_1$–$C_6$ haloalkoxy or $C_1$–$C_6$ haloalkylthio $R^{11}$ and $R^{12}$ together with the carbon atom to which they are attached may also be a carbonyl group, a 1,3-dioxoiane, 1,3-dithiolane, 1,3-oxothiolane, 1,3-oxothiane, 1,3-dithiolane or a 1,3-dithiane ring, where the 2-position of the six rings mentioned is identical to the carbon atom to which $R^{11}$ and $R^{12}$ are attached, $R^9$ and $R^{13}$ or $R^{10}$ and $R^{14}$ may be a $C_1$–$C_4$-alkylene chain, or $R^{10}$ and $R^{12}$ or $R^{12}$ and $R^{13}$ together may form a π bond.

* * * * *

UNITED STATES PATENT AND TRADEMARK OFFICE
CERTIFICATE OF CORRECTION

PATENT NO. : 6,589,915 B1
DATED : July 8, 2003
INVENTOR(S) : Mayer et al.

It is certified that error appears in the above-identified patent and that said Letters Patent is hereby corrected as shown below:

Column 129,
Line 1, "C1-C6-alkyl" should be -- $C_1$-$C_6$-alkyl --;

Column 130,
Line 2, "one, to three" should be -- one to three --;
Line 55, "C1-C6-alkoxy" should be -- $C_1$-$C_6$-alkoxy --;
Line 60, "one two or" should be -- one, two or --;

Column 131,
Line 7, "one, to three" should be -- one to three --;
Line 36, "$C_3$-$C_8$-alkenyloxy" should be -- $C_3$-$C_6$-alkenyloxy --;

Column 132,
Line 1, "C1-C6-alkyl or C3-C6-alkenyl, C3-C6-" should be
-- $C_1$-$C_6$-alkyl or $C_3$-$C_6$-alkenyl, $C_3$-$C_6$- --;
Line 17, "mercapto halogen $OR^{15}$" should be -- mercapto, halogen, $OR^{15}$ --;
Line 32, delete "IIB; and
Line 39, "dioxoiane" should be -- dioxolane --.

Signed and Sealed this

Twenty-seventh Day of April, 2004

JON W. DUDAS
*Acting Director of the United States Patent and Trademark Office*